US012617846B2

(12) United States Patent
Miano et al.

(10) Patent No.: US 12,617,846 B2
(45) Date of Patent: May 5, 2026

(54) SUBCUTANEOUS (SC) ADMINISTRATION OF ANTI-C5 ANTIBODIES FOR TREATMENT OF COMPLEMENT-ASSOCIATED CONDITIONS

(71) Applicant: Alexion Pharmaceuticals, Inc., Boston, MA (US)

(72) Inventors: Dino C. Miano, Rocky Hill, CT (US); Hweirung Amy Wang, Oak Park, CA (US); Tatyana Mezhebovsky, Branford, CT (US)

(73) Assignee: Alexion Pharmaceuticals, Inc., Boston, MA (US)

( * ) Notice: Subject to any disclaimer, the term of this patent is extended or adjusted under 35 U.S.C. 154(b) by 569 days.

(21) Appl. No.: 18/011,698

(22) PCT Filed: May 6, 2021

(86) PCT No.: PCT/US2021/031141
§ 371 (c)(1),
(2) Date: Dec. 20, 2022

(87) PCT Pub. No.: WO2021/262329
PCT Pub. Date: Dec. 30, 2021

(65) Prior Publication Data
US 2023/0303670 A1     Sep. 28, 2023

Related U.S. Application Data

(60) Provisional application No. 63/043,613, filed on Jun. 24, 2020.

(51) Int. Cl.
A61K 39/395     (2006.01)
A61P 37/02     (2006.01)
C07K 16/18     (2006.01)
C07K 16/00     (2006.01)

(52) U.S. Cl.
CPC .............. C07K 16/18 (2013.01); A61P 37/02 (2018.01); C07K 2317/52 (2013.01); C07K 2317/565 (2013.01); C07K 2317/92 (2013.01)

(58) Field of Classification Search
None
See application file for complete search history.

(56) References Cited

U.S. PATENT DOCUMENTS

| | | |
|---|---|---|
| 3,710,795 A | 1/1973 | Higuchi et al. |
| 4,485,045 A | 11/1984 | Regen |
| 4,544,545 A | 10/1985 | Ryan et al. |
| 4,816,567 A | 3/1989 | Cabilly et al. |
| 4,863,457 A | 9/1989 | Lee |
| 4,868,116 A | 9/1989 | Morgan et al. |
| 4,980,286 A | 12/1990 | Morgan et al. |
| 5,013,556 A | 5/1991 | Woodle et al. |
| 5,308,341 A | 5/1994 | Chanoch |
| 5,443,505 A | 8/1995 | Wong et al. |
| 5,447,145 A | 9/1995 | Cappello et al. |
| 5,501,856 A | 3/1996 | Ohtori et al. |
| 5,624,821 A | 4/1997 | Winter et al. |
| 5,648,260 A | 7/1997 | Winter et al. |
| 5,721,348 A | 2/1998 | Primakoff et al. |
| 5,773,019 A | 6/1998 | Ashton et al. |
| 5,997,848 A | 12/1999 | Patton et al. |
| 6,001,329 A | 12/1999 | Buchsbaum et al. |
| 6,001,386 A | 12/1999 | Ashton et al. |
| 6,005,079 A | 12/1999 | Casterman et al. |
| 6,019,968 A | 2/2000 | Platz et al. |
| 6,095,141 A | 8/2000 | Armer et al. |
| 6,146,361 A | 11/2000 | DiBiasi et al. |
| 6,170,717 B1 | 1/2001 | Di Giovanni et al. |
| 6,192,891 B1 | 2/2001 | Gravel et al. |
| 6,194,551 B1 | 2/2001 | Idusogie et al. |
| 6,200,296 B1 | 3/2001 | Dibiasi et al. |
| 6,277,099 B1 | 8/2001 | Strowe et al. |
| 6,277,375 B1 | 8/2001 | Ward |
| 6,300,064 B1 | 10/2001 | Knappik et al. |

(Continued)

FOREIGN PATENT DOCUMENTS

| | | |
|---|---|---|
| AU | 2018201961 A1 | 4/2018 |
| CA | 2942165 A1 | 9/2015 |

(Continued)

OTHER PUBLICATIONS

Sheridan et al. (PLOS One, 2018, 13(4): e0195909, pp. 1-10. (Year: 2018).*
Peterson et al. Am J Clin Nutr 2016;103:1197-203. (Year: 2016).*
Markarian. Putting Drug Delivery into Patients' Hands, Pharmaceutical Technology 43 (6), Jun. 2, 2019, pp. 1-10. (Year: 2019).*
Brandes. West Pharmaceutical Services, 2015, pp. 1-4. (Year: 2015).*
Schreiber et al., Proc Natl Acad Sci USA 75: 3948-3952 (1978).
Scully, M. et al., "Systemic Involvement at Entry into the Global Atypical Hemolytic Uremic Syndrome (aHUS) Registry," Blood, vol. 128:3729 6 pages (2016).

(Continued)

*Primary Examiner* — Chun W Dahle

(74) *Attorney, Agent, or Firm* — Nelson Mullins Riley & Scarborough LLP; Jane E. Remillard, Esq.; Jill Gorny Sloper, Esq.

(57)     ABSTRACT

Provided are methods for clinical treatment of complement-associated conditions comprising administering to the patient an anti-C5 antibody, or antigen binding fragment thereof, wherein the anti-C5 antibody, or antigen binding fragment thereof, is administered (or is for administration) subcutaneously according to a particular clinical dosage regimen (i.e., at a particular dose amount and according to a specific dosing schedule). In one embodiment, the patient has previously been treated with eculizumab (SOLIRIS®) or ravulizumab (ULTOMIRIS®); particularly intravenously administered SOLIRIS® or ULTOMIRIS®.

23 Claims, 18 Drawing Sheets
Specification includes a Sequence Listing.

(56) References Cited

U.S. PATENT DOCUMENTS

| | | | |
|---|---|---|---|
| 6,302,855 | B1 | 10/2001 | Lav et al. |
| 6,355,245 | B1 | 3/2002 | Evans et al. |
| 6,737,056 | B1 | 5/2004 | Presta |
| 6,933,368 | B2 | 8/2005 | Co et al. |
| 7,112,341 | B1 | 9/2006 | Nagarajan et al. |
| 7,371,826 | B2 | 5/2008 | Presta |
| 7,390,786 | B2 | 6/2008 | Warne et al. |
| 7,556,615 | B2 | 7/2009 | Pettis et al. |
| 7,670,600 | B2 | 3/2010 | Dall'Acqua et al. |
| 7,704,497 | B2 | 4/2010 | Dall'Acqua et al. |
| 7,767,429 | B2 | 8/2010 | Bookbinder et al. |
| 7,846,431 | B2 | 12/2010 | Bookbinder et al. |
| 7,871,607 | B2 | 1/2011 | Bookbinder et al. |
| 8,088,376 | B2 | 1/2012 | Chamberlain et al. |
| 8,105,586 | B2 | 1/2012 | Bookbinder et al. |
| 8,202,517 | B2 | 6/2012 | Bookbinder et al. |
| 8,241,628 | B2 | 8/2012 | Diefenbach-Streiber et al. |
| 8,257,699 | B2 | 9/2012 | Bookbinder et al. |
| 8,323,962 | B2 | 12/2012 | Dall'Acqua et al. |
| 8,367,805 | B2 | 2/2013 | Chamberlain et al. |
| 8,431,124 | B2 | 4/2013 | Bookbinder et al. |
| 8,431,380 | B2 | 4/2013 | Bookbinder et al. |
| 8,450,470 | B2 | 5/2013 | Bookbinder et al. |
| 8,568,713 | B2 | 10/2013 | Frost et al. |
| 8,580,252 | B2 | 11/2013 | Bookbinder et al. |
| 8,765,685 | B2 | 7/2014 | Bookbinder et al. |
| 8,772,246 | B2 | 7/2014 | Bookbinder et al. |
| 8,802,820 | B2 | 8/2014 | Chamberlain et al. |
| 8,883,158 | B2 | 11/2014 | Diefenbach-Streiber et al. |
| 9,079,949 | B1 * | 7/2015 | Andrien, Jr. .............. A61P 7/06 |
| 9,107,861 | B1 | 8/2015 | Andrien, Jr. et al. |
| 9,206,251 | B2 | 12/2015 | Andrien, Jr. et al. |
| 9,211,315 | B2 | 12/2015 | Bookbinder et al. |
| 9,345,661 | B2 | 5/2016 | Adler et al. |
| 9,371,377 | B2 | 6/2016 | Andrien, Jr. et al. |
| 9,447,176 | B2 | 9/2016 | Rother et al. |
| 9,556,263 | B2 | 1/2017 | Zhou et al. |
| 9,562,223 | B2 | 2/2017 | Bookbinder et al. |
| 9,663,574 | B2 | 5/2017 | Andrien, Jr. et al. |
| 9,677,061 | B2 | 6/2017 | Bookbinder et al. |
| 9,677,062 | B2 | 6/2017 | Bookbinder et al. |
| 9,771,418 | B2 | 9/2017 | Rother et al. |
| 9,803,007 | B1 | 10/2017 | Andrien, Jr. et al. |
| 10,227,400 | B2 | 3/2019 | Andrien, Jr. et al. |
| 10,584,164 | B2 | 3/2020 | Andrien, Jr. et al. |
| 10,835,574 | B2 | 11/2020 | DeMarco et al. |
| 11,365,241 | B2 | 6/2022 | Ortiz et al. |
| 11,434,280 | B2 | 9/2022 | Andrien, Jr. et al. |
| 11,571,517 | B2 | 2/2023 | Bar-El et al. |
| 12,012,448 | B2 | 6/2024 | Ortiz |
| 12,128,101 | B2 | 10/2024 | Payton et al. |
| 12,240,893 | B2 | 3/2025 | Volles et al. |
| 2002/0026176 | A1 | 2/2002 | Varner et al. |
| 2005/0271660 | A1 | 12/2005 | Wang |
| 2006/0104968 | A1 | 5/2006 | Bookbinder et al. |
| 2006/0141456 | A1 | 6/2006 | Edwards et al. |
| 2007/0172483 | A1 | 7/2007 | Schwaeble et al. |
| 2007/0235029 | A1 | 10/2007 | Zhu et al. |
| 2008/0202513 | A1 | 8/2008 | Birchall et al. |
| 2008/0241223 | A1 | 10/2008 | Nivaggioli et al. |
| 2009/0110679 | A1 | 4/2009 | Li et al. |
| 2010/0098730 | A1 | 4/2010 | Lowman et al. |
| 2011/0111406 | A1 | 5/2011 | Gawa et al. |
| 2012/0225056 | A1 | 9/2012 | Rother et al. |
| 2012/0230982 | A1 | 9/2012 | Zhou et al. |
| 2013/0344088 | A1 | 12/2013 | Cosenza et al. |
| 2014/0056888 | A1 | 2/2014 | Zhou et al. |
| 2015/0299305 | A1 * | 10/2015 | Andrien, Jr. ............ A61P 17/00 |
| | | | 435/69.6 |
| 2016/0108115 | A1 | 4/2016 | Andrien, Jr. et al. |
| 2016/0176921 | A1 | 6/2016 | Rajendran et al. |
| 2016/0176954 | A1 | 6/2016 | Ruike et al. |
| 2016/0251433 | A1 | 9/2016 | Andrien, Jr. et al. |
| 2016/0272700 | A1 | 9/2016 | Zhou et al. |
| 2016/0355579 | A1 | 12/2016 | Rother et al. |
| 2016/0355580 | A1 | 12/2016 | Rother et al. |
| 2017/0298123 | A1 | 10/2017 | Andrien, Jr. et al. |
| 2017/0355757 | A1 | 12/2017 | Hu et al. |
| 2017/0355759 | A1 | 12/2017 | Wang |
| 2017/0369562 | A1 | 12/2017 | Rother et al. |
| 2018/0009885 | A1 | 1/2018 | Andrien, Jr. et al. |
| 2018/0311299 | A1 | 11/2018 | Griffin et al. |
| 2018/0311345 | A1 | 11/2018 | Pober et al. |
| 2019/0023775 | A1 | 1/2019 | Bachman et al. |
| 2019/0263897 | A1 | 8/2019 | Andrien, Jr. et al. |
| 2019/0276524 | A1 | 9/2019 | Griffin et al. |
| 2020/0140531 | A1 | 5/2020 | Rother et al. |
| 2020/0157200 | A1 | 5/2020 | Andrien, Jr. et al. |
| 2020/0254092 | A1 | 8/2020 | Payton et al. |
| 2020/0254185 | A1 | 8/2020 | Bar-El et al. |
| 2020/0369751 | A1 | 11/2020 | Ortiz et al. |
| 2021/0122806 | A1 | 4/2021 | Malanson et al. |
| 2021/0187054 | A1 | 6/2021 | Griffin et al. |
| 2021/0214425 | A1 | 7/2021 | Payton et al. |
| 2021/0332147 | A1 | 10/2021 | Payton et al. |
| 2021/0388070 | A1 | 12/2021 | Denker et al. |
| 2021/0395352 | A1 | 12/2021 | Volles et al. |
| 2022/0235121 | A1 | 7/2022 | Payton et al. |
| 2023/0106734 | A1 | 4/2023 | Ortiz et al. |
| 2023/0235035 | A1 | 7/2023 | Payton et al. |
| 2023/0257456 | A1 | 8/2023 | Ortiz et al. |
| 2023/0303670 | A1 * | 9/2023 | Miano ...................... A61P 7/00 |
| 2024/0141024 | A1 | 5/2024 | Andrien, Jr. et al. |
| 2025/0145698 | A1 | 5/2025 | Andrien et al. |
| 2025/0145700 | A1 | 5/2025 | Volles et al. |

FOREIGN PATENT DOCUMENTS

| | | |
|---|---|---|
| CN | 106459189 A | 2/2017 |
| EP | 430539 A2 | 6/1991 |
| EP | 0488401 A1 | 6/1992 |
| EP | 2006381 A1 | 12/2008 |
| EP | 1610820 B1 | 9/2010 |
| EP | 2275443 A1 | 1/2011 |
| EP | 3095795 A1 | 11/2016 |
| JP | 2010-215674 A | 9/2010 |
| JP | 2010-529999 A | 9/2010 |
| JP | 2013-521772 A | 6/2013 |
| JP | 2013-526861 A | 6/2013 |
| JP | 2015-536930 A | 12/2015 |
| JP | 2017-095440 A | 6/2017 |
| KR | 2008-0110800 A | 12/2008 |
| TW | 1667256 B | 8/2019 |
| WO | 8902468 A1 | 3/1989 |
| WO | 8905345 A1 | 6/1989 |
| WO | 8907136 A2 | 8/1989 |
| WO | 9207573 A1 | 5/1992 |
| WO | 94/02559 A1 | 2/1994 |
| WO | 94/04678 A1 | 3/1994 |
| WO | 94/28027 A1 | 12/1994 |
| WO | 1995029697 A1 | 11/1995 |
| WO | 9734631 A1 | 9/1997 |
| WO | 98/23289 A1 | 6/1998 |
| WO | 98/47531 A2 | 10/1998 |
| WO | 9919343 A1 | 4/1999 |
| WO | 0061178 A1 | 10/2000 |
| WO | 0069887 A2 | 11/2000 |
| WO | 0178693 A2 | 10/2001 |
| WO | 2002/013859 A1 | 2/2002 |
| WO | 2003/074679 A2 | 9/2003 |
| WO | 03105757 A2 | 12/2003 |
| WO | 2004022096 A1 | 3/2004 |
| WO | 2004024156 A1 | 3/2004 |
| WO | 2004026380 A2 | 4/2004 |
| WO | 2004029207 A2 | 4/2004 |
| WO | 2004060407 A1 | 7/2004 |
| WO | 2004073551 A2 | 9/2004 |
| WO | 2004091658 A1 | 10/2004 |
| WO | 2005011735 A1 | 2/2005 |
| WO | 2005040217 A2 | 5/2005 |
| WO | 2005/077981 A2 | 8/2005 |
| WO | 2005092925 A2 | 10/2005 |
| WO | 06/031994 A2 | 3/2006 |
| WO | 2006/053301 A2 | 5/2006 |

(56)        References Cited

FOREIGN PATENT DOCUMENTS

| WO | 2006094234 A1 | 9/2006 |
|----|---------------|--------|
| WO | 2006/105338 A2 | 10/2006 |
| WO | 2006/122257 A2 | 11/2006 |
| WO | 2007041635 A2 | 4/2007 |
| WO | 2007/103134 A2 | 9/2007 |
| WO | 2007/106585 A1 | 9/2007 |
| WO | 2007114319 A1 | 10/2007 |
| WO | 08/043822 A2 | 4/2008 |
| WO | 2008048545 A2 | 4/2008 |
| WO | 2008092117 A2 | 7/2008 |
| WO | 2008/157356 A2 | 12/2008 |
| WO | 2009/041643 A1 | 4/2009 |
| WO | 2009058492 A2 | 5/2009 |
| WO | 2009086320 A1 | 7/2009 |
| WO | 2009125825 A1 | 10/2009 |
| WO | 2010/068722 A1 | 6/2010 |
| WO | 2010/127069 A1 | 11/2010 |
| WO | 2010/138918 A1 | 12/2010 |
| WO | 2010/151526 A1 | 12/2010 |
| WO | 2011/104381 A2 | 9/2011 |
| WO | 2011111007 A2 | 9/2011 |
| WO | 2011/122011 A2 | 10/2011 |
| WO | 2011/137362 A1 | 11/2011 |
| WO | 2011137395 A1 | 11/2011 |
| WO | 2012/073992 A1 | 6/2012 |
| WO | 2012133782 A1 | 10/2012 |
| WO | 2013046704 A2 | 4/2013 |
| WO | 2013047748 A1 | 4/2013 |
| WO | 2013/165690 A1 | 11/2013 |
| WO | 2014/036076 A1 | 3/2014 |
| WO | 2014058021 A1 | 4/2014 |
| WO | 2015021166 A2 | 2/2015 |
| WO | 2015/134894 A1 | 9/2015 |
| WO | 2016/098356 A1 | 6/2016 |
| WO | 2016106291 A1 | 6/2016 |
| WO | 2016/160756 A2 | 10/2016 |
| WO | 2016/209956 A1 | 12/2016 |
| WO | 201712636 A1 | 1/2017 |
| WO | 2017/044811 A1 | 3/2017 |
| WO | 2017051273 A1 | 3/2017 |
| WO | 2017/116848 A1 | 7/2017 |
| WO | 2017/123636 A1 | 7/2017 |
| WO | 2017/218515 A1 | 12/2017 |
| WO | 2018109588 A2 | 6/2018 |
| WO | 2018143266 A1 | 8/2018 |
| WO | 2019/014360 A1 | 1/2019 |
| WO | 2019023564 A1 | 1/2019 |
| WO | 2019/075263 A2 | 4/2019 |
| WO | 2019/084438 A1 | 5/2019 |
| WO | 2019/231983 A1 | 12/2019 |
| WO | 2019/236345 A1 | 12/2019 |
| WO | 2020/006266 A1 | 1/2020 |
| WO | 2020/092549 A1 | 5/2020 |
| WO | 2020/154626 A1 | 7/2020 |
| WO | 2021/091937 A1 | 5/2021 |
| WO | 2021/211940 A1 | 10/2021 |
| WO | 2021262329 A1 | 12/2021 |
| WO | 2022011086 A1 | 1/2022 |
| WO | 2022159373 A1 | 7/2022 |
| WO | 2022265915 A1 | 12/2022 |

OTHER PUBLICATIONS

Second Written Opinion, PCT/US2015/019225, dated Feb. 5, 2016, 10 pages.

Sharma, V.K. et al., "The formulation and delivery of monoclonal antibodies", Therapeutic Monoclonal Antibodies, Chapter 30: 675-711 (2009).

Sheerin, N.S. et al., "A national specialized service in England for atypical haemolytic uraemic syndrome—the first year's experience," QJM: An International Journal of Medicine, 27-33: 7 pages (2016).

Sheridan, D. et al., "Design and preclinical characterization of ALXN1210: A novel anti-05 antibody with extended duration of action," PLoS One, vol. 13 (4): p. e0195909 (2018).

Sheridan, D. et al., "Design and preclinical characterization of ALXN1210: A next generation anti-C5 monoclonal antibody with improved pharmacokinetics and duration of action," Immunobiology, vol. 221(Issue 10): 1158 (2016).

Sheridan, D. et al., "Design and preclinical characterization of ALXN1210: A novel anti-C5 antibody with extended duration of action," PLoS One 13(4): e0195909, 15 pages (2018).

Sheridan, D. et al.,"Design and preclinical characterization of ALXN1210: A novel anti-05 antibody with extended duration of action", PLoS One, vol. 13(4):e0195909 (2018).

Shields et al., J Biol Chem 276(9): 6591-6604 (2001).

Shields et al., J Biol Chem 277(30): 26733-26740 (2002).

Shire, S. et al., "High-concentration antibody formulations," Formulation and Process De-velopment Strategies for Manufacturing Biopharmaceuticals, Chapter 15: 349-381 (2010).

Shopes, Immunol 148: 2918-2922 (1992).

Shu et al., Proc Natl Aced Sci USA 90: 7995-7999 (1993).

Sissons et al., Proc Natl Acad Sci USA 77: 559-562 (1980).

Skerra et al., Science 240: 1038-1040 (1988).

Smith K. et al., "A Phase 3 Open-label, Randomized, Controlled Study to Evaluate the Efficacy and Safety of Intravenously Administered Ravulizumab Compared with Best Supportive Care in Patients with COVID-19 Severe Pneumonia, Acute Lung Injury, or Acute Respiratory Distress Syndrome: A structured summary of a study p," Trials, vol. 21(1):p. 63 (2020).

Southern and Berg, Mol Appl Genet 1:327 (1982).

Southern and Berg, Mol Appl Genet 1:327, 15 pages (1982).

Staelens et al., Mol Immunol 43: 1243-1257 (2006).

Tabrizi, Ma et al., "Elimination mechanisms of therapeutic monoclonal antibodies ," Drug Discovery Today, vol. 11 (1-2):81-88 (2006).

Tanaka, K. et al., "The long-acting C5 inhibitor, ravulizumab, is efficacious and safe in pediatric patients with atypical hemolytic uremic syndrome previously treated with eculizumab," Pediatric Nephrology, vol. 36(4):889-898 (2021).

Thomas et al., Mol Immunol 33(17118): 1389-1401 (1996).

Todorovska et al., J Immunol Methods 248(1): 47-66 (2001).

Tofukuji et al., J Thorac Cardiovasc Surg 166(6): 1060-1068 (1998).

Tsai, H. et al., "A Mechanistic Approach to the Diagnosis and Management of Atypical Hemolytic Uremic Syndrome," Transfusion Medicine Reviews, vol. 28:187-197 (2014).

Van Beusechem et al., Proc Natl Acad Sci USA 89: 7640-7644 (1992).

Van Gurp et al., Am J Transplantation 8(8): 1711-1718 (2008).

Van Kuik-Romeijn et al., Transgenic Res 9(2): 155-159 (2000).

Verhoeyen et al., Science 239: 1534-1536 (1988).

Wang et al., Proc Natl Acad Sci USA 93: 8563-8568 (1996).

Wang et al.,Proc Natl Acad Sci USA 92: 8955-8959 (1995).

Wang, W. et al., "Antibody Structure, Instability, and Formulation," Journal of Pharmaceutical Sciences, American Chemical Society and American Pharmaceutical Association, vol. 96(1):1-26 (2007).

Ward and Zvaifler, J Clin Invest 50(3): 606-16 (1971).

Waters, A. et al., "aHUS caused by complement dysregulation: new therapies on the horizon," Pediatr Nephrol., vol. 26:41-57 (2011).

Weisman et al., Science 249: 146-151 (1990).

Wetsel et al., J Biol Chem 265: 2435-2440 (1990).

Wigler et al., Cell 16: 77 (1979).

Wilson et al., Proc Natl Acad Sci USA 85: 3104-3018 (1988).

Wong, E. et al., "Anticomplement C5 therapy with eculizumab for the treatment of parox-ysmal nocturnal hemoglobinuria and atypical hemolytic uremic syndrome," Translational Research, vol. 165 (2): 306-320 (2017) XP055358380, NL ISSN: 1931-5244, DOI:10.1016/j.trsl.2014.10.010 the whole document.

Wright et al., EMBO J 10(10): 2717-2723 (1991).

Wurzner et al., Complement Inflamm 8: 328-340 (1991).

Xu et al, Cell Immunol 200: 16-26 (2000).

Yenerel, M. et al., "Phase 3 Study of Subcutaneous Versus Intravenous Ravulizumab in Eculizumab-Experienced Adult Patients with PNH: Primary Analysis and 1-Year Follow-Up," Adv. Ther., vol. 40(1):211-232 (2023).

(56)          References Cited

OTHER PUBLICATIONS

Yuksel, S. et al., "First-Line, Early and Long-Term Eculizumab Therapy in Atypical Hemolytic Uremic Syndrome: A Case Series in Pediatric Patients," Pediatr Drugs, vol. 18:413-420 (2016) DOI 10.1007/s40272-016-0194-0.
Zalevsky et al., Nat Biotech 28: 157-159 (2010).
Zuber, J. et al., "new insights into postrenal transplant hemolytic uremic syndrome," Nat. Rev. Nephrol., vol. 7: 23-35 (2011).
Morell et al., J Clin Invest 49(4): 673-680 (1970).
Mueller et al., Mol Immunol 34(6): 441-452 (1997).
Muller-Eberhard, Ann Rev Biochem 57: 321-347 (1988).
Mullett et al., Methods 22: 77-91 (2000).
Mulligan and Berg Proc Natl Acad Sci USA 78: 2072 (1981).
Mullinax et al., BioTechniques 12(6): 864-869 (1992).
Muyldermans et al., Trends Biochem Sci 26: 230-235 (2001).
NCT02946463 ALXN1210 Versus Eculizumab in Complement Inhibitor Treatment-Native Adult Patients With Paroxysmal Nocturnal Hemoglobinuria (PNH), ClinicalTrials.gov, [online], Jul. 28, 2017, [retrieved on Jul. 21, 2022], 7 pags https://clinicaltrials.gov/ct2/history/NCT02946463?V_9 View#StudyPageTop>.
Newkirk et al., Clin Exp Immunol 106(2): 259-264 (1996).
Noris, M. et al., "STEC-HUS, atypical HUS and TTP are all diseases of complement activation," Nat. Rev. Nephrol., vol. 8: 622-633 (2012).
Nuttall et al., Curr Pharm Biotech 1: 253-263 (2000).
Park et al., Anesth Analg 99(1): 42-48 (1999).
Patriquin C. et al., "Eculizumab and Beyond: The Past, Present, and Future of Complement Therapeutics," Transfusion Medicine Reviews, vol. 33(4):256-265 (2019).
Pavisic et al., Int J Pharm 387(1-2)L 110-119 (2010).
Petkova et al., Int Immunol 18(12): 1759-69 (2006).
Poljak, Structure 2(12): 1121-1123 (1994).
Pollock et al., J Immunol Methods 231(1-2): 147-157 (1999).
Qiao et al., Proc Natl Acad Sci USA 105(27): 9337-9342 (2008).
Rabinovici et al., J Immunol 149 1744-1750 (1992).
Raghunandan, S. R. et al., "Complement Inhibition in Severe COVID-19 Acute Respiratory Distress Syndrome," Frontiers in Pediatrics, vol. 8, 6 pages (2020).
Raju, BioProcess International 1(4): 44-53 (2003).
Ranta and Uritti, Adv Drug Delivery Rev 58(11): 1164-1181 (2006).
Rawal and Pangburn, J Immunol 166(4): 2635-2642 (2001).
Reiss, U. et al., "Efficacy and safety of eculizumab in children and adolescents with paroxysmal nocturnal hemoglobinuria," Pediatric Blood and Cancer, vol. 61(9):1544-1550 (2014).
Rich et al., Curr Opin Biotechnol 11: 54-61 (2000).
Riechmann et al., J Immunol Meth 231: 25-38 (1999).
Riechmann et al., Nature 332: 323-327 (1988).
Rinder et al., J Clin Invest 96: 1564-1572 (1995).
Risitano A.M.et al., "Toward complement inhibition 2.0: Next generationanticomplement agents for paroxysmal nocturnalhemoglobinuria," Am. J. Hematol., vol. 93:564-577 (2018).
Roberts et al., Advanced Drug Delivery Reviews 54: 459-476 (2002).
Roeth, A. et al., "Optimization of Dose Regimen for ALXN1210, a Novel Complement C5 Inhibitor, in Patients with Paroxysmal Nocturnal Hemoglobinuria (PNH): Results of 2 Phase 1/2 Studies," Blood,vol. 130:3482 (2017).
Rogers et al., J Nucl Med 38: 1221-1229 (1997).
Rondeau, E. et al., "The long-acting C5 inhibitor, Ravulizumab, is effective and safe in adult patients with atypical hemolytic uremic syndrome naive to complement inhibitor treatment," Kidney International, Mar. 6, 2020, pp. 1-10.
Rondon and Marasco, Annual Review of Microbiology 51: 257-284 (1997).
Roopenian et al., Methods Mol Blol 602: 93-104 (2010).
Roopenian, DC, et al., "FcRn: the neonatal Fc receptor comes of age," Nature Reviews Immunology, vol. 7(9): 115-725 (2007).
Rosenfeld et al., Cell 68: 143-155 (1992).

Roth, A. et al., "Ravulizumab (ALXN1210) in patients with paroxysmal nocturnal hemo-globinuria: results of phase 1b/2 studies", Blood Adv., vol. 2 (17): 2176-2185 (2018).
Roth, A., et al., "Ravulizumab (ALXN1210) in patients with paroxysmal nocturnal hemoglobinuria: results of 2 phase 1b/2 studies," Blood Adv., vol. 2 (17): 2176-2185 (2018).
Rother , R. et al.,"Discovery and development of the complement inhibitor eculizumab for the treatment of paroxysmal nocturnal hemoglobinuria," Nature Biotechnology, 25 (11): 1256-1264 (1488 Supp) (2007).
Rother et al., Nature Biotechnology 25 (11): 1256-1263 (2007).
Sahelijo L. et al., "First in Human Single-Ascending Dose Study: Safety, Biomarker, Pharmacokinetics and Exposure-Response Relationships of ALXN1210, a Humanized Monoclonal Antibody to C5, with Marked Half-Life Extension and Potential for Significantly Longer Dosing Intervals," Blood, American Society of Hematology, US, vol. 126 (23): 4777 (2015).
Saland, J. et al., "Liver-kidney transplantation to cure atypical HUS: still an option post-eculizumab?," Pediatr Nephrol., DOI 10.1007/s00467-013-2722-2, 4 pages (2013).
Salvadori, M. et al., "Update on hemolytic uremic syndrome: Diagnostic and therapeutic recommendations," World J Nephrol., vol. 2(3): 56-76 (2013).
Samulski et al., J Virol 63: 3822-3828 (1989).
Sarkar, C.,A., et al., "Rational cytokine design for increased lifetime and enhanced potency using pH-activated histidine switching," Nature Biotechnology, vol. 20(9):908-913 (2002).
Sarver et al., Proc Natl Acad Sci USA 79: 7147 (1982).
Sawai et al., Am J Repr Immunol 34: 26-34 (1995).
Schmid et al., Schock 8(2): 119-124 (1997).
Schoonbroodt et al., Nucleic Acids Res 33(9): e81 (2005).
U.S. Appl. No. 18/219,138, filed Jul. 7, 2023, Bruce A. Andrien.
U.S. Appl. No. 17/865,681, filed Jul. 15, 2022, Bruce A. Andrien.
U.S. Appl. No. 16/750,173, filed Jan. 23, 2020, Bruce A. Andrien.
U.S. Appl. No. 16/246,842, filed Jan. 14, 2019, Bruce A. Andrien.
U.S. Appl. No. 15/708,658, filed Sep. 19, 2017, Bruce A. Andrien.
U.S. Appl. No. 15/492,622, filed Apr. 20, 2017, Bruce A. Andrien.
U.S. Appl. No. 15/160,364, filed May 20, 2016, Bruce A. Andrien.
U.S. Appl. No. 14/923,879, filed Oct. 27, 2015, Bruce A. Andrien.
U.S. Appl. No. 14/789,329, filed Jul. 1, 2015, Bruce A. Andrien.
U.S. Appl. No. 14/727,313, filed Jun. 1, 2015, Bruce A. Andrien.
U.S. Appl. No. 14/641,026, filed Mar. 6, 2015, Bruce A. Andrien.
U.S. Appl. No. 17/289,178, filed Apr. 27, 2021, Lori Volles.
Database Medline [Online] US National Library of Medicine (NLM), Bethesda, MD, US; Feb. 2019 (Feb. 2019) Mckeage Kate: "Ravulizumab: First Global Approval," XP002797607, Database accession No. NLM30767127 abstract & Mckeage Kate: "Ravulizumab: First Global Approval," Drugs Feb. 2019, vol. 79, No. 3, Feb. 2019 (Feb. 2019), pp. 347-352, ISSN: 1179-1950.
Dion, M., et al. "Mitigation of oxidation in therapeutic antibody formulations: a biochemical efficacy and safety evaluation of N-acetyl-tryptophan and L-methionine," Pharmaceutical Research, vol. 35: 1-11 (2018).
Fukuzawa T., et al., "Long lasting neutralization of C5 by SKY59, a novel recycling antibody, is a potential therapy for complement-mediated diseases," Sci Rep, vol. 7(1): 12 pages, 1080 (2017).
Haller, Michael F. "Converting intravenous dosing to subcutaneous dosing with recombinant human hyaluronidase." Pharmaceutical Technology, Pharmaceutical Technology, vol. 31, Issue 10, Advanstar Communications Inc (2007).
International Preliminary Report on Patentability, PCT/US2019/058842, dated Apr. 27, 2021, 7 pages.
International Search Report and Written Opinion, PCT/US2019/058842, dated Feb. 26, 2020, 11 pages.
International Search Report and Written Opinion, PCT/US2024/027004, dated Aug. 22, 2024, 10 pages.
Khawaja, Z. et al., 146 Global Phase 3 Clinical Trials Assessing Efficacy and Safety of Ravulizumab in Adults and Children Who Developed Thrombotic Microangiopathy (TMA) After Hematopoietic Stem Cell Transplant (HSCT), American Journal of Kidney Diseases,Elsevier, Amsterdam, NL, vol. 77 (4):612-613 (2021).

(56)                References Cited

OTHER PUBLICATIONS

Launay-Vacher Vincent: An appraisal of subcutaneous trastuzumab: a new formulation meeting clinical needs,: Cancer Chemotherapy and Pharmacology, vol. 72(6):1361-1367 (2013).

Locke, K. et al., "Enhanze® drug delivery technology: a novel approach to subcutaneous administration using recombinant human hyaluronidase PH2O," Drug Delivery, vol. 26 (1): 98-106 (2019).

McNamara, Lucy A. "High risk for invasive meningococcal disease among patients receiving eculizumab (Soliris) despite receipt of meningococcal vaccine," MMWR. Morbidity and mortality weekly report, vol. 66 (2017).

Morgan, V. "Altering Patient Treatment: How SC Delivery Can Help Patients Manage Chronic Conditions," West Pharmaceutical Services, 5 pages (1997).

International Search Report and Written Opinion, PCT/US2021/031141, dated Jul. 20, 2021, 15 pages.

International Search Report and Written Opinion, PCT/US2021/040802, dated Oct. 18, 2021, 9 pages.

International Search Report and Written Opinion, PCT/US2021/045823, dated Dec. 1, 2021, 13 pages.

Isaacs et al., J Immunol 161: 3862-3869 (1998).

Isenman et al., J Immunol 124: 326-331 (1980).

Ishii-Watabe, A. et al., "Molecular Design of Therapeutic Antibodies," Pharmaceutics 74 (1): 4-11: 17 pages (2014).

Israel et al, Immunology 89(4): 573-578 (1996).

Ito, N. et al., "Efficacy and safety of eculizumab in childhood atypical hemolytic uremic syndrome in Japan," Clin Exp Nephrol., vol. 20:265-272 (2016).

Ito, W. et al., "The His-probe method: effects of histidine residues introduced into the complementarity-determining regions of antibodies on antigen-antibody interactions at different pH values," FEBS Letter, vol. 309(1): 85-88(1992).

Jodele, S. et al., "Complement blockade for TA-TMA: lessons learned from a large pediatric cohort treated with eculizumab," Blood, American Society of Hematology, US, vol. 135 (13):1049-1057 (2020).

Johne et al., J Immunol Meth 160: 191-198 (1993).

Johnson et al., J Med Chem 42: 4640-4649 (1999).

Jones et al., Nature 321: 522-525 (1986).

Jonsson et al., Ann Biol Clin 51: 19-26 (1993).

Jonsson et al., Biotechniques 11: 620-627 (1991).

Junghans, R. et al., "The protection receptor for IgG catabolismis the beta2-microglobulin-containing neonatal intestinal transport receptor," PNAS, USA, vol. 93(11):512-5516 (1996).

Jungi and Pepys, Immunology 43(2): 271-279 (1981).

Kaszubska et al., Protein Expression and Purification 18: 213-220 (2000).

Kay et al., Human Gene Therapy 3: 641-647 (1992).

Kim et al., Ophthalmic Res 39: 244-254 (2007).

Kinstler et al., Advanced Drug Deliveries Reviews 54: 477-485.

Klein et al., Proc. Natl Acad Sci USA 78: 524-528 (1981).

Kroshus et al., Transplantation 60: 1194-1202 (1995).

Kulasekararaj A. G. et al., "Ravulizumab (ALXN1210) vs eculizumab in C5-inhibitor-experienced adult patients with PNH: the 302 study," Blood, vol. 133(6):540-549 (2019).

Kulasekararaj, A. et al., "Ravulizumab (ALXN1210) vs eculizumab in C5-inhibitor-experienced adult patients with PNH: the 302 study," Blood, vol. 133(6):540-549 (2009).

Lee J-W et al., "Ravulizumab (ALXN1210) vs eculizumab in adult patients with PNH naive to complement inhibitors: the 301 study," Blood, vol. 133 (6):530-539 (2019).

Lee, CV., et al., "High-affinity human antibodies from phage-displayed synthetic Fab libraries with a single framework scaffold," J. Molecular Biology, vol. 340 (5):1073-1093 (2004).

Lee, et al., Bioconjug Chem 10(6): 973-81 (1999).

Lee, J-W et al., "Results from a Phase 3, Multicenter, Noninferiority Study of Ravulizumab (ALXN1210) Versus Eculizumab In Adult Patients with Paroxysmal Nocturnal Hemoglobi-nuria (PNH) Naive to Complement Inhibitors," (2018), XP055550310, Retrieved from the Internet: URL:https://learningcenter.ehaweb.org/eha/2018/ stockholm/218885/jong.wook.lee.results.from.a.phase.3.multicenter.noninferiority.study.of.html?f=media=1 [retrieved on Jan. 31, 2019].

Lee, J-W et al., "Ravulizumab (ALXN1210) vs eculizumab in adult patients with PNH naive to complement inhibitors: the 301 study," Blood, (2018) ISSN: 0006-4971, DOI: 10.1182/blood-2018-09-876136.

Lee, J-W et al., "Ravulizumab (ALXN1210) vs eculizumab in adult patients with PNH naive to complement inhibitors: the 301 study", Blood, vol. 133 (6): 530-539 (2018).

Lee, J-W. et al., "2428 Immediate, Complete, and Sustained Inhibition of C5 with ALXN1210 Reduces Complement-Mediated Hemolysis in Patients with Paroxysmal Noctur-nal Hemoglobinuria (PNH): Interim Analysis of a Dose-Escalation Study," Internet Ci-tation, Dec. 4, 2016 (Dec. 4, 2016 ), XP002768543, Retrieved from the Internet: URL:https://ash.confex.com/ash/2016/webprogram/Paper90053.html [retrieved on Mar. 23, 2017] the whole document.

Legendre, CM, et al., "Terminal Complement Inhibitor Eculizumab in Atypical Hemolytic-Uremic Syndrome," N Engl J Med., vol. 368:2169-2181 (2013).

Levy and Ladda, Nat New Biol 229(2): 51-52 (1971).

Licht, C., et al., "The global aHUS registry: methodology and initial patient characteristics," BMC Nephrology, vol. 16 (207) 8 pages (2015) DOI 10.1186/s12882-015-0195-1.

Lodmell et al., Vaccine 18:1059-1066 (2000).

Loirat, C. et al., "Plasmatherapy in Atypical Hemolytic Uremic Syndrome," Seminars in Thrombosis and Hemostasis, vol. 36(6): 673-681 (2010).

Loirat, C. et al., "An international consensus approach to the management of atypical hemolytic uremic syndrome in children," Pediatr Nephrol., vol. 31:15-39 (2016).

Loirat, C. et al., "Atypical hemolytic uremic syndrome," Orphanet Journal of Rare Diseases, vol. 6:60: 30 pages (2011).

Lusky and Botchan, Nature 293: 79 (1981).

Magro C. et al., "Complement associated microvascular injury and thrombosis in the pathogenesis of severe COVID-19 infection: A report of five cases," Translational Research, vol. 220: 1-13 (2020).

Malina, M. et al., "Peripheral Gangrene in Children With Atypical Hemolytic Uremic Syndrome," Pediatrics, vol. 131: e331-e335 (2013).

Marks, W. H., et al., "Safety and efficacy of eculizumab in the prevention of antibody-mediated rejection in living-donor kidney transplant recipients requiring desensitization therapy: A randomized trial," American Journal of Transplantation, vol. 19 (10):2876-2888 (2019).

Mckeage K. "Ravulizumab: First Global Approval" Drugs, vol. 79(3) pp. 347-352 (2019).

Mckeage K., "Ravulizumab: First Global Approval," Rugs, vol. 79 (3): 347-352 (2019).

McLaughlin et al., J Virol 62: 1963-1973 (1989).

Medicus et al., J Exp Med 144: 1076-1093 (1976).

Mihu et al., J Gastrointestin Liver Dis 16(4): 419-424 (2007).

Moongkarndi et al, Immunobiol 165: 323 (1983).

Moongkarndi et al., Immunobiol 162: 397 (1982).

U.S. Appl. No. 17/289,150, filed Apr. 27, 2021, Andrew Denker.

A Phase 3, Randomized, Parallel-Group,Multicenter, Open-Label,Pharmacokinetic,Noninferiority Study of Ravulizumab Administered Subcutaneously Versus Intravenously in Adult Patients With Paroxysmal Nocturnal Hemoglobinuria Currently Treated With Eculizumab, EU Clinical Trials Register, Nov. 15, 2018 (Nov. 15, 2018), XP002797253, Retrieved from the Internet:URL:https://www.clinicaltrialsregister.eu/ctr-search/trial/2017-002370-39/DE [retrieved on Jan. 29, 2020], 6 pages.

Alexion Pharmaceuticals, Inc.Press Release, "FDA Accepts Priority Review of ALXN1210 as a Treatment for Patients with Paroxysmal Nocturnal Hemoglobinuria (PNH) in the US," Aug. 20, 2018, 3 pages.

Alexion Pharmaceuticals: "Efficacy and Safety Study of IV Ravulizumab in Patients With COVID-19 Severe Pneumonia: NCT04369469," Clinical Trials, Apr. 30, 2020, Retrieved from the Internet:URL:https://clinicaltrials.gov/ct2/show/NCT04369469 [retrieved on Jul. 6, 2021].

Alexion Pharmaceuticals: "Soliris (Eculizumab) Treatment of Participants With COVID-19 (NCT04355494)," Clinical Trials, Apr.

(56)            References Cited

OTHER PUBLICATIONS 21, 2020, Retrieved from the Internet: URL:https://clinicaltrials.gov/ct2/show/NCT04355494 [retrieved on Jul. 6, 2021].

Ambati and Adamis, Prog Retin Eye Res 21(2): 145-151 (2002).

Amsterdam et al., Am J Physiol 268: H448-H457 (1995).

Anonymous: "Alexion Receives FDA Approval for Ultomiris (ravulizumab-cwvz) for Atypical Hemolytic Uremic Syndrome (aHUS)," Oct. 18, 2019.

Anonymous: "Assessment report Soliris /Eculizumab," pp. 1-28, Mar. 21, 2013, Retrieved from the Internet:URL:https://www.ema.europa.eu/en/documents/variation-report/soliris-h-c-791-ii-0050-epar-assessment-report-variation_en.pdf [retrieved on Aug. 7, 2019].

Anonymous: "Ravulizumab for atypical haemolytic uraemic syndrome in adults and children—first line," Aug. 1, 2018, pp. 1-10.

Anonymous: "Single Arm Study of ALXN1210 in Complement Inhibitor Treatment-Naive Adult and Adolescent Patients With Atypical Hemolytic Uremic Syndrome (aHUS)," pp. 1-6 (2016) XP055619305,Retrieved from the Internet:URL:https://clinicaltrials.gov/ct2/show/NCTO2949128?term=alxn1210&rank=8 [retrieved on Sep. 6, 2019].

Anonymous: "Study of Ravulizumab in Children and Adolescents With Atypical Hemolytic Uremic Syndrome (aHUS)", Apr. 27, 2017 (Apr. 27, 2017), pp. 1-9, XP055619309,Retrieved from the Internet: URL:https://clinicaltrials.gov/ct2/show/NCTO3131219?term=alxn1210&rank=5 [retrieved on Sep. 6, 2019].

Appel et al., J Am Soc Nephrol 16: 1392-1404 (2005).

Armentano et al., Proc Natl Acad Sci USA 87: 6141-6145 (1990).

Baldridge et al., Methods 19: 103-107 (1999).

Barocas and Balachandran, Expert Opin Drug Delivery 5(1): 1-10 (10) (2008).

Baudino et al.I, J Immunol 181: 6664-6669 (2008).

Berge et al., J Phar4m Sci 66: 1-19 (1977).

Berkner et al., BioTechniques 6: 616 ( 1988).

Better et al., Science 240: 1041-1043 (1988).

Bieg et al., Autoimmunity 31(1): 15-24 (1999).

Bless et al., Am J Physiol 276(1): L57-L63 (1999).

Brodsky, R. et al., "Complement in hemolytic anemia," Blood, vol. 126(22):2459-2465 (2015).

Burmeister et al., Nature 372: 379-383 (1994).

Burton et al., Adv Immun 51:1-18 (1992).

Campistol, J., et al., "An update for atypical haemolytic uraemic syndrome: diagnosis and treatment. A consensus document," Nefrologia, vol. 33(1):27-45 (2013).

Canfield et al., J Exp Med 173: 1483-1491 (1991).

Caron et al., J Exp Med 176: 1191-1195 (1992).

Chaparro-Riggers, Biol Chem 287: 11090-11097 (2012).

Chothia et al., Nature 342: 877-883 (1989).

Chowdhury et al., Science 254: 1802-1805 (1991).

Christmann, M., et al., "Eculizumab as First-Line Therapy for Atypical Hemolytic Uremic Syndrome," Pediatrics, vol. 133, e1759: 7 pages (2014).

Co et al., Mol Immunol 30: 1361 (1993).

Co et al., Mol Immunol 30: 1361, 6 pages (1993).

Collins, A. et al., 146 Global Phase 3 Clinical Trials Assessing Efficacy and Safety of Ravulizumab in Adults and Children Who Developed Thrombotic Microangiopathy (TMA) After Hematopoietic Stem Cell Transplant (Hsct), American Journal of Kidney Diseases,Elsevier, Amsterdam, NL, vol. 77 (4):612-613 (2021).

Cooper et al., J Exp Med 132: 775-793 (1970).

Crocker et al., J Clin Pathol 27(2): 122-124 (1974).

Dai et al., Proc Natl Acad Sci USA 89: 10892-10895 (1992).

Dall'Acqua et al., J Biol Chem 281: 23514-23524 (2006).

Dall'Acqua et al., J Immunol 117: 1129-1138 (2006).

Danos and Mulligan, Proc Natl Acad Sci USA 85; 6460-6464 (1988).

Datta-Mannan et al., J Biol Chem 282(3): 1709-1717 (2007).

Daugherty, A., et al., "Formulation and delivery issues for monoclonal antibody thera-peutics," Current Trends in Monoclonal Antibody Development and Manufacture, Chapter 8:103-129 (2010).

Deans et al., Proc Natl Acad Sci USA 81: 1292 (1984).

Diurno, F. et al, "Eculizumab treatment in patients with COVID-19:preliminary results from real life ASL Napoli 2 Nord experience," European Review for Medical and Pharmacological Sciences, vol. 24 (7):4040-4047 (2020).

Dong et al, Reviews in Mol Biotech 82: 303-323 (2002).

Duncan and Winter Nature 322: 738-40 (1988).

Eglitis et al., Science 230: 1395-1398 (1985).

Emea, Souris scientific discussion, 41 pages (2007).

Eppstein et al., "Biological activity of liposome-encapsulated murine interferon gamma is mediated by a cell membrane receptor," Proc Natl Acad Sci USA 82: 3688-92 (1985).

Epstein et al., Proc Natl Acad Sci USA 82: 3688 (1985).

European Search Report, EP Application No. 161776562, dated Aug. 8, 2016, 8 pages.

Evans, et al., Mol Immunol 32(16): 1183-95 (1995).

Fakhouri, F. et al., "Terminal Complement Inhibitor Eculizumab in Adult Patients With Atypical Hemolytic Uremic Syndrome: A Single-Arm, Open-Label Trial," Am J Kidney Dis., vol. 68(1):84-93 (2016).

Fearon et al., J Exp Med 142: 856-863 (1975).

Ferry et al., Proc Natl Acad Sci USA 88: 8377-8381 (1991).

Fivash et al., Curr Opin Biotechnol 9: 97-101 (1998).

Flotte et al., Am J Respir Cell Mol Biol 7: 349-356 (1992).

Ghetie et al., Nat Biotech 15: 637-640 (1997).

Greenbaum, L. et al. "Eculizumab is a safe and effective treatment in pediatric patients with atypical hemolytic uremic syndrome" Kidney International, vol. 89: 701-711 (2016).

Gulsen and Chauhan, Invest Opthalmol Vis Sci 45: 2342-2347 (2004).

Gupta et al., Vaccine 13(14): 1263-1276 (1995).

Hanauske et al., Clin Cancer Res 13(2, part 1): 523-531 (2007).

Heinen, S. et al., "Monitoring and modeling treatment of atypical hemolytic uremic syndrome," Molecular Immunology, vol. 54: 84-88 (2013).

Hetherington et al., Antimicrobial Agents and Chemotherapy 50(10): 2499-2500 (2006).

Hezareh et al., J Virol 75: 12161-12168 (2001).

Hillmen et al., N. Engl J Med 350(6): 552-559 (2004).

Hillmen, P. et al., "Long-term safety and efficacy of sustained eculizumab treatment in patients with paroxysmal nocturnal haemoglobinuria," British Journal of Haematology doi:10.1111/bjh. 12347, 12 pages (2013).

Hinton et al., J Biol Chem 279: 6213-6216 (2004).

Hinton et al., J Immunol 176: 246-356 (2006).

Hirt-Minkowski , P. et al., "Atypical Hemolytic Uremic Syndrome: Update on the Complement System and What Is New," Nephron Clin Pract., 114:c219-c235 (2010).

History of Change for Study: NCT02949128: Single Arm Study of ALXN1210 in Complement Inhibitor Treatment-Naïve Adult and Adolescent Patients with Atypical Hemolytic Syndrome (aHUS); Study NCT02949128, Submitted Date: Oct. 27, 2016 (v1). (2016).

History of Changes for Study: NCT02949128 Single Arm Study of ALXN1210 in Complement Inhibitor Treatment-Naïve Adult and Adolescent Patients With Atypical Hemolytic Uremic Syndrome (aHUS), Nov. 17, 2022, 6 pages.

History of Changes for Study: NCT03131219 Study of ALXN1210 in Children and Adolescents With Atypical Hemolytic Uremic Syndrome (aHUS), Nov. 16, 2022, 4 pages.

Holers and Thurman, Molecular Immunology 41: 147-152 (2004).

Holers et al., Immunological Reviews 223: 300-316 (2008).

Homeister et al., J Immunol 150: 1055-1064 (1993).

Hou et al., Cytokine 10: 319-30 (1998).

Houdebine, Curr Opin Biotechnol 13(6): 625-629 (2002).

Huber et al., Proc Natl Acad Sci USA 88: 8039-8043 (1991).

Hudson and Kortt, J Immunol Methods 231: 177-189 (1999).

Huston et al., Methods in Enzymology 203: 46-88 (1991).

Hwang et al., Proc Natl Acad Sci USA 77: 4030 (1980).

Hwu et al., J Immunol 150: 4104-4115 (1993).

Igawa et al., "Antibody recycling by engineered pH-dependent antigen binding improves the duration of antigen neutralization," Nat. Biotechnol. 28(11):1203-1207 (2010).

International Preliminary Report on Patentability, PCT/US2019/058846, dated Apr. 27, 2020, 8 pages.

(56) References Cited

OTHER PUBLICATIONS

International Preliminary Report on Patentability, PCT/US2021/045823, dated Feb. 7, 2023, 8 pages.
International Preliminary Report on Patentability, PCT/U52018/044071, dated Jan. 28, 2020, 8 pages.
International Preliminary Report on Patentability, PCT/US2018/057760, dated Apr. 28, 2020 2019, 9 pages.
International Preliminary Report on Patentability, PCT/US2019/034293, dated Dec. 1, 2020, 9 pages.
International Preliminary Report on Patentability, PCT/US2019/034297, dated Dec. 8, 2020, 10 pages.
International Preliminary Report on Patentability, PCT/US2021/027636, dated Oct. 13, 2022, 11 pages.
International Preliminary Report on Patentability, PCT/US2021/031141, dated Dec. 13, 2022, 8 pages.
International Search Report and Written Opinion for Application No. PCT/US2015/019225, dated May 18, 2015.
International Search Report and Written Opinion, PCT/U52018/044071, dated Oct. 2, 2018, 12 pages.
International Search Report and Written Opinion, PCT/US2018/057760, dated Mar. 21, 2019, 13 pages.
International Search Report and Written Opinion, PCT/US2019/034293, dated Aug. 21, 2019, 14 pages.
International Search Report and Written Opinion, PCT/US2019/034297, dated Sep. 25, 2019, 13 pages.
International Search Report and Written Opinion, PCT/US2019/058846, dated Feb. 10, 2020, 14 pages.
International Search Report and Written Opinion, PCT/US2020/014998, dated Jun. 22, 2020, 13 pages.
International Search Report and Written Opinion, PCT/US2021/027636, dated Sep. 6, 2021, 17 pages.
Alexion Reports Second Quarter 2017 Results, 7 pages (2017).
Anonymous, "Highlights of Prescribing Information—Ultomiris (ravulizumab-cwvz) injection, for intravenous use Initial U.S. Approval: 2018", (63 pages Oct. 1, 2019), URL: Ultomiris (ravulizumab-cwvz) injection, for intravenous use Initial U.S. Approval: 2018.
Anonymous, "Recipe: Sodium phosphate", doi:10.1101/PDB.REC8303, ISSN 1559-6095, 1 page, Cold Spring Harbor Protocols, URL: http://cshprotocols.cshlp.org/content/2006/1/pdb.rec8303.full?text_only=true.

Caravaca-Fontan, F. et al., "Update on C3 Glomerulopathy: A Complement-Mediated Disease," Nephron, vol. 144 (6):272-280 (2020).
Cleland, J. et al., "The development of stable protein formulations: a close look at protein aggregation, deamidation, and oxidation," Critical Reviews in Therapeutic Drug Carriers Systems, vol. 10(4):307-377 (1993).
ClinicalTrials.gov, ALXN1210 Versus Eculizurnab in Adult Participants With Paroxysmal Nocturnal Hemoglobinuria (PNH) Currently Treated With Eculizumab, NCT03056040, 19 pages (2017).
Dall' Acqua, W. et al., "Increasing the Affinity of a Human IgG1 for the Neonatal Fc-Receptor: Biological Consequences," The Journal of Immunology, vol. 169:5171-5180 (2002).
Datta-Manna, A. et al., "Humanized IgG1 Variants with Differential Binding Properties to the Neonatal Fc Receptor: Relationship to Pharmacokinetics in Mice and Primates," Drug Metabolism and Disposition, vol. 35 (1): 86-94 (2007).
International Preliminary Report on Patentability, PCT/US2019/039557, dated Dec. 29, 2020, 8 pages.
International Preliminary Report on Patentability, PCT/US2020/058779, dated May 10, 2022, 12 pages.
International Search Report and Written Opinion, PCT/US2019/039557, dated Oct. 11, 2019, 12 pages.
International Search Report and Wrtten Opinion, PCT/US2020/058779, dated Feb. 18, 2021, 16 pages.
Janda A., et al., "Ig Constant Regions Effects on Variable Region Structure and Function," Frontiers in Microbiology, vol. 7 (22): 10 pages. doi:10.3389/fmicb.2016.00022 (2016).
Kuo, T. et al., Neonatal Fc Receptor and IgG-based therapeutics, mabs, vol. 3(5):422-30 (2011).
Liu et al., "Recovery and purification process development for monoclonal antibody production," mAbs, vol. 2 (5):480-489 (2010).
Presta, L. et al., "Molecular engineering and design of therapeutic antibodies," vol. 20(4):460-70 (2008).
Yeung, Y. et al., "Engineering human IgG1 affinity to human neonatal Fc receptor: impact of affinity improvement on pharmacokinetics in primates," J. Immunol., vol. 182 (12):7663-7671 (2009).

* cited by examiner

FIG. 1

FACIT Fatigue Scale (Version 4)

Below is a list of statements that other people with your illness have said are important. Please circle or mark one number per line to indicate your response as it applies to the past 7 days.

| | | Not At All | A Little Bit | Somewhat | Quite a Bit | Very Much |
|---|---|---|---|---|---|---|
| 1 | I feel fatigued | 0 | 1 | 2 | 3 | 4 |
| 2 | I feel weak all over | 0 | 1 | 2 | 3 | 4 |
| 3 | I feel listless ("washed out") | 0 | 1 | 2 | 3 | 4 |
| 4 | I feel tired | 0 | 1 | 2 | 3 | 4 |
| 5 | I have trouble starting things because I am tired | 0 | 1 | 2 | 3 | 4 |
| 6 | I have trouble finishing things because I am tired | 0 | 1 | 2 | 3 | 4 |
| 7 | I have energy | 0 | 1 | 2 | 3 | 4 |
| 8 | I am able to do my usual activities | 0 | 1 | 2 | 3 | 4 |
| 9 | I need to sleep during the day | 0 | 1 | 2 | 3 | 4 |
| 10 | I am too tired to eat | 0 | 1 | 2 | 3 | 4 |
| 11 | I need help doing my usual activities | 0 | 1 | 2 | 3 | 4 |
| 12 | I am frustrated by being too tired to do the things I want to do | 0 | 1 | 2 | 3 | 4 |
| 13 | I have to limit my social activity because I am tired | 0 | 1 | 2 | 3 | 4 |

FIG. 2A

EORTC QLQ-C30 (version 3)

We are interested in some things about you and your health. Please answer all of the questions yourself by circling the number that best applies to you. There are no "right" or "wrong" answers. The information that you provide will remain strictly confidential.

Please fill in your initials:

Your birthdate (Day, Month, Year):

Today's date (Day, Month, Year):

| | | Not at All | A Little | Quite a Bit | Very Much |
|---|---|---|---|---|---|
| 1. | Do you have any trouble doing strenuous activities, like carrying a heavy shopping bag or a suitcase? | 1 | 2 | 3 | 4 |
| 2. | Do you have any trouble taking a <u>long</u> walk? | 1 | 2 | 3 | 4 |
| 3. | Do you have any trouble taking a <u>short</u> walk outside of the house? | 1 | 2 | 3 | 4 |
| 4. | Do you need to stay in bed or a chair during the day? | 1 | 2 | 3 | 4 |
| 5. | Do you need help with eating, dressing, washing yourself or using the toilet? | 1 | 2 | 3 | 4 |

During the past week:

| | | Not at All | A Little | Quite a Bit | Very Much |
|---|---|---|---|---|---|
| 6. | Were you limited in doing either your work or other daily activities? | 1 | 2 | 3 | 4 |
| 7. | Were you limited in pursuing your hobbies or other leisure time activities? | 1 | 2 | 3 | 4 |
| 8. | Were you short of breath? | 1 | 2 | 3 | 4 |
| 9. | Have you had pain? | 1 | 2 | 3 | 4 |
| 10. | Did you need to rest? | 1 | 2 | 3 | 4 |
| 11. | Have you had trouble sleeping? | 1 | 2 | 3 | 4 |
| 12. | Have you felt weak? | 1 | 2 | 3 | 4 |
| 13. | Have you lacked appetite? | 1 | 2 | 3 | 4 |
| 14. | Have you felt nauseated? | 1 | 2 | 3 | 4 |
| 15. | Have you vomited? | 1 | 2 | 3 | 4 |
| 16. | Have you been constipated? | 1 | 2 | 3 | 4 |

Please go on to the next page

FIG. 2B

| During the past week: | Not at All | A Little | Quite a Bit | Very Much |
|---|---|---|---|---|
| 17. Have you had diarrhea? | 1 | 2 | 3 | 4 |
| 18. Were you tired? | 1 | 2 | 3 | 4 |
| 19. Did pain interfere with your daily activities? | 1 | 2 | 3 | 4 |
| 20. Have you had difficulty in concentrating on things, like reading a newspaper or watching television? | 1 | 2 | 3 | 4 |
| 21. Did you feel tense? | 1 | 2 | 3 | 4 |
| 22. Did you worry? | 1 | 2 | 3 | 4 |
| 23. Did you feel irritable? | 1 | 2 | 3 | 4 |
| 24. Did you feel depressed? | 1 | 2 | 3 | 4 |
| 25. Have you had difficulty remembering things? | 1 | 2 | 3 | 4 |
| 26. Has your physical condition or medical treatment interfered with your family life? | 1 | 2 | 3 | 4 |
| 27. Has your physical condition or medical treatment interfered with your social activities? | 1 | 2 | 3 | 4 |
| 28. Has your physical condition or medical treatment caused you financial difficulties? | 1 | 2 | 3 | 4 |

For the following questions please circle the number between 1 and 7 that best applies to you

29.   How would you rate your overall health during the past week?

1       2       3       4       5       6       7

Very poor                                          Excellent

30.   How would you rate your overall quality of life during the past week?

1       2       3       4       5       6       7

Very poor                                          Excellent

FIG. 3

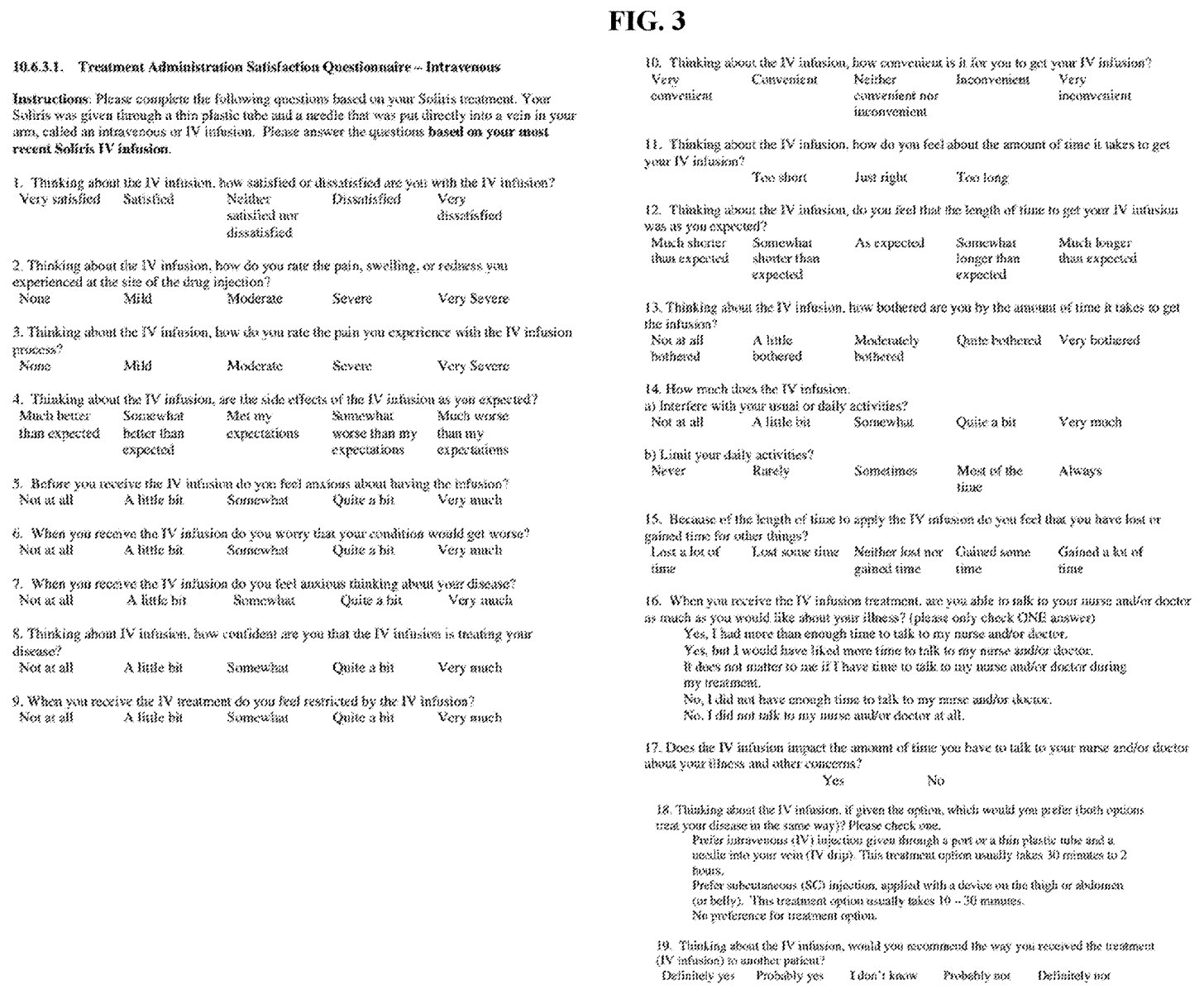

10.6.3.1. Treatment Administration Satisfaction Questionnaire – Intravenous

Instructions: Please complete the following questions based on your Soliris treatment. Your Soliris was given through a thin plastic tube and a needle that was put directly into a vein in your arm, called an intravenous or IV infusion. Please answer the questions based on your most recent Soliris IV infusion.

1. Thinking about the IV infusion, how satisfied or dissatisfied are you with the IV infusion?
Very satisfied   Satisfied   Neither satisfied nor dissatisfied   Dissatisfied   Very dissatisfied 2. Thinking about the IV infusion, how do you rate the pain, swelling, or redness you experienced at the site of the drug injection?
None   Mild   Moderate   Severe   Very Severe 3. Thinking about the IV infusion, how do you rate the pain you experience with the IV infusion process?
None   Mild   Moderate   Severe   Very Severe 4. Thinking about the IV infusion, are the side effects of the IV infusion as you expected?
Much better than expected   Somewhat better than expected   Met my expectations   Somewhat worse than my expectations   Much worse than my expectations 5. Before you receive the IV infusion do you feel anxious about having the infusion?
Not at all   A little bit   Somewhat   Quite a bit   Very much 6. When you receive the IV infusion do you worry that your condition would get worse?
Not at all   A little bit   Somewhat   Quite a bit   Very much 7. When you receive the IV infusion do you feel anxious thinking about your disease?
Not at all   A little bit   Somewhat   Quite a bit   Very much 8. Thinking about IV infusion, how confident are you that the IV infusion is treating your disease?
Not at all   A little bit   Somewhat   Quite a bit   Very much 9. When you receive the IV treatment do you feel restricted by the IV infusion?
Not at all   A little bit   Somewhat   Quite a bit   Very much 10. Thinking about the IV infusion, how convenient is it for you to get your IV infusion?
Very convenient   Convenient   Neither convenient nor inconvenient   Inconvenient   Very inconvenient 11. Thinking about the IV infusion, how do you feel about the amount of time it takes to get your IV infusion?
Too short   Just right   Too long 12. Thinking about the IV infusion, do you feel that the length of time to get your IV infusion was as you expected?
Much shorter than expected   Somewhat shorter than expected   As expected   Somewhat longer than expected   Much longer than expected 13. Thinking about the IV infusion, how bothered are you by the amount of time it takes to get the infusion?
Not at all bothered   A little bothered   Moderately bothered   Quite bothered   Very bothered 14. How much does the IV infusion:
a) Interfere with your usual or daily activities?
Not at all   A little bit   Somewhat   Quite a bit   Very much
b) Limit your daily activities?
Never   Rarely   Sometimes   Most of the time   Always 15. Because of the length of time to apply the IV infusion do you feel that you have lost or gained time for other things?
Lost a lot of time   Lost some time   Neither lost nor gained time   Gained some time   Gained a lot of time 16. When you receive the IV infusion treatment, are you able to talk to your nurse and/or doctor as much as you would like about your illness? (please only check ONE answer)
Yes, I had more than enough time to talk to my nurse and/or doctor.
Yes, but I would have liked more time to talk to my nurse and/or doctor.
It does not matter to me if I have time to talk to my nurse and/or doctor during my treatment.
No, I did not have enough time to talk to my nurse and/or doctor.
No, I did not talk to my nurse and/or doctor at all.

17. Does the IV infusion impact the amount of time you have to talk to your nurse and/or doctor about your illness and other concerns?
Yes   No 18. Thinking about the IV infusion, if given the option, which would you prefer (both options treat your disease in the same way)? Please check one.
Prefer intravenous (IV) infusion given through a part or a thin plastic tube and a needle into your vein (IV drip). This treatment option usually takes 30 minutes to 2 hours.
Prefer subcutaneous (SC) injection, applied with a device on the thigh or abdomen (or belly). This treatment option usually takes 10 – 30 minutes.
No preference for treatment option.

19. Thinking about the IV infusion, would you recommend the way you received the treatment (IV infusion) to another patient?
Definitely yes   Probably yes   I don't know   Probably not   Definitely not

FIG. 4

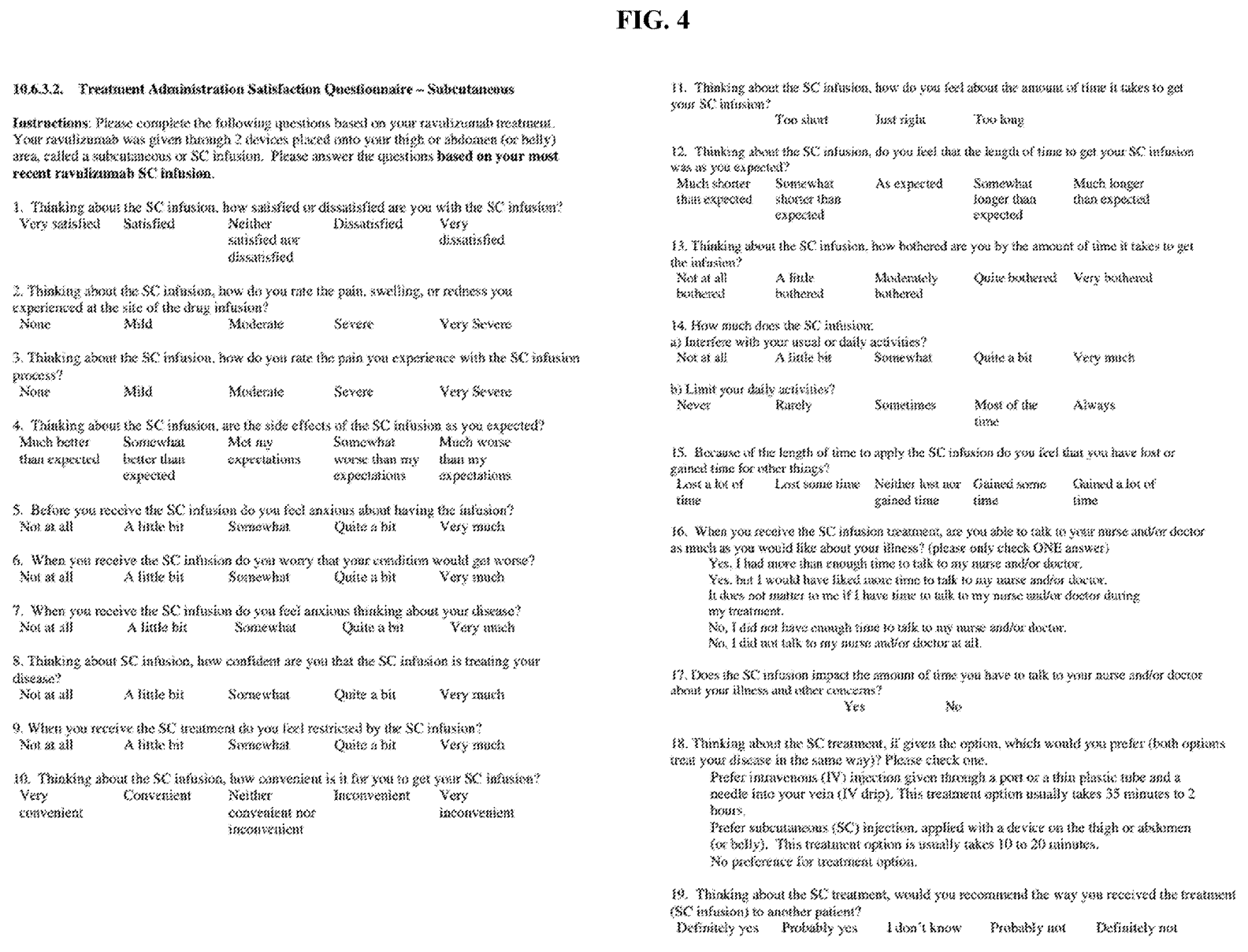

10.6.3.2.    Treatment Administration Satisfaction Questionnaire ~ Subcutaneous

Instructions: Please complete the following questions based on your ravulizumab treatment.
Your ravulizumab was given through 2 devices placed into your thigh or abdomen (or belly) area, called a subcutaneous or SC infusion. Please answer the questions based on your most recent SC infusion.

1. Thinking about the SC infusion, how satisfied or dissatisfied are you with the SC infusion?
Very satisfied   Satisfied   Neither satisfied nor dissatisfied   Dissatisfied   Very dissatisfied 2. Thinking about the SC infusion, how do you rate the pain, swelling, or redness you experienced at the site of the drug infusion?
None   Mild   Moderate   Severe   Very Severe 3. Thinking about the SC infusion, how do you rate the pain you experience with the SC infusion process?
None   Mild   Moderate   Severe   Very Severe 4. Thinking about the SC infusion, are the side effects of the SC infusion as you expected?
Much better than expected   Somewhat better than expected   Met my expectations   Somewhat worse than my expectations   Much worse than my expectations 5. Before you receive the SC infusion do you feel anxious about having the infusion?
Not at all   A little bit   Somewhat   Quite a bit   Very much 6. When you receive the SC infusion do you worry that your condition would get worse?
Not at all   A little bit   Somewhat   Quite a bit   Very much 7. When you receive the SC infusion do you feel anxious thinking about your disease?
Not at all   A little bit   Somewhat   Quite a bit   Very much 8. Thinking about SC infusion, how confident are you that the SC infusion is treating your disease?
Not at all   A little bit   Somewhat   Quite a bit   Very much 9. When you receive the SC treatment do you feel restricted by the SC infusion?
Not at all   A little bit   Somewhat   Quite a bit   Very much 10. Thinking about the SC infusion, how convenient is it for you to get your SC infusion?
Very convenient   Convenient   Neither convenient nor inconvenient   Inconvenient   Very inconvenient 11. Thinking about the SC infusion, how do you feel about the amount of time it takes to get your SC infusion?
Too short   Just right   Too long 12. Thinking about the SC infusion, do you feel that the length of time to get your SC infusion was as you expected?
Much shorter than expected   Somewhat shorter than expected   As expected   Somewhat longer than expected   Much longer than expected 13. Thinking about the SC infusion, how bothered are you by the amount of time it takes to get the infusion?
Not at all bothered   A little bothered   Moderately bothered   Quite bothered   Very bothered 14. How much does the SC infusion:
a) Interfere with your usual or daily activities?
Not at all   A little bit   Somewhat   Quite a bit   Very much
b) Limit your daily activities?
Never   Rarely   Sometimes   Most of the time   Always 15. Because of the length of time to apply the SC infusion do you feel you have lost or gained time for other things?
Lost a lot of time   Lost some time   Neither lost nor gained time   Gained some time   Gained a lot of time 16. When you receive the SC infusion treatment, are you able to talk to your nurse and/or doctor as much as you would like about your illness? (please only check ONE answer)
Yes, I had more than enough time to talk to my nurse and/or doctor.
Yes, but I would have liked more time to talk to my nurse and/or doctor.
It does not matter to me if I have time to talk to my nurse and/or doctor during my treatment.
No, I did not have enough time to talk to my nurse and/or doctor.
No, I did not talk to my nurse and/or doctor at all.

17. Does the SC infusion impact the amount of time you have to talk to your nurse and/or doctor about your illness and other concerns?
Yes   No 18. Thinking about the SC treatment, if given the option, which would you prefer (both options treat your disease in the same way)? Please check one.
Prefer intravenous (IV) injection given through a port or a thin plastic tube and a needle into your vein (IV drip). This treatment option usually takes 35 minutes to 2 hours.
Prefer subcutaneous (SC) injection, applied with a device on the thigh or abdomen (or belly). This treatment option is usually takes 10 to 20 minutes.
No preference for treatment option.

19. Thinking about the SC treatment, would you recommend the way you received the treatment (SC infusion) to another patient?
Definitely yes   Probably yes   I don't know   Probably not   Definitely not

FIG. 6

Randomized and received first ALXN1210 Dose

Modified Safety Set
(SC = 90 and IV = 46)

Patients from site 0657 excluded due to source document PD
(SC = 6 and IV = 1)

Safety Set and FAS
(SC = 84 and IV = 45)

Discontinued [1]
(SC = 0 and IV = 1)

Completed Randomized Treatment Period
(SC = 84 and IV = 44)

Excluded from PK Analysis Set [2]
(SC = 20 and IV = 3)

Included in PK Analysis Set
(SC= 70 and IV = 43)

Notes
(1) Withdrawal by patient at Day 59
(2) Exclusions due to protocol deviations (15), inexact dosing (9)

FIG. 7A

DEMOGRAPHICS AND BASELINE CHARACTERISTICS (FAS)

| Variable | Ravulizumab IV (N=45) | Ravulizumab SC (N=84) | Total (N=129) |
|---|---|---|---|
| Sex, n (%) | | | |
| Male | 20 (44.4) | 40 (47.6) | 60 (46.5) |
| | | | |
| Race, n (%) | | | |
| White | 29 (64.4) | 63 (75.0) | 92 (71.3) |
| Not Reported | 6 (13.3) | 13 (15.5) | 19 (14.7) |
| Black or African American | 4 (8.9) | 3 (3.6) | 7 (5.4) |
| Asian | 2 (4.4) | 0 | 2 (1.6) |
| Unknown or other | 3 (6.6) | 5 (6.0) | 8 (6.2) |
| American Indian or Alaska Native | 1 (2.2) | 0 | 1 (0.8) |
| | | | |
| Age (years) at Informed Consent | | | |
| n | 45 | 84 | 129 |
| Mean (SD) | 46.4 (13.22) | 45.3 (14.47) | 45.7 (14.00) |
| Median | 44.0 | 42.5 | 44.0 |
| Min, Max | 24, 77 | 18, 79 | 18, 79 |

FIG. 7B

DEMOGRAPHICS AND BASELINE CHARACTERISTICS (FAS) [CON'T]

| Variable | Ravulizumab IV (N=45) | Ravulizumab SC (N=84) | Total (N=129) |
|---|---|---|---|
| Age (years) at Informed Consent Category, n (%) | | | |
| 18 to 65 years | 41 (91.1) | 75 (89.3) | 116 (89.9) |
| >65 years | 4 (8.9) | 9 (10.7) | 13 (10.1) |
| Baseline Weight (kg) | | | |
| n | 45 | 84 | 129 |
| Mean (SD) | 73.68 (12.655) | 72.52 (12.611) | 72.92 (12.589) |
| Median | 73.00 | 72.15 | 72.30 |
| Min, Max | 52.0, 98.4 | 43.5, 98.0 | 43.5, 98.4 |
| Baseline Weight (kg) Category, n (%) | | | |
| ≥ 40 kg to < 60 kg | 8 (17.8) | 13 (15.5) | 21 (16.3) |
| ≥ 60 kg to < 100 kg | 37 (82.2) | 71 (84.5) | 108 (83.7) |

FIG. 8

PRIMARY PK NONINFERIORITY ANALYSIS

| $C_{trough}$ (µg/mL) | Ravulizumab IV (N=43) | | | Ravulizumab SC (N=70) | | | Ratio of Geometric Least Squares Means (SC/IV) | 90% CI for Ratio | z-score | p-value |
|---|---|---|---|---|---|---|---|---|---|---|
| | Geometric LSM | SE | n | Geometric LSM | SE | n | | | | |
| Stage 1 | 476.85 | 1.066 | 17 | 560.69 | 1.053 | 33 | 1.176 | (1.046, 1.322) | 5.526 | |
| Stage 2 | 468.43 | 1.060 | 26 | 627.80 | 1.054 | 37 | 1.340 | (1.197, 1.500) | 7.640 | |
| Weighted overall result | | | | | | | 1.257 | (1.160, 1.361) | 9.310 | <.0001 |

Note: SE = Standard Error; LSM = Least Squares Mean; CI = Confidence Interval.

Note: The Stage 1 population are all patients included in the sample size re-estimation analysis. The Stage 2 population are all patients not analyzed as part of the sample size re-estimation analysis.

Note: A mixed model was performed on log-transformed parameters and includes treatment and stratified weight group as fixed effects.

Note: Geometric least square means are the least square means from the mixed model after back transformation to the original scale.

Note: The 90% confidence interval is presented after back transformation to the original scale.

Note: The z-score is calculated at each stage and shown as a combined score using the pre-specified weights of .5 and .5. Statistical significance is reached if the weighted overall z-score is > 1.645.

FIG. 9

FOREST PLOT: PK NONINFERIORITY

SERUM RAVULIZUMAB CONCENTRATION: MEAN (±SD)

FIG. 11

FREE C5 CONCENTRATION

LACTATE DEHYDROGENASE: MEAN (±SD)

FIG. 13

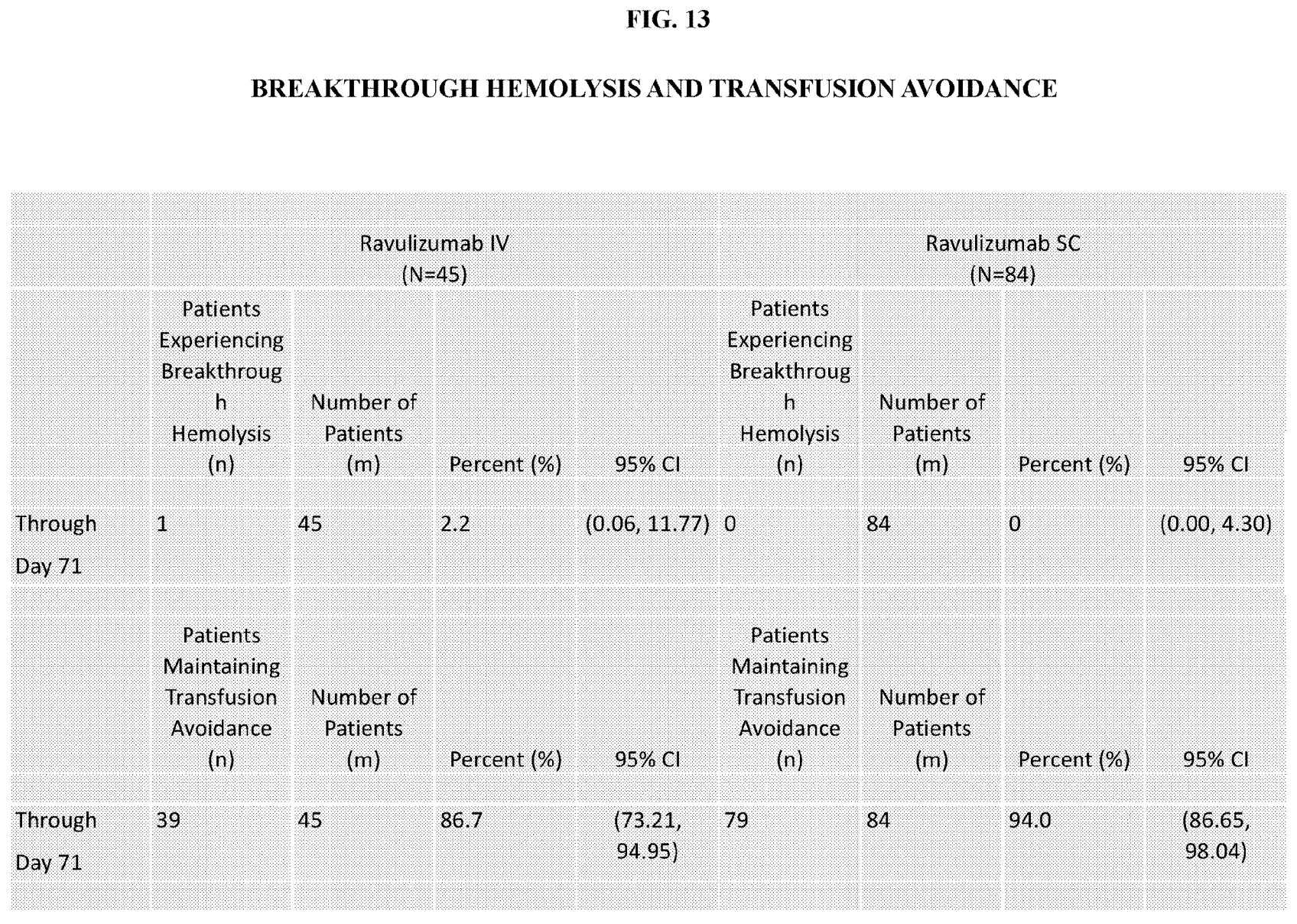

BREAKTHROUGH HEMOLYSIS AND TRANSFUSION AVOIDANCE

| | Ravulizumab IV (N=45) | | | Ravulizumab SC (N=84) | | |
|---|---|---|---|---|---|---|
| | Patients Experiencing Breakthrough Hemolysis (n) | Number of Patients (m) | Percent (%) | 95% CI | Patients Experiencing Breakthrough Hemolysis (n) | Number of Patients (m) | Percent (%) | 95% CI |
| Through Day 71 | 1 | 45 | 2.2 | (0.06, 11.77) | 0 | 84 | 0 | (0.00, 4.30) |

| | Patients Maintaining Transfusion Avoidance (n) | Number of Patients (m) | Percent (%) | 95% CI | Patients Maintaining Transfusion Avoidance (n) | Number of Patients (m) | Percent (%) | 95% CI |
|---|---|---|---|---|---|---|---|---|
| Through Day 71 | 39 | 45 | 86.7 | (73.21, 94.95) | 79 | 84 | 94.0 | (86.65, 98.04) |

FIG. 14

HEMOGLOBIN STABILITY AND PNH SYMPTOMATOLOGY

| | Ravulizumab IV (N=45) | | | Ravulizumab SC (N=84) | | |
|---|---|---|---|---|---|---|
| Patients Maintaining Stabilized Hemoglobin | Patients Maintaining Stabilized Hemoglobin (n) | Number of Patients (m) | Percent (%) | 95% CI | Patients Maintaining Stabilized Hemoglobin (n) | Number of Patients (m) | Percent (%) | 95% CI |

| | Patients Maintaining Stabilized Hemoglobin (n) | Number of Patients (m) | Percent (%) | 95% CI | Patients Maintaining Stabilized Hemoglobin (n) | Number of Patients (m) | Percent (%) | 95% CI |
|---|---|---|---|---|---|---|---|---|
| Through Day 71 | 36 | 44 | 81.8 | (67.29, 91.81) | 73 | 78 | 93.6 | (85.67, 97.89) |

| | Patients Showing Symptoms of PNH (n) | Number of Patients (m) | Percent (%) | 95% CI | Patients Showing Symptoms of PNH (n) | Number of Patients (m) | Percent (%) | 95% CI |
|---|---|---|---|---|---|---|---|---|
| Through Day 71 | 21 | 45 | 46.7 | (31.66, 62.13) | 38 | 84 | 45.2 | (34.34, 56.48) |

FIG. 15

TREATMENT EMERGENT AE OVERVIEW

|  | Ravulizumab IV (N=45) | | Ravulizumab SC (N=84) | | Total (N=129) | |
|---|---|---|---|---|---|---|
|  | n (%) | E | n (%) | E | n (%) | E |
| Any Treatment Emergent Adverse Event (TEAE) | 27 (60.0) | 70 | 67 (79.8) | 284 | 94 (72.9) | 354 |
| Any Treatment Emergent Serious TEAE (TESAE) | 1 (2.2) | 1 | 5 (6.0) | 5 | 6 (4.7) | 6 |
| TESAE Leading to Withdrawal of Study Drug | 0 | 0 | 0 | 0 | 0 | 0 |
| TEAE Leading to Withdrawal of Study Drug | 0 | 0 | 0 | 0 | 0 | 0 |
| Any Adverse Device Effect (ADE) | NA | NA | 38 (45.2) | 107 | NA | NA |
| Administration site conditions |  |  | 22 (26.2) | 76 |  |  |
| Device Use |  |  | 20 (23.8) | 31 |  |  |
| Any Serious ADE (SADE) | NA | NA | 0 | 0 | NA | NA |
| Death | 0 | 0 | 0 | 0 | 0 | 0 |
| TEAEs Not Associated with Device/Device Use | 27 (60.0) | 70 | 54 (64.3) | 177 | 81 (62.8) | 247 |

FIG. 16

SERIOUS ADVERSE EVENTS

| Preferred Term (PT) | Ravulizumab IV (N=45) | | Ravulizumab SC (N=84) | | Total (N=129) | |
|---|---|---|---|---|---|---|
| | n (%) | E | n (%) | E | n (%) | E |
| Patients with Treatment Emergent Serious Adverse Events | 1 (2.2) | 1 | 5 (6.0) | 5 | 6 (4.7) | 6 |
| Neutropenia | 0 | 0 | 1 (1.2) | 1 | 1 (0.8) | 1 |
| Lens dislocation | 0 | 0 | 1 (1.2) | 1 | 1 (0.8) | 1 |
| Cholecystitis | 1 (2.2) | 1 | 0 | 0 | 1 (0.8) | 1 |
| Gastroenteritis | 0 | 0 | 1 (1.2) | 1 | 1 (0.8) | 1 |
| Cervicobrachial syndrome | 0 | 0 | 1 (1.2) | 1 | 1 (0.8) | 1 |
| Urinary retention | 0 | 0 | 1 (1.2) | 1 | 1 (0.8) | 1 |

SUBCUTANEOUS (SC) ADMINISTRATION OF ANTI-C5 ANTIBODIES FOR TREATMENT OF COMPLEMENT-ASSOCIATED CONDITIONS

CROSS REFERENCE TO RELATED APPLICATIONS

This application is the U.S. National Phase Application of PCT/US2021/031141, filed on May 6, 2021, and claims priority to, and the benefit of, U.S. Provisional Application No. 63/043,613, filed on Jun. 24, 2020, the entire contents which are incorporated herein by reference.

SEQUENCE LISTING

The instant application contains a Sequence Listing which has been submitted electronically in ASCII format and is hereby incorporated by reference in its entirety. Said ASCII copy, created on Apr. 28, 2021, is named 0633_WO_SL.txt and is 58,818 bytes in size.

BACKGROUND

The complement system acts in conjunction with other immunological systems of the body to defend against intrusion of cellular and viral pathogens. There are at least 25 complement proteins, which are found as a complex collection of plasma proteins and membrane cofactors. The plasma proteins make up about 10% of the globulins in vertebrate serum. Complement components achieve their immune defensive functions by interacting in a series of intricate but precise enzymatic cleavage and membrane binding events. The resulting complement cascade leads to the production of products with opsonic, immunoregulatory, and lytic functions. A concise summary of the biologic activities associated with complement activation is provided, for example, in The Merck Manual, 16th Edition.

While a properly functioning complement system provides a robust defense against infecting microbes, inappropriate regulation or activation of the complement pathways has been implicated in the pathogenesis of a variety of disorders, including paroxysmal nocturnal hemoglobinuria (PNH). PNH is an ultra-rare disorder driven by chronic uncontrolled complement activation. The resulting inflammation and cellular damage lead to the devastating clinical manifestations of this disease.

PNH is a condition in which uncontrolled complement activity leads to systemic complications, principally through intravascular hemolysis and platelet activation (see Socié G, et al., French Society of Haematology. Lancet. 1996; 348 (9027):573-577 and Brodsky, R., Blood. 2014; 124(18): 2804-2811). Persistent intravascular hemolysis may be triggered by various stressors, such as infection or physical exertion, which leads to smooth muscle contraction (free hemoglobin), chronic anemia, and an increased risk of severe thromboembolism. Thromboembolism, as the most common cause of mortality in patents with PNH, may lead to pulmonary hypertension and end-organ damage of vital organs, such as the liver, kidneys, brain, and intestines (Hillmen, P., et al, Am. J. Hematol. 2010; 85(8):553-559). Due to these adverse pathologic processes, patients with PNH have a decreased quality of life (QoL), which may include debilitating fatigue, chronic pain, poor physical function, shortness of breath, abdominal pain, erectile dysfunction, a need for anticoagulation, blood transfusions and in some instances, a need for dialysis (Weitz, I C., et al., Thromb Res. 2012; 130(3):361-368).

Patients with PNH are at a substantial risk of morbidity and mortality. Accordingly, it is an object of the present invention to provide improved methods for treating patients with PNH.

SUMMARY

This instant application is based, in part, on the data obtained from a Phase 3, randomized, open-label, parallel-group, multicenter study evaluating subcutaneous ravulizumab (ULTOMIRIS® SC) compared with intravenous ravulizumab (ULTOMIRIS® IV) in the treatment of paroxysmal nocturnal hemoglobinuria (PNH).

As described herein, subcutaneous ravulizumab (ULTOMIRIS® SC) can be administered, for example, using drug delivery devices to treat a variety of complement-mediated disorders, including, but not limited to PNH, atypical hemolytic uremic syndrome (aHUS), generalized myasthenia gravis (gMG), neuromyelitis optica spectrum disorder (NMOSD), hematopoietic stem cell transplant-associated thrombotic microangiopathy (HSCT-TMA), amyotrophic lateral sclerosis (ALS), complement mediated thrombotic microangiopathy (CM-TMA), preeclampsia hemolysis, elevated liver enzymes, low platelet count (PE-HELLP), pregnancy-induced aHUS (p-aHUS), particularly, PNH and aHUS.

PNH is a serious ultra-rare blood disorder characterized by the destruction of red blood cells. Chronic hemolysis due to PNH may result in the formation of blood clots, which can occur in blood vessels throughout the body, damage vital organs, and potentially lead to premature death. Atypical HUS occurs when the complement system over-responds, leading the body to attack its own healthy cells. aHUS can cause progressive injury to vital organs, primarily the kidneys, via damage to the walls of blood vessels and blood clots. aHUS may lead to sudden organ failure or a slow loss of function over time—potentially resulting in the need for a transplant, and in some cases, death. It affects both adults and children, and many patients present in critical condition, often requiring supportive care, including dialysis, in an intensive care unit. The prognosis of aHUS can be poor in many cases, so a timely and accurate diagnosis—in addition to treatment—is critical to improving patient outcomes. aHUS can be differentiated from other hemolytic diseases via clinical tests.

In the instant study examining ULTOMIRIS® SC in the therapy of PNH, 136 adult patients who are clinically stable and have previously been treated with SOLIRIS® (eculizumab) for at least three months prior to study entry were enrolled. A primary objective of the study was to assess pharmacokinetic non-inferiority of ULTOMIRIS® SC compared with ULTOMIRIS® IV, as assessed by ULTOMIRIS® serum trough concentration at Day 71. Various secondary endpoints, including safety, immunogenicity and various pharmacokinetic/pharmacodynamic (PK/PD), quality of life, device performance and efficacy measures, are also evaluated on an ongoing basis.

Patients were stratified by weight groups (≥40 to <60 kg and ≥60 to <100 kg) and then randomized 2:1 to receive either ULTOMIRIS® SC or ULTOMIRIS® IV. All patients received an initial IV loading dose on Day 1, and on Day 15, patients in the ULTOMIRIS® SC group began receiving a once-weekly self-administered fixed-dose of ULTOMIRIS® SC, and patients in the ULTOMIRIS IV group received a single infusion of the approved weight-based IV dose.

The study met its primary endpoint, with ULTOMIRIS® SC demonstrating PK-based non-inferiority versus ULTOMIRIS® IV at Day 71, based on serum ravulizumab trough concentration–$C_{trough}$). For instance, using a geometric least-squared mean (g-LSM) analysis of $C_{trough}$ levels, it was found that patients on ULTOMIRIS SC had higher $C_{trough}$ levels than patients on ULTOMIRIS® IV (ratio of g-LSM in SC/g-LSM in IV of about 1.257). These data show that delivery of ULTOMIRIS® using the systems of and devices of the instant application provides superior PK profile in vivo compared to traditional intravenous method of delivery.

In comparative assessment of C5 marker levels, along with analysis of efficacy endpoints such as LDH levels, breakthrough hemolysis and transfusion avoidance, hemoglobin stability and PNH symptomology, it was found that the profile of patients on ULTOMIRIS® SC was comparable, if not better than, patients on ULTOMIRIS® IV. To this end, in relation to C5 inhibition, in both IV and SC groups, results obtained after the first dose through the randomized treatment period were ≤0.5 μg/mL; the defined threshold for complete terminal complement inhibition. SC dosing resulted in ravulizumab exposures ≥175 μg/mL, defined as threshold for complete complement inhibition, for all subjects with no unexpected PK findings. With respect to efficacy endpoints, (a) breakthrough hemolysis low in both arm, with no events in SC group; (b) transfusion avoidance was maintained in 94% and 87% of SC and IV groups, respectively; (c) stable hemoglobin results maintained in 94% and 82% of SC and IV groups, respectively; and (d) symptom of PNH observed in 45% and 47% of SC and IV groups, respectively.

Furthermore, preliminary safety data through the 71-day randomized treatment period of the study was consistent with the known safety profile of ULTOMIRIS® and did not result in any unexpected safety findings. Administration site reactions were reported in 26% of the patients in the SC treatment arm.

All but one participant completed the randomized controlled treatment portion of the study and chose to continue in the ongoing open-label extension period, where all patients will receive weekly ULTOMIRIS® SC for up to an additional 182 weeks. The extension period will provide 12 months of safety data for regulatory submissions.

The disclosure relates to the following non-limiting embodiments:

In some embodiments, the disclosure relates to a method of treating a human patient with a complement-associated condition, the method comprising administering to the patient during an administration cycle an effective amount of an anti-C5 antibody or antigen binding fragment thereof, comprising CDR1, CDR2 and CDR3 heavy chain sequences as set forth in SEQ ID NOs:19, 18 and 3, respectively, and CDR1, CDR2 and CDR3 light chain sequences as set forth in SEQ ID NOs:4, 5 and 6, respectively, wherein the anti-C5 antibody or antigen binding fragment thereof is administered subcutaneously (SC).

In some embodiments, the disclosure relates to a method of treating a human patient with a complement-associated condition according to the foregoing or following, wherein the anti-C5 antibody or antigen binding fragment thereof is administered subcutaneously with a device, e.g., an on-body delivery system (OBDS), comprising the effective amount of the anti-C5 antibody, e.g., ravulizumab or eculizumab or a biosimilar antibody thereof.

In some embodiments, the disclosure relates to a method of treating a human patient with a complement-associated condition according to the foregoing or following, wherein the anti-C5 antibody or antigen binding fragment thereof is administered every week thereafter at a dose of 490 mg.

In some embodiments, the disclosure relates to a method of treating a human patient with a complement-associated condition according to the foregoing or following, wherein the human patient receives an intravenous loading dose prior to subcutaneous administration.

In some embodiments, the disclosure relates to a method of treating a human patient with a complement-associated condition according to the foregoing or following, wherein the loading dose is weight-based, wherein (i) a dose of 2400 mg is administered to a patient weighing ≥40 to <60 kg, or (ii) a dose of 2700 mg is administered to a patient weighing ≥60 to <100 kg.

In some embodiments, the disclosure relates to a method of treating a human patient with a complement-associated condition according to the foregoing or following, wherein the anti-C5 antibody or antigen binding fragment thereof further comprises a variant human Fc constant region that binds to human neonatal Fc receptor (FcRn), wherein the variant human Fc CH3 constant region comprises Met-429-Leu and Asn-435-Ser substitutions at residues corresponding to methionine 428 and asparagine 434 of a native human IgG Fc constant region, each in EU numbering.

In some embodiments, the disclosure relates to a method of treating a human patient with a complement-associated condition according to the foregoing or following, wherein the anti-C5 antibody or antigen binding fragment thereof is administered subcutaneously on Day 15 of the administration cycle and for at least seven weeks thereafter at a dose of 490 mg qlw.

In some embodiments, the disclosure relates to a method of treating a human patient with a complement-associated condition according to the foregoing or following, wherein the administration cycle is a total of 10 weeks of treatment.

In some embodiments, the disclosure relates to a method of treating a human patient with a complement-associated condition according to the foregoing or following, wherein the anti-C5 antibody or antigen binding fragment thereof is administered subcutaneously at a dose of 490 mg q1w for up to 3 months, 6 months, 9 months, 12 months, 15 months, 18 months, 21 months, two years or chronically for the remainder of the patient's life.

In some embodiments, the disclosure relates to a method of treating a human patient with a complement-associated condition according to the foregoing or following, wherein the patient has previously been treated with eculizumab.

In some embodiments, the disclosure relates to a method of treating a human patient with a complement-associated condition according to the foregoing or following, wherein the administration cycle starts at least two weeks after the patient's last dose of eculizumab.

In some embodiments, the disclosure relates to a method of treating a human patient with a complement-associated condition according to the foregoing or following, wherein the anti-C5 antibody or antigen-binding fragment thereof, comprises a heavy chain variable region of SEQ ID NO:12 and a light chain variable region of SEQ ID NO:8.

In some embodiments, the disclosure relates to a method of treating a human patient with a complement-associated condition according to the foregoing or following, wherein the anti-C5 antibody or antigen-binding fragment thereof, further comprises a heavy chain constant region of SEQ ID NO:13.

In some embodiments, the disclosure relates to a method of treating a human patient with a complement-associated condition according to the foregoing or following, wherein the antibody or antigen-binding fragment thereof, comprises a heavy chain polypeptide comprising the amino acid sequence of SEQ ID NO:14 and a light chain polypeptide comprising the amino acid sequence of SEQ ID NO:11.

In some embodiments, the disclosure relates to a method of treating a human patient with a complement-associated condition according to the foregoing or following, wherein the anti-C5 antibody or antigen binding fragment thereof, binds to human C5 at pH 7.4 and 25° C. with an affinity dissociation constant ($K_D$) that is in the range 0.1 nM$\leq$$K_D$$\leq$1 nM.

In some embodiments, the disclosure relates to a method of treating a human patient with a complement-associated condition according to the foregoing or following, wherein the anti-C5 antibody or antigen binding fragment thereof, binds to human C5 at pH 6.0 and 25° C. with a $K_D$$\geq$10 nM.

In some embodiments, the disclosure relates to a method of treating a human patient with a complement-associated condition according to the foregoing or following, wherein the treatment maintains a serum trough concentration of the anti-C5 antibody or antigen binding fragment thereof, of 100 μg/mL or greater during the administration cycle.

In some embodiments, the disclosure relates to a method of treating a human patient with a complement-associated condition according to the foregoing or following, wherein the complement-associated disorder is selected from the group consisting of atypical hemolytic uremic syndrome (aHUS), complement mediated thrombotic microangiopathy (CM-TMA), paroxysmal nocturnal hemoglobinuria (PNH), neuromyelitis optica spectrum disorder (NMOSD), hematopoietic stem cell transplant-associated thrombotic microangiopathy (HSCT-TMA), amyotrophic lateral sclerosis (ALS), preeclampsia hemolysis, elevated liver enzymes, low platelet count (PE-HELLP), pregnancy-induced aHUS (p-aHUS), generalized myasthenia gravis (gMG), dermatomyositis, Guillain-Barre syndrome (GBS).

In some embodiments, the disclosure relates to a method of treating a human patient with a complement-associated condition according to the foregoing or following, wherein the treatment results in terminal complement inhibition or a reduction of hemolysis as assessed by lactate dehydrogenase (LDH) levels.

In some embodiments, the disclosure relates to a method of treating a human patient with a complement-associated condition according to the foregoing or following, wherein the treatment produces at least one therapeutic effect selected from the group consisting of: a reduction or cessation in fatigue, abdominal pain, dyspnea, anemia, dysphagia, chest pain, and erectile dysfunction.

In some embodiments, the disclosure relates to a method of treating a human patient with a complement-associated condition according to the foregoing or following, wherein the treatment produces a shift toward normal levels of a hemolysis-related hematologic biomarker selected from the group consisting of: free hemoglobin, haptoglobin, reticulocyte count, PNH red blood cell (RBC) clone and D-dimer.

In some embodiments, the disclosure relates to a method of treating a human patient with a complement-associated condition according to the foregoing or following, wherein the treatment produces a shift toward normal levels of a chronic disease associated biomarker selected from the group consisting of estimated glomerular filtration rate (eGFR) and spot urine:albumin:creatinine and plasma brain natriuretic peptide (BNP).

In some embodiments, the disclosure relates to a method of treating a human patient with a complement-associated condition according to the foregoing or following, wherein the treatment produces a reduction in the need for blood transfusions and/or major adverse vascular events (MAVEs).

In some embodiments, the disclosure relates to a method of treating a human patient with a complement-associated condition according to the foregoing or following, wherein the treatment produces a change from Baseline in quality of life, assessed via the Functional Assessment of Chronic Illness Therapy (FACIT)-Fatigue Scale, version 4, and the European Organization for Research and Treatment of Cancer, Quality of Life Questionnaire-Core 30 Scale.

In some embodiments, the disclosure relates to a method of treating a human patient with a complement-associated condition according to the foregoing or following, wherein the anti-C5 antibody or antigen binding fragment thereof, is administered subcutaneously using an on-body delivery system (OBDS); preferably, wherein the OBDS comprises a SMARTDOSE Gen I delivery platform; more preferably, wherein the OBDS comprises a pharmaceutical formulation comprising ravulizumab (70 mg/mL) in 50 mM sodium phosphate, 25 mM arginine, 5% sucrose, 0.05% polysorbate 80, and water for injection.

In some embodiments, the disclosure relates to a method of treating a human patient with a complement-associated condition according to the foregoing or following, wherein the subcutaneous administration provides a serum ravulizumab trough concentration (Ctrough) of about 200 μg/ml to about 1000 μg/ml; preferably about 400 μg/ml to about 800 μg/ml; particularly from about 550 μg/ml to about 650 μg/ml.

In some embodiments, the disclosure relates to a method of treating a human patient with a complement-associated condition according to the foregoing or following, wherein the effective amount of the subcutaneous administration provides an increased serum ravulizumab trough concentration (Ctrough) compared to an intravenous formulation comprising ravulizumab; preferably wherein the increase in Ctrough is about 5% to about 50%, preferably about 15% to about 35%.

In some embodiments, the disclosure relates to a method of treating a human patient with a complement-associated condition according to the foregoing or following, wherein the subcutaneous administration attenuates free C5 levels in the patient; preferably, wherein the free C5 level is attenuated below the defined threshold for complete terminal complement inhibition, e.g., $\leq$0.5 μg/ml, in the treated patient.

In some embodiments, the disclosure relates to a method of treating a human patient with a complement-associated condition according to the foregoing or following, wherein the subcutaneous administration provides a threshold level of ravulizumab for complete complement inhibition, e.g., an in vivo ravulizumab level of $\geq$175 μg/ml, in the patient.

In some embodiments, the disclosure relates to a method of treating a human patient with a complement-associated condition according to the foregoing or following, wherein the effective amount of the SC administration (a) attenuates breakthrough hemolysis in the patient; (b) provides transfusion avoidance in the patient; (c) stabilizes hemoglobin levels in the patient; (d) lowers at least one symptom of PNH in the patient.

In some embodiments, the disclosure relates to a method of treating a human patient with a complement-associated condition according to the foregoing or following, wherein the anti-C5 antibody or the antigen-binding fragment thereof is administered in a 5-9 minute injection.

In some embodiments, the disclosure relates to a method of treating a human patient with a complement-associated condition according to the foregoing or following, wherein the anti-C5 antibody or the antigen-binding fragment thereof is administered with a single or tandem subcutaneous (SC) device; preferably with a tandem device.

In some embodiments, the disclosure relates to a method of treating a human patient with a complement-associated condition according to the foregoing or following, wherein the anti-C5 antibody or the antigen-binding fragment thereof is administered at a constant flow rate, e.g., via a plurality of electromechanical pins.

In some embodiments, the disclosure relates to a method of treating a human patient with a complement-associated condition according to the foregoing or following, wherein the patient is an adult patient between 40 kg and 100 kg.

In some embodiments, the disclosure relates to a device for subcutaneous administration of an anti-C5 antibody or antigen binding fragment thereof for treating a complement-mediated condition, comprising: (a) an on-body delivery system (OBDS); and (b) a subcutaneous (SC) formulation of the anti-C5 antibody or antigen binding fragment thereof.

In some embodiments, the disclosure relates to a device for treating a complement-mediated condition according to the foregoing or following, wherein the OBDS comprises a SMARTDOSE Gen I delivery platform In some embodiments, the disclosure relates to a device for treating a complement-mediated condition according to the foregoing or following, wherein the subcutaneous formulation of the anti-C5 antibody or antigen binding fragment thereof comprises ravulizumab (70 mg/mL) in 50 mM sodium phosphate, 25 mM arginine, 5% sucrose, 0.05% polysorbate 80, and water for injection In some embodiments, the disclosure relates to a device for treating a complement-mediated condition according to the foregoing or following, wherein the device delivers a dose of 490 mg to a human patient over a period of one week.

In some embodiments, the disclosure relates to a device, particularly an on-body delivery system (OBDS), comprising an effective amount of a subcutaneous (SC) formulation for treating a complement mediated condition, wherein the SC formulation comprises an anti-C5 antibody, e.g., ravulizumab or eculizumab or a biosimilar antibody thereof, or an antigen-binding fragment of the anti-C5 antibody; particularly wherein the SC formulation comprises ravulizumab.

In some embodiments, the disclosure relates to an on-body delivery system (OBDS) for treating a complement-mediated condition according to the foregoing or following, which comprises (a) an injector for delivery of the anti-C5 antibody (Platform), (b) a prefilled cartridge comprising the anti-C5 antibody (PFC) appended to the Platform; and (c) a telescopic screw assembly (TSA). In some embodiments, the PFC comprises about 3.5 ml ravulizumab at a concentration of about 70 mg/ml.

In some embodiments, the disclosure relates to a kit for treating a complement associated disease or disorder, the kit comprising: (a) a device according to any one of the foregoing devices, e.g., an on-body delivery system (OBDS); and (b) instructions for using the device for subcutaneous administration of the anti-C5 antibody or an antigen-binding fragment thereof to a patient, e.g., human patient.

Provided herein are compositions and methods for treating a complement-associated condition (e.g., PNH) in a human patient, comprising administering to the patient an anti-C5 antibody, or antigen binding fragment thereof, wherein the anti-C5 antibody, or antigen binding fragment thereof, is administered (or is for administration) subcutaneously according to a particular clinical dosage regimen (i.e., at a particular dose amount and according to a specific dosing schedule). In one embodiment, the patient has previously been treated with eculizumab (SOLIRIS®) or ravulizumab (ULTOMIRIS®); particularly intravenously administered SOLIRIS® or ULTOMIRIS®. In some embodiments, the patient is treatment naïve, particularly, naïve to treatment with an anti-C5 antibody, e.g., (SOLIRIS®) or ravulizumab (ULTOMIRIS®) or a biosimilar antibody thereof.

An exemplary anti-C5 antibody is ravulizumab (also known as ULTOMIRIS®, ALXN1210 and antibody BNJ441) comprising the heavy and light chains having the sequences shown in SEQ ID NOs:14 and 11, respectively, or antigen binding fragments and variants thereof. In other embodiments, the antibody comprises the heavy and light chain complementarity determining regions (CDRs) or variable regions (VRs) of ravulizumab. Accordingly, in one embodiment, the antibody comprises the CDR1, CDR2, and CDR3 domains of the heavy chain variable (VH) region of ravulizumab having the sequence shown in SEQ ID NO:12, and the CDR1, CDR2 and CDR3 domains of the light chain variable (VL) region of ravulizumab having the sequence shown in SEQ ID NO:8. In another embodiment, the antibody comprises CDR1, CDR2 and CDR3 heavy chain sequences as set forth in SEQ ID NOs:19, 18, and 3, respectively, and CDR1, CDR2 and CDR3 light chain sequences as set forth in SEQ ID NOs:4, 5, and 6, respectively.

In another embodiment, the antibody comprises VH and VL regions having the amino acid sequences set forth in SEQ ID NO: 12 and SEQ ID NO: 8, respectively. In another embodiment, the antibody comprises a heavy chain constant region as set forth in SEQ ID NO:13. In another embodiment, the antibody comprises a heavy chain polypeptide as set forth in SEQ ID NO:14 and a light chain polypeptide as set forth in SEQ ID NO:11. In another embodiment, the antibody comprises a variant human Fc constant region that binds to human neonatal Fc receptor (FcRn), wherein the variant human Fc CH3 constant region comprises Met-429-Leu and Asn-435-Ser substitutions at residues corresponding to methionine 428 and asparagine 434 of a native human IgG Fc constant region, each in EU numbering.

In another embodiment, the antibody comprises CDR1, CDR2 and CDR3 heavy chain sequences as set forth in SEQ ID NOs:19, 18, and 3, respectively, and CDR1, CDR2 and CDR3 light chain sequences as set forth in SEQ ID NOs:4, 5, and 6, respectively, and a variant human Fc constant region that binds to human neonatal Fc receptor (FcRn), wherein the variant human Fc CH3 constant region comprises Met-429-Leu and Asn-435-Ser substitutions at residues corresponding to methionine 428 and asparagine 434 of a native human IgG Fc constant region, each in EU numbering.

In another embodiment, the antibody competes for binding with, and/or binds to the same epitope on C5 as the above-mentioned antibodies. In another embodiment, the antibody has at least about 90% variable region amino acid sequence identity with the above-mentioned antibodies (e.g., at least about 90%, 95% or 99% variable region identity with SEQ ID NO:12 and SEQ ID NO:8).

In another embodiment, the antibody binds to human C5 at pH 7.4 and 25° C. with an affinity dissociation constant ($K_D$) that is in the range 0.1 nM$\leq$$K_D$$\leq$1 nM. In another embodiment, the antibody binds to human C5 at pH 6.0 and 25° C. with a $K_D \geq 10$ nM. In yet another embodiment, the [($K_D$ of the antibody or antigen-binding fragment thereof for human C5 at pH 6.0 and at 25° C.)/($K_D$ of the antibody or antigen-binding fragment thereof for human C5 at pH 7.4 and at 25° C.)] of the antibody is greater than 25.

Exemplary complement-associated conditions that can be treated according to the methods described herein include, but are not limited to, rheumatoid arthritis, antiphospholipid antibody syndrome, lupus nephritis, ischemia-reperfusion injury, atypical hemolytic uremic syndrome (aHUS), typical hemolytic uremic syndrome, paroxysmal nocturnal hemoglobinuria (PNH), dense deposit disease, neuromyelitis optica spectrum disorder (NMOSD), hematopoietic stem cell transplant-associated thrombotic microangiopathy (HSCT-TMA), amyotrophic lateral sclerosis (ALS), complement mediated thrombotic microangiopathy (CM-TMA), preeclampsia hemolysis, elevated liver enzymes, low platelet count (PE-HELLP), pregnancy-induced aHUS (p-aHUS), multifocal motor neuropathy, multiple sclerosis, macular degeneration, HELLP syndrome, spontaneous fetal loss, thrombotic thrombocytopenic purpura, Pauci-immune vasculitis, epidermolysis bullosa, recurrent fetal loss, traumatic brain injury, myocarditis, a cerebrovascular disorder, a peripheral vascular disorder, a renovascular disorder, a mesenteric/enteric vascular disorder, vasculitis, Henoch-Schonlein purpura nephritis, systemic lupus erythematosus-associated vasculitis, vasculitis associated with rheumatoid arthritis, immune complex vasculitis, Takayasu's disease, dilated cardiomyopathy, diabetic angiopathy, Kawasaki's disease, venous gas embolus, restenosis following stent placement, rotational atherectomy, percutaneous transluminal coronary angioplasty, generalized myasthenia gravis (gMG), cold agglutinin disease, dermatomyositis, paroxysmal cold hemoglobinuria, antiphospholipid syndrome, Graves' disease, atherosclerosis, Alzheimer's disease, systemic inflammatory response sepsis, septic shock, spinal cord injury, glomerulonephritis, transplant rejection, Hashimoto's thyroiditis, type I diabetes, psoriasis, pemphigus, autoimmune hemolytic anemia, idiopathic thrombocytopenic purpura, Goodpasture's syndrome, Degos disease, catastrophic antiphospholipid syndrome, and severe acute respiratory syndrome coronavirus 2 (also known as "SARS-CoV-2", "COVID-19", and "coronavirus"). In a particular embodiment, the complement-associated condition is atypical hemolytic uremic syndrome (aHUS). In another particular embodiment, the complement-associated condition is paroxysmal nocturnal hemoglobinuria (PNH).

In one aspect, methods of subcutaneously administering an anti-C5 antibody, or antigen binding fragment thereof (e.g., ravulizumab) to a patient (e.g., a PNH patient) at a dose of between 400 mg-600 mg are provided. In one embodiment, the anti-C5 antibody, or antigen binding fragment thereof, is administered subcutaneously to a patient at a dose of between 450-550 mg. In another embodiment, the anti-C5 antibody, or antigen binding fragment thereof, is administered subcutaneously to a patient at a dose of about 400 mg, 405 mg, 410 mg, 420 mg, 425 mg, 430 mg, 435 mg, 440 mg, 445 mg, 450 mg, 455 mg, 460 mg, 465 mg, 470 mg, 475 mg, 480 mg, 485 mg, 490 mg, 495 mg, 500 mg, 505 mg, 510 mg, 515 mg, 520 mg, 525 mg, 530 mg, 535 mg, 540 mg, 545 mg, 550 mg, 555 mg, 560 mg, 565 mg, 570 mg, 575 mg, 580 mg, 585 mg, 590 mg, 595 mg, or 600 mg. In another embodiment, the anti-C5 antibody, or antigen binding fragment thereof, is administered subcutaneously to a patient at a dose of or about 490 mg.

In another embodiment, the anti-C5 antibody, or antigen binding fragment thereof, is administered subcutaneously to a patient (e.g., a PNH patient) at a dose of or about 490 mg once every week (e.g., for two weeks, three weeks, one month, two months, three months, four months, five months, six months, seven months, eight months, nine months, ten months, eleven months, 1 year, 2 years, 3 years, or chronically, e.g., for the remainder of the patient's life).

In another aspect, methods of treating patients having a complement-associated condition (e.g., PNH) are provided, wherein the patient is intravenously administered an initial dose (e.g., a loading dose) of an anti-C5 antibody, or antigen binding fragment thereof (e.g., ravulizumab), followed by subcutaneous administration of the anti-C5 antibody, or antigen binding fragment thereof (e.g., two weeks later). In one embodiment, the intravenous dose of the anti-C5 antibody, or antigen binding fragment thereof, is based on the patient's weight. For example, in one embodiment, a patient weighing ≥40 to <60 kg is intravenously administered 2400 mg of the anti-C5 antibody, or antigen binding fragment thereof, prior to being treated subcutaneously with the anti-C5 antibody, or antigen binding fragment thereof. In another embodiment, a patient weighing ≥60 to <100 kg is intravenously administered 2700 mg of the anti-C5 antibody, or antigen binding fragment thereof, prior to being treated subcutaneously with the anti-C5 antibody, or antigen binding fragment thereof.

In another embodiment, a patient is administered a subcutaneous administration of the anti-C5 antibody, or antigen binding fragment thereof, (e.g., at a dose of 490 mg) once a week (e.g., for two weeks, three weeks, one month, two months, three months, four months, five months, six months, seven months, eight months, nine months, ten months, eleven months, 1 year, 2 years, 3 years, or chronically, e.g., for the remainder of the patient's life).

In another embodiment, a patient is intravenously administered a dose (e.g., 2400 mg or 2700 mg) of an anti-C5 antibody, or antigen binding fragment thereof, on Day 1 of an administration cycle, followed by subcutaneous administration of the anti-C5 antibody, or antigen binding fragment thereof, (e.g., at a dose of 490 mg) on Day 15 of the administration cycle and every week thereafter (e.g., for two weeks, three weeks, one month, two months, three months, four months, five months, six months, seven months, eight months, nine months, ten months, eleven months, 1 year, 2 years, 3 years, or chronically, e.g., for the remainder of the patient's life).

In another embodiment, a method of treating a human patient with a complement-associated condition (e.g., PNH) is provided, the method comprising administering to the patient during an administration cycle an effective amount of an anti-C5 antibody, or antigen binding fragment thereof, wherein the anti-C5 antibody, or antigen binding fragment thereof, is administered:

(a) intravenously once on Day 1 of the administration cycle at a dose of:
 i. 2400 mg to a patient weighing ≥40 to <60 kg, or
 ii. 2700 mg to a patient weighing ≥60 to <100 kg; and
(b) subcutaneously on Day 15 of the administration cycle and every week thereafter at a dose of 490 mg.

In another embodiment, the anti-C5 antibody, or antigen binding fragment thereof, is administered to a patient weighing ≥40 to <60 kg: (a) intravenously once on Day 1 of the administration cycle at a dose of 2400 mg; and (b) subcutaneously on Day 15 of the administration cycle and every week thereafter at a dose of 490 mg.

In another embodiment, the anti-C5 antibody, or antigen binding fragment thereof, is administered to a patient weighing ≥60 to <100 kg: (a) intravenously once on Day 1 of the administration cycle at a dose of 2700 mg; and (b) subcutaneously on Day 15 of the administration cycle and every week thereafter at a dose of 490 mg.

In another embodiment, a method of treating a human patient with a complement-associated condition (e.g., PNH) is provided, the method comprising administering to the patient during an administration cycle an effective amount of an anti-C5 antibody, or antigen binding fragment thereof, comprising CDR1, CDR2, and CDR3 heavy chain sequences as set forth in SEQ ID NOs:19, 18, and 3, respectively, and CDR1, CDR2, and CDR3 light chain sequences as set forth in SEQ ID NOs:4, 5, and 6, respectively, wherein the anti-C5 antibody, or antigen binding fragment thereof, is administered:

(a) intravenously once on Day 1 of the administration cycle at a dose of:
        i. 2400 mg to a patient weighing ≥40 to <60 kg, or
        ii. 2700 mg to a patient weighing ≥60 to <100 kg; and
    (b) subcutaneously on Day 15 of the administration cycle and every week thereafter at a dose of 490 mg.

In another embodiment, a method of treating a human patient with a complement-associated condition (e.g., PNH), is provided, the method comprising administering to the patient during an administration cycle an effective amount of an anti-C5 antibody, or antigen binding fragment thereof, comprising CDR1, CDR2, and CDR3 heavy chain sequences as set forth in SEQ ID NOs:19, 18, and 3, respectively, CDR1, CDR2, and CDR3 light chain sequences as set forth in SEQ ID NOs:4, 5, and 6, respectively, and a variant human Fc constant region that binds to human neonatal Fc receptor (FcRn), wherein the variant human Fc CH3 constant region comprises Met-429-Leu and Asn-435-Ser substitutions at residues corresponding to methionine 428 and asparagine 434 of a native human IgG Fc constant region, each in EU numbering, wherein the anti-C5 antibody, or antigen binding fragment thereof, is administered:

(a) intravenously on Day 1 of the administration cycle at a dose of:
        i. 2400 mg to a patient weighing ≥40 to <60 kg, or
        ii. 2700 mg to a patient weighing ≥60 to <100 kg; and
    (b) subcutaneously on Day 15 of the administration cycle and every week thereafter at a dose of 490 mg.

In one embodiment, the anti-C5 antibody, or antigen binding fragment thereof, (e.g., ravulizumab) is formulated for intravenous administration (e.g., as an initial loading dose). For example, in one embodiment, the formulation for intravenous administration comprises 300 mg of ravulizumab (10 mg/mL) in 10 mM sodium phosphate, 150 mM sodium chloride, 0.02% polysorbate 80, and water for injection. In another embodiment, the formulation for intravenous administration consists of 300 mg of ravulizumab (10 mg/mL) in 10 mM sodium phosphate, 150 mM sodium chloride, 0.02% polysorbate 80, and water for injection. In another embodiment, ravulizumab for intravenous administration is formulated as a concentrated, sterile, preservative-free aqueous solution (10 mg/mL) in single-use 30 mL vials.

In one embodiment, the anti-C5 antibody, or antigen binding fragment thereof, (e.g., ravulizumab) is formulated for subcutaneous administration. For example, in one embodiment, the formulation for subcutaneous administration comprises 262.5 mg ravulizumab (70 mg/mL) in 50 mM sodium phosphate, 25 mM arginine, 5% sucrose, 0.05% polysorbate 80, and water for injection. In another embodiment, the formulation for subcutaneous administration consists of 262.5 mg ravulizumab (70 mg/mL) in 50 mM sodium phosphate, 25 mM arginine, 5% sucrose, 0.05% polysorbate 80, and water for injection. In another embodiment, the formulation for subcutaneous administration comprises 245 mg ravulizumab (70 mg/mL) in 50 mM sodium phosphate, 25 mM arginine, 5% sucrose, 0.05% polysorbate 80, and water for injection. In another embodiment, the formulation for subcutaneous administration consists of 245 mg ravulizumab (70 mg/mL) in 50 mM sodium phosphate, 25 mM arginine, 5% sucrose, 0.05% polysorbate 80, and water for injection. In another embodiment, ravulizumab for subcutaneous administration is formulated at a pH of 7.4.

Subcutaneous administration of an anti-C5 antibody, or antigen binding fragment thereof, (e.g., ravulizumab) according to the methods described herein can be accomplished by any suitable means. In addition, the anti-C5 antibody, or antigen binding fragment thereof, can be administered subcutaneously by a medical professional or self-administered. In one embodiment, the anti-C5 antibody, or antigen binding fragment thereof, is administered subcutaneously using an on-body delivery system (OBDS). In one embodiment, ravulizumab for subcutaneous administration is supplied in 3.5 mL single-use cartridges. In another embodiment, each cartridge of ravulizumab for subcutaneous administration contains 262.5 mg ravulizumab (70 mg/mL) in 50 mM sodium phosphate, 25 mM arginine, 5% sucrose, 0.05% polysorbate 80, and water for injection. In another embodiment, each cartridge of ravulizumab for subcutaneous administration contains 245 mg ravulizumab (70 mg/mL) in 50 mM sodium phosphate, 25 mM arginine, 5% sucrose, 0.05% polysorbate 80, and water for injection. In another embodiment, ravulizumab for subcutaneous administration is formulated as a concentrated, sterile, preservative-free aqueous solution (70 mg/mL) in a single-use, 3.5 mL prefilled cartridge designed for use in a single-use on-body delivery system. In one embodiment, the OBDS is the SmartDose® Drug Delivery Platform. In another embodiment, the ravulizumab is administered by subcutaneous injection via the single-use OBDS using the West SmartDose® Gen. I 3.5 mL.

In one embodiment, an administration cycle is 10 total weeks of treatment. In another embodiment, the anti-C5 antibody, or antigen binding fragment thereof, is administered subcutaneously at a dose of 490 mg once weekly after the administration cycle for up to 3 months, 6 months, 9 months, 12 months, 15 months, 18 months, 21 months, two years, or chronically, e.g., for the remainder of the patient's life. In some embodiments, the patients treated according to the methods described herein have previously been treated with a complement inhibitor. In one embodiment, the patient has previously been treated with eculizumab. In another embodiment, the patient has previously been treated for at least 1 month, at least 2 months, at least 3 months, at least 4 months, at least 5 months, at least 6 months, at least 7 months, at least 8 months, at least 9 months, at least 10 months, at least 11 months, at least 12 months, at least 18 months, or at least 24 months with eculizumab. In a particular embodiment, the patient has previously been treated for at least 6 months with eculizumab. In another embodiment, the patient has previously been treated with eculizumab at a dose of 900 mg every 2 weeks. In another embodiment, the treatment starts at least two weeks after the patient's last dose of eculizumab.

In some embodiments, the patients treated according to the methods described herein have been vaccinated against meningococcal infections within 3 years prior to, or at the time of, initiating treatment. In one embodiment, patients who received treatment less than 2 weeks after receiving a meningococcal vaccine are also treated with appropriate prophylactic antibiotics until 2 weeks after vaccination. In another embodiment, patients treated according to the methods described herein are vaccinated against meningococcal serotypes A, C, Y, W135, and/or B.

In another aspect, the treatment regimens described herein are sufficient to maintain particular serum trough concentrations of the anti-C5 antibody, or antigen binding fragment thereof. For example, in one embodiment, the treatment maintains a serum trough concentration of the anti-C5 antibody, or antigen binding fragment thereof, of 50, 55, 60, 65, 70, 75, 80, 85, 90, 95, 100, 105, 110, 115, 120, 125, 130, 135, 140, 145, 150, 155, 160, 165, 170, 175, 180, 185, 190, 200, 205, 210, 215, 220, 225, 230, 240, 245, 250, 255, 260, 265, 270, 280, 290, 300, 305, 310, 315, 320, 325, 330, 335, 340, 345, 350, 355, 360, 365, 370, 375, 380, 385, 390, 395, or 400 µg/ml or greater. In another embodiment, the treatment maintains a serum trough concentration of the anti-C5 antibody, or antigen binding fragment thereof, of 100 µg/ml or greater. In another embodiment, the treatment maintains a serum trough concentration of the anti-C5 antibody, or antigen binding fragment thereof, of 150 µg/ml or greater. In another embodiment, the treatment maintains a serum trough concentration of the anti-C5 antibody, or antigen binding fragment thereof, of 200 µg/ml or greater. In another embodiment, the treatment maintains a serum trough concentration of the anti-C5 antibody, or antigen binding fragment thereof, of 250 µg/ml or greater. In another embodiment, the treatment maintains a serum trough concentration of the anti-C5 antibody, or antigen binding fragment thereof, of 300 µg/ml or greater. In another embodiment, the treatment maintains a serum trough concentration of the anti-C5 antibody, or antigen binding fragment thereof, of between 100 µg/ml and 200 µg/ml. In another embodiment, the treatment maintains a serum trough concentration of the anti-C5 antibody, or antigen binding fragment thereof, of about 175 µg/ml.

In some embodiments, to obtain an effective response, the anti-C5 antibody is administered to the patient in an amount and with a frequency to maintain at least 50 µg, 55 µg, 60 µg, 65 µg, 70 µg, 75 µg, 80 µg, 85 µg, 90 µg, 95 µg, 100 µg, 105 µg, 110 µg, 115 µg, 120 µg, 125 µg, 130 µg, 135 µg, 140 µg, 145 µg, 150 µg, 155 µg, 160 µg, 165 µg, 170 µg, 175 µg, 180 µg, 185 µg, 190 µg, 195 µg, 200 µg, 205 µg, 210 µg, 215 µg, 220 µg, 225 µg, 230 µg, 235 µg, 240 µg, 245 µg, 250 µg, 255 µg, or 260 µg of antibody per milliliter of the patient's blood. In another embodiment, the anti-C5 antibody is administered to the patient in an amount and with a frequency to maintain between 50 ag and 250 ag of antibody per milliliter of the patient's blood. In another embodiment, the anti-C5 antibody is administered to the patient in an amount and with a frequency to maintain between 100 µg and 200 µg of antibody per milliliter of the patient's blood. In another embodiment, the anti-C5 antibody is administered to the patient in an amount and with a frequency to maintain about 175 µg of antibody per milliliter of the patient's blood.

The efficacy of the treatment methods provided herein can be assessed using any suitable means. In one embodiment, for a PNH patient, the treatment produces at least one therapeutic effect selected from the group consisting of a reduction or cessation in fatigue, abdominal pain, dyspnea, anemia [hemoglobin<10 g/dL], dysphagia, chest pain, and erectile dysfunction.

In another embodiment, the treatment results in terminal complement inhibition.

In another embodiment, the treatment produces a reduction in the need for blood transfusions.

In another embodiment, the treatment produces an increase in hemoglobin stabilization from the patient's pre-treatment baseline.

In another embodiment, the treatment produces a shift toward normal levels of a hemolysis-related hematologic biomarker selected from the group consisting of free hemoglobin, haptoglobin, reticulocyte count, PNH red blood cell (RBC) clone and D-dimer.

In another embodiment, the treatment results in a reduction in breakthrough hemolysis relative to treatment with eculizumab. In another embodiment, the treatment results in an elimination of breakthrough hemolysis during the treatment period. In another embodiment, the treatment results in a reduction of breakthrough hemolysis compared to pretreatment baseline amount of breakthrough hemolysis.

In another embodiment, the treatment produces a reduction in major adverse vascular events (MAVEs). In another embodiment, the treatment produces a shift toward normal levels of a chronic disease associated biomarker selected from the group consisting of estimated glomerular filtration rate (eGFR) and spot urine:albumin:creatinine and plasma brain natriuretic peptide (BNP).

In another embodiment, the treatment produces a change from baseline in quality of life as assessed via the Functional Assessment of Chronic Illness Therapy (FACIT)-Fatigue Scale, version 4 and the European Organisation for Research and Treatment of Cancer, Quality of Life Questionnaire-Core 30 Scale.

In a particular embodiment, lactate dehydrogenase (LDH) levels are used to evaluate responsiveness to a therapy (e.g., a reduction of hemolysis as assessed by lactate dehydrogenase (LDH) levels is indicative of an improvement in at least one sign of PNH). For example, in one embodiment, the treatments described herein result in a normalization of LDH levels.

In one embodiment, patients treated according to the disclosed methods experience reductions in LDH levels to near normal levels or to within 10%, or within 20% above what is considered the normal level (e.g., within 105-333 IU/L (international units per liter)). In another embodiment, the patient's LDH levels are normalized throughout maintenance period of treatment. In another embodiment, the treated patient's LDH levels are normalized at least at least 95% of the time while on the maintenance period of treatment. In another embodiment, the treated patient's LDH levels are normalized at least at least 90%, 85% or 80% of the time while on the maintenance period of treatment.

In one embodiment, patients treated according to the disclosed methods experience reductions in LDH levels to within normal levels or to within 10%, 20%, 30%, 40% or within 50% below what is considered the upper limit of normal level (e.g., within 105-333 IU/L (international units per liter).

In another aspect, an anti-C5 antibody, or antigen binding fragment thereof, is provided, comprising CDR1, CDR2 and CDR3 domains of the heavy chain variable region having the sequence set forth in SEQ ID NO:12, and CDR1, CDR2 and CDR3 domains of the light chain variable region having the sequence set forth in SEQ ID NO:8, for administration:

(a) intravenously on Day 1 of the administration cycle at
        a dose of:
          i. 2400 mg to a patient weighing ≥40 to <60 kg, or
          ii. 2700 mg to a patient weighing ≥60 to <100 kg; and
    (b) subcutaneously on Day 15 of the administration cycle
        and every week thereafter at a dose of 490 mg.

Also provided are kits that include a pharmaceutical composition containing an anti-C5 antibody, or antigen binding fragment thereof, such as ravulizumab, and a pharmaceutically-acceptable carrier, in a therapeutically effective amount adapted for use in the methods described herein. For example, in one embodiment, a kit for treating a human patient having a complement-associated condition (e.g., PNH) is provided, the kit comprising: (a) a dose of an anti-C5 antibody, or antigen binding fragment thereof, comprising CDR1, CDR2 and CDR3 domains of the heavy chain variable region having the sequence set forth in SEQ ID NO:12, and CDR1, CDR2 and CDR3 domains of the light chain variable region having the sequence set forth in SEQ ID NO:8; and (b) instructions for using the anti-C5 antibody, or antigen binding fragment thereof, in the methods described herein. In one embodiment, the anti-C5 antibody, or antigen binding fragment thereof, is administered to a patient weighing ≥40 to <60 kg: (a) intravenously once on Day 1 of the administration cycle at a dose of 2400 mg; and (b) subcutaneously on Day 15 of the administration cycle and every week thereafter at a dose of 490 mg. In another embodiment, the anti-C5 antibody, or antigen binding fragment thereof, is administered to a patient weighing ≥60 to <100 kg: (a) intravenously once on Day 1 of the administration cycle at a dose of 2700 mg; and (b) subcutaneously on Day 15 of the administration cycle and every week thereafter at a dose of 490 mg. In a particular embodiment, the anti-C5 antibody is ravulizumab.

Further provided is a device comprising a prefilled cartridge of ravulizumab for subcutaneous administration co-packaged with an on-body injector. In one embodiment, the device is sterile, for single use, disposable, and/or electro-mechanical. In another embodiment, the on-body injector comprises a 29-gauge needle. In another embodiment, the prefilled cartridge is a 3.5 mL cartridge. In another embodiment, ravulizumab for subcutaneous administration comprises 262.5 mg ravulizumab (70 mg/mL) in 50 mM sodium phosphate, 25 mM arginine, 5% sucrose, 0.05% polysorbate 80, and water for injection. In another embodiment, ravulizumab for subcutaneous administration consists of 262.5 mg ravulizumab (70 mg/mL) in 50 mM sodium phosphate, 25 mM arginine, 5% sucrose, 0.05% polysorbate 80, and water for injection. In another embodiment, ravulizumab for subcutaneous administration comprises 245 mg ravulizumab (70 mg/mL) in 50 mM sodium phosphate, 25 mM arginine, 5% sucrose, 0.05% polysorbate 80, and water for injection. In another embodiment, ravulizumab for subcutaneous administration consists of 245 mg ravulizumab (70 mg/mL) in 50 mM sodium phosphate, 25 mM arginine, 5% sucrose, 0.05% polysorbate 80, and water for injection. In another embodiment, ravulizumab for subcutaneous administration is formulated at a pH of about 7.4.

BRIEF DESCRIPTION OF THE DRAWING

FIG. 1 sets forth the Functional Assessment of Chronic Illness Therapy (FACIT) Fatigue Subscale Version 4 Questionnaire.

FIGS. 2A-2B sets forth the European Organisation for Research and Treatment of Cancer Quality of Life Questionnaire (Core 30).

FIG. 3 sets forth a sample Treatment Administration Satisfaction Questionnaire for Intravenous Administration (TASQ-IV).

FIG. 4 sets forth a sample Treatment Administration Satisfaction Questionnaire for Subcutaneous Administration (TASQ-SC).

administered subcutaneously (SC) versus (IV) intravenously in adult patients with PNH currently treated with eculizumab (SOLIRIS®). The ravulizumab (ULTOMIRIS®) SC dosage is as follows: Day 1 loading dose (IV)=2400 mg for patients weighing ≥40 kg to <60 kg and 2700 mg for patients weighing ≥60 kg to <100 kg; Day 15 and all subsequent SC doses=490 mg every week for all patients. The ravulizumab (ULTOMIRIS®) IV dosage is as follows: Day 1 loading dose (IV)=2400 mg for patients weighing ≥40 mg to <60 kg and 2700 mg for patients weighing ≥60 kg to <100 kg; Day 15 maintenance dose (IV)=3000 mg for patients weighing ≥40 kg to <60 kg, 3300 mg for patients weighing ≥60 kg to <100 kg. The Extension Period maintenance dose (SC) is 490 mg every week for all patients.

FIG. 6 summarizes patient disposition and analysis sets.

FIGS. 7A-7B set forth the patient demographics and baseline characteristics.

FIG. 8 sets forth the primary PK noninferiority analysis. The following abbreviations are used: SE=Standard Error; LSM=Least Squares Mean; CI=Confidence Interval.

Figure 9:
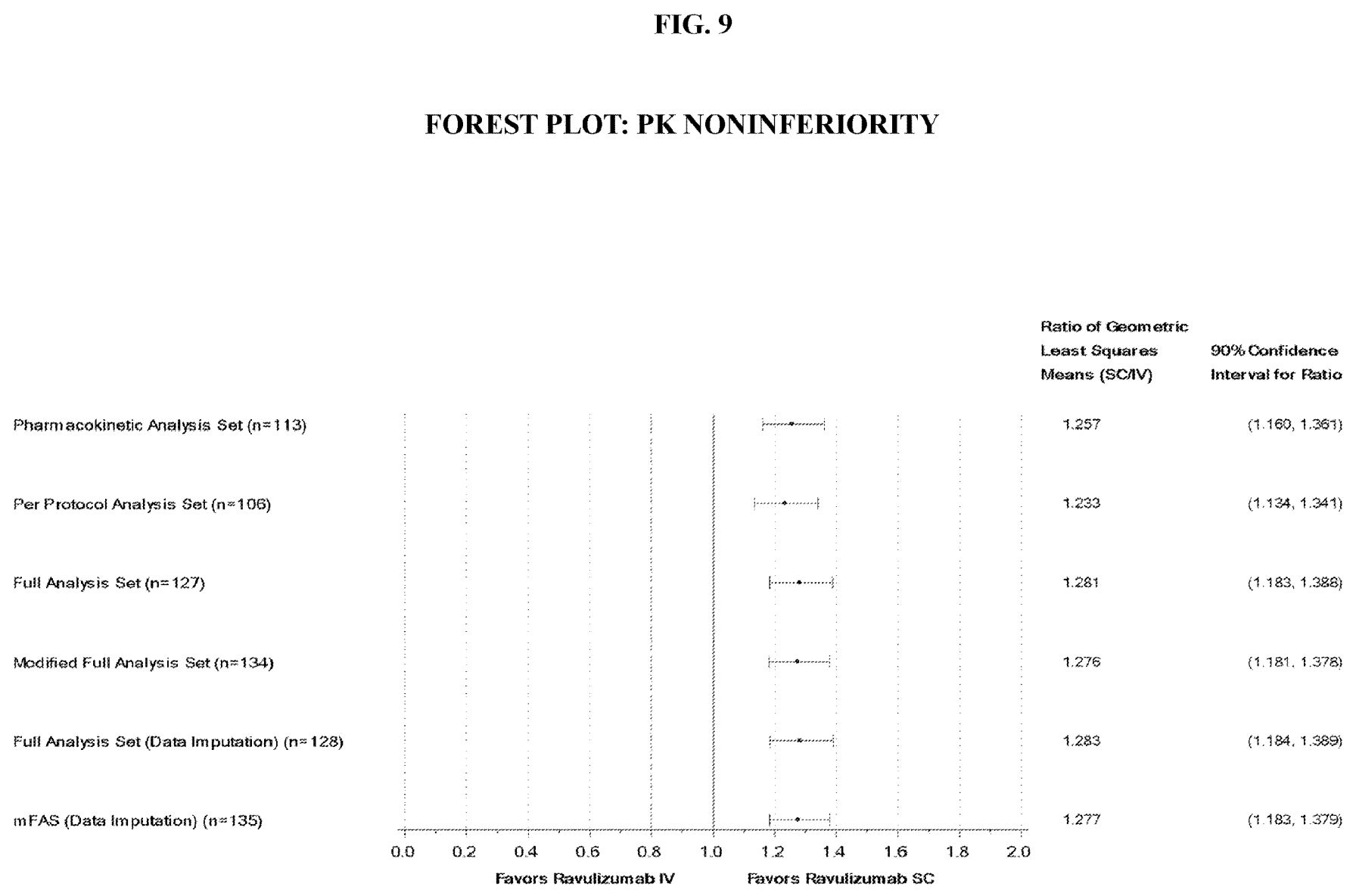

FIG. 9 is a Forest Plot of PK noninferiority.

Figure 10:
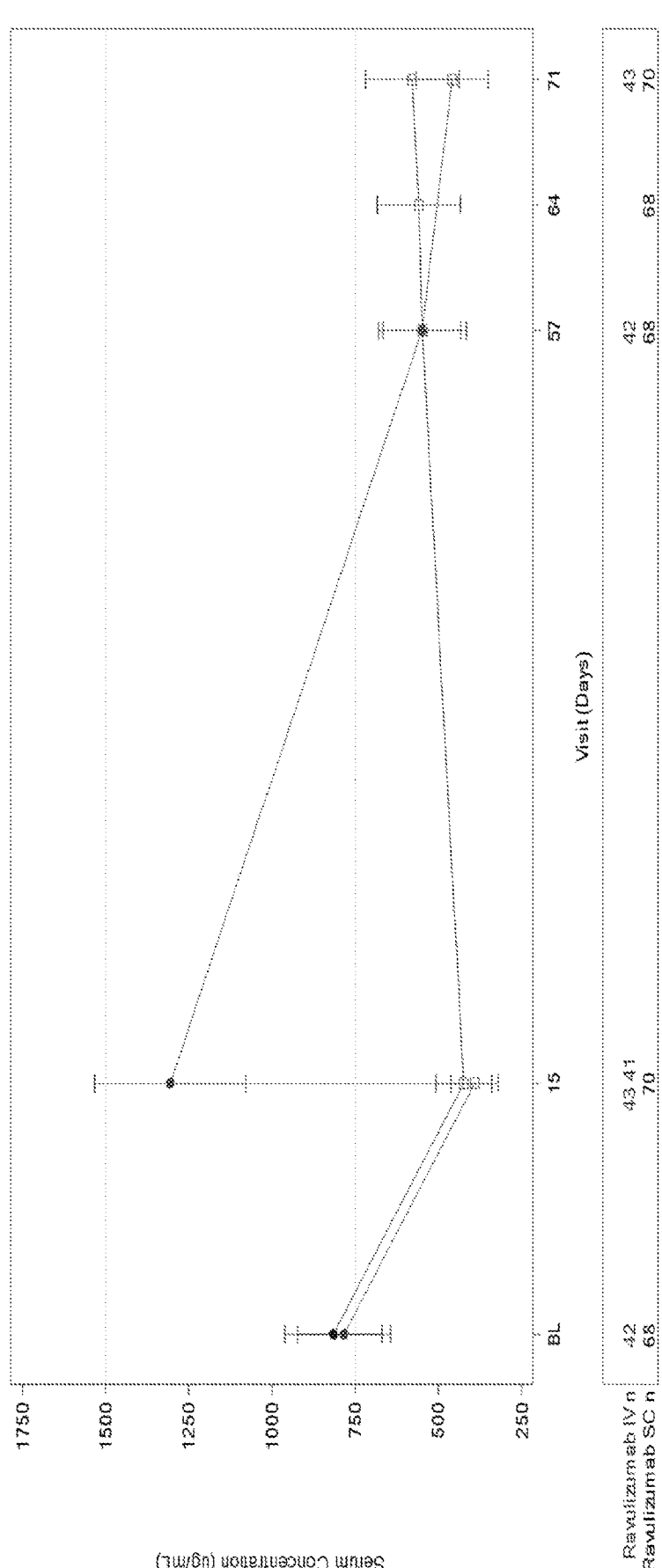

FIG. 10 depicts the mean serum ravulizumab concentration.

Figure 11:
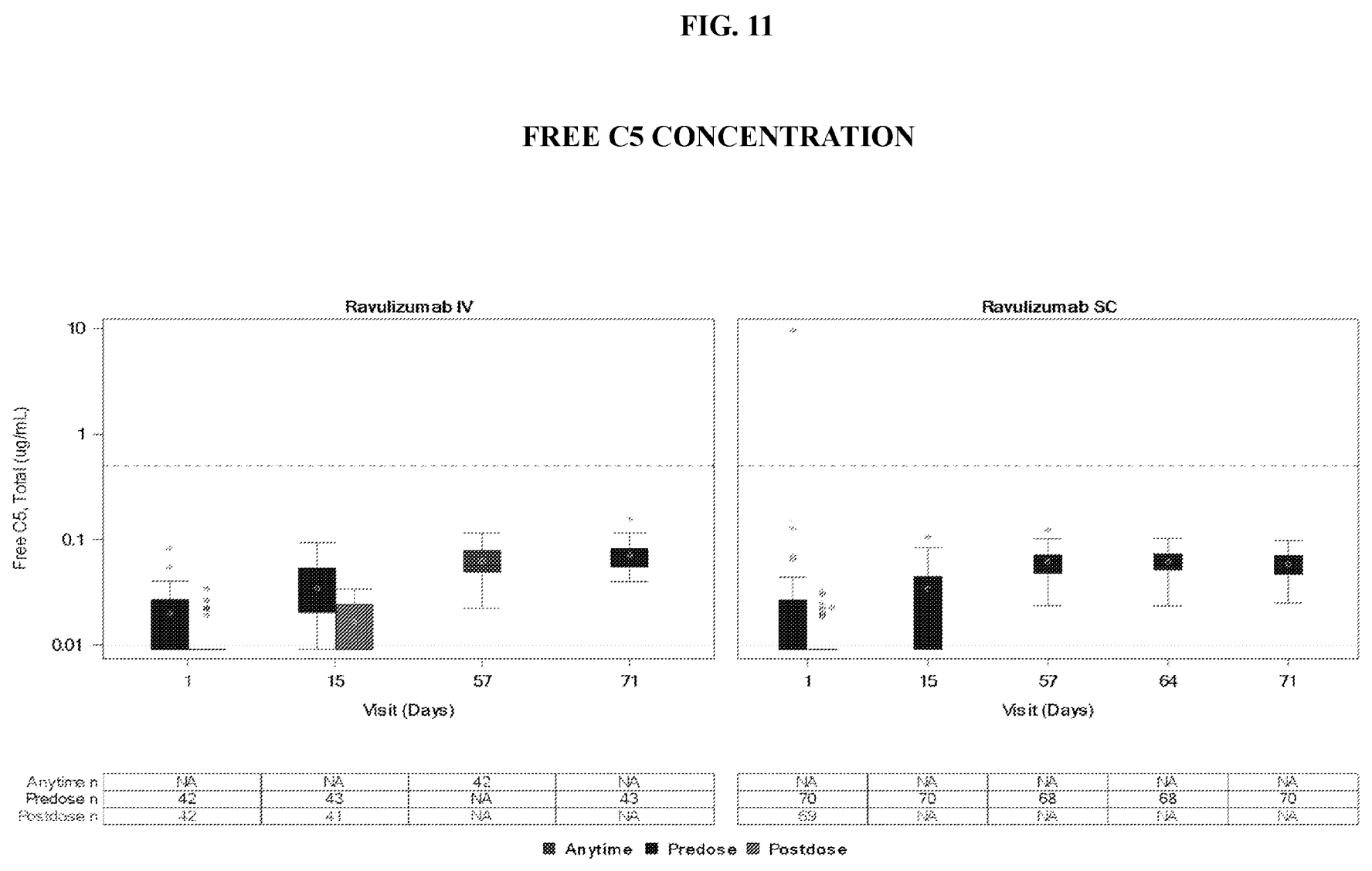

FIG. 11 depicts free C5 concentration.

Figure 12:
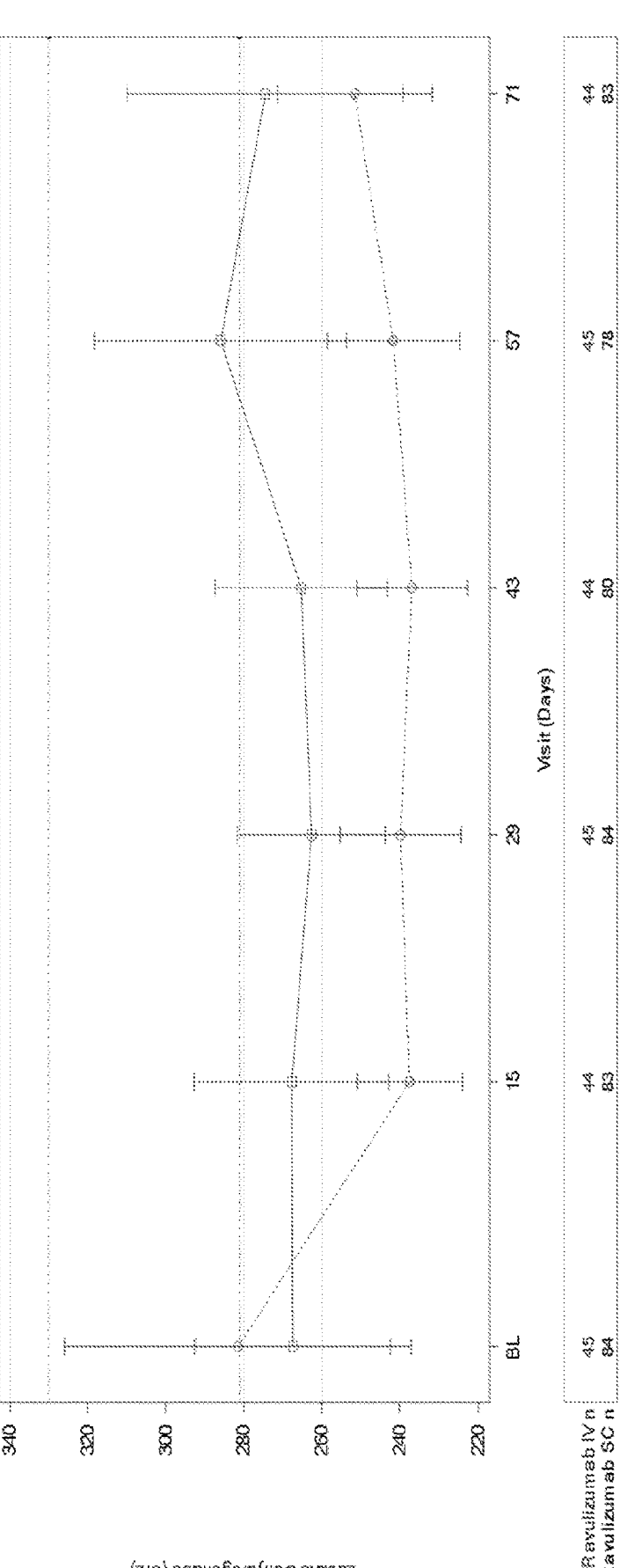

FIG. 12 depicts mean lactate dehydrogenase (LDH).

FIG. 13 shows breakthrough hemolysis and transfusion avoidance.

FIG. 14 shows hemoglobin stability and PNH symptomatology.

FIG. 15 provides a treatment emergent Adverse Events (AEs) overview.

FIG. 16 is a summary of serious adverse events (SAEs).

DETAILED DESCRIPTION

I. Definitions

As used herein, the term "subject" or "patient" is a human patient (e.g., a patient having Paroxysmal Nocturnal Hemoglobinuria (PNH)).

Paroxysmal nocturnal hemoglobinuria is an acquired hemolytic disorder that occurs most frequently in adults (Brodsky R A., *Blood.* 2015; 126:2459-65). The disease begins with the clonal expansion of a hematopoietic stem cell that has acquired a somatic mutation in the PIGA gene (Brodsky R A., *Blood.* 2014; 124:2804-1). Consequently, PNH blood cells lack the glycophosphatidylinositol (GPI) anchor protein and are deficient in the membrane-bound complement inhibitory proteins CD55 and CD59. In the absence of CD55, there is increased deposition of complement protein C3 cleavage products on blood cell membrane surfaces, in turn leading to cleavage of C5 into C5a and C5b. The pathology and clinical presentations in patients with PNH are driven by uncontrolled terminal complement activation.

C5a is a potent anaphylatoxin, chemotactic factor, and cell-activating molecule that mediates multiple pro-inflammatory and pro-thrombotic activities (Matis L A, et al., *Nat. Med.* 1995; 1:839-42; Prodinger et al., Complement. In: Paul W E, editor. Fundamental immunology (4th ed). Philadelphia: Lippincott-Raven Publishers; 1999. p. 967-95). C5b recruits the terminal complement components C6, C7, C8, and C9 to form the pro-inflammatory, pro-thrombotic cytolytic pore molecule C5b-9, a process that under normal circumstances would be blocked on the red blood cell (RBC) membrane by CD59. In patients with PNH, however, these final steps proceed unchecked, culminating in hemolysis and the release of free hemoglobin, as well as platelet activation (Hill, et al., *Blood* 2013; 121:4985-96). The signs and symptoms of PNH can be attributed to chronic, uncontrolled complement C5 cleavage, and release of C5a and C5b-9 leading to RBC hemolysis, which together result in (Hill, et al., *Blood* 2013; 121:4985-96; Brodsky R A., *Blood.* 2014; 124:2804-1): release of intracellular free hemoglobin and lactate dehydrogenase (LDH) into circulation as a direct consequence of hemolysis, irreversible binding to and inactivation of nitric oxide (NO) by hemoglobin, and inhibition of NO synthesis; vasoconstriction and tissue-bed ischemia due to absence of vasodilatory NO, as well as possible microthrombi manifesting as abdominal pain, dysphagia, and erectile dysfunction; platelet activation; and pro-inflammatory and prothrombotic state.

A substantial proportion of patients with PNH experience renal dysfunction and pulmonary hypertension (Hillmen, et al., *Am J Hematol.* 2010; 85:553-9. [erratum in Am J Hematol. 2010; 85:911.]; Hill, et al., *Br. J Haematol.* 2012; 158:409-14; Hill, et al., *Blood* 2013; 121:4985-96). Patients also experience venous or arterial thrombosis in diverse sites, including the abdomen or central nervous system (Brodsky R A., *Blood.* 2014; 124:2804-1).

As used herein, "effective treatment" refers to treatment producing a beneficial effect, e.g., amelioration of at least one symptom of a disease or disorder. Effective treatment may refer to alleviation of at least one symptom of PNH (e.g., fatigue, abdominal pain, dyspnea, anemia, dysphagia, chest pain, or erectile dysfunction). A beneficial effect can take the form of an improvement over baseline, i.e., an improvement over a measurement or observation made prior to initiation of therapy according to the method.

The term "effective amount" refers to an amount of an agent that provides the desired biological, therapeutic, and/or prophylactic result. That result can be reduction, amelioration, palliation, lessening, delaying, and/or alleviation of one or more of the signs, symptoms, or causes of a disease, or any other desired alteration of a biological system. In one example, an "effective amount" is the amount of anti-C5 antibody, or antigen binding fragment thereof, clinically proven to alleviate at least one symptom of PNH (e.g., fatigue, abdominal pain, dyspnea, anemia, dysphagia, chest pain, or erectile dysfunction). An effective amount can be administered in one or more administrations.

As used herein, the terms "induction" and "induction phase" are used interchangeably and refer to the first phase of treatment.

As used herein, the terms "maintenance" and "maintenance phase" are used interchangeably and refer to the second phase of treatment. In certain embodiments, treatment is continued as long as clinical benefit is observed or until unmanageable toxicity or disease progression occurs.

As used herein, the term "loading dose" refers to the initial dose administered to the patient. For example, a loading may be 2400 mg or 2700 mg. Loading doses may be titered based on body weight. In one embodiment, a loading dose is administered intravenously to the patient. In another embodiment, a loading dose is administered subcutaneously to the patient.

As used herein, the term "maintenance dose" refers to a dose administered to the patient after the loading dose. For example, a maintenance dose may be a dose of about 400 mg, 405 mg, 410 mg, 420 mg, 425 mg, 430 mg, 435 mg, 440 mg, 445 mg, 450 mg, 455 mg, 460 mg, 465 mg, 470 mg, 475 mg, 480 mg, 485 mg, 490 mg, 495 mg, 500 mg, 505 mg, 510 mg, 515 mg, 520 mg, 525 mg, 530 mg, 535 mg, 540 mg, 545 mg, 550 mg, 555 mg, 560 mg, 565 mg, 570 mg, 575 mg, 580 mg, 585 mg, 590 mg, 595 mg, or 600 mg. In one embodiment, the maintenance dose of the anti-C5 antibody, or antigen binding fragment thereof, is 490 mg. In one embodiment, a loading dose is administered subcutaneously to the patient.

As used herein, the term "serum trough level" refers to the lowest level that the agent (e.g., the anti-C5 antibody, or antigen binding fragment thereof) or medicine is present in the serum. In contrast, a "peak serum level", refers to the highest level of the agent in the serum. The "average serum level", refers to the mean level of the agent in the serum over time.

In one embodiment, the treatment regimens described are sufficient to maintain particular serum trough concentrations of the anti-C5 antibody, or antigen binding fragment thereof. For example, in one embodiment, the treatment maintains a serum trough concentration of the anti-C5 antibody, or antigen binding fragment thereof, of 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, or 400 µg/ml or greater. In one embodiment, the treatment maintains a serum trough concentration of the anti-C5 antibody, or antigen binding fragment thereof, of 100 µg/ml or greater. In another embodiment, the treatment maintains a serum trough concentration of the anti-C5 antibody, or antigen binding fragment thereof, of 150 µg/ml or greater. In another embodiment, the treatment maintains a serum trough concentration of the anti-C5 antibody, or antigen binding fragment thereof, of 200 µg/ml or greater. In another embodiment, the treatment maintains a serum trough concentration of the anti-C5 antibody, or antigen binding fragment thereof, of 250 µg/ml or greater. In another embodiment, the treatment maintains a serum trough concentration of the anti-C5 antibody, or antigen binding fragment thereof, of 300 µg/ml or greater. In another embodiment, the treatment maintains a serum trough concentration of the anti-C5 antibody, or antigen binding fragment thereof, of between 100 µg/ml and 200 µg/ml. In another embodiment, the treatment maintains a serum trough concentration of the anti-C5 antibody, or antigen binding fragment thereof, of about 175 µg/ml.

In some embodiments, to obtain an effective response, the anti-C5 antibody is administered to the patient in an amount and with a frequency to maintain at least 50 µg, 55 g, 60 µg, 65 µg, 70 µg, 75 µg, 80 µg, 85 µg, 90 µg, 95 µg, 100 µg, 105 µg, 110 µg, 115 µg, 120 µg, 125 µg, 130 µg, 135 µg, 140 µg, 145 µg, 150 µg, 155 µg, 160 µg, 165 µg, 170 µg, 175 µg, 180 ag, 185 µg, 190 µg, 195 µg, 200 µg, 205 µg, 210 µg, 215 µg, 220 µg, 225 µg, 230 µg, 235 µg, 240 µg, 245 µg, 250 µg, 255 µg, or 260 µg of antibody per milliliter of the patient's blood. In another embodiment, the anti-C5 antibody is administered to the patient in an amount and with a frequency to maintain between 50 µg and 250 µg of antibody per milliliter of the patient's blood.

In another embodiment, the anti-C5 antibody is administered to the patient in an amount and with a frequency to maintain between 100 µg and 200 µg of antibody per milliliter of the patient's blood. In another embodiment, the anti-C5 antibody is administered to the patient in an amount and with a frequency to maintain about 175 µg of antibody per milliliter of the patient's blood.

In another embodiment, to obtain an effective response, the anti-C5 antibody is administered to the patient in an amount and with a frequency to maintain a minimum free C5 concentration. For example, in one embodiment, the anti-C5 antibody is administered to the patient in an amount and with a frequency to maintain a free C5 concentration of 0.2 µg/mL, 0.3 µg/mL, 0.4 µg/mL, 0.5 µg/mL or below. In another embodiment, the anti-C5 antibody is administered to the patient in an amount and with a frequency to maintain a free C5 concentration between 0.309 and 0.5 µg/mL. In another embodiment, the treatment described herein reduces free C5 concentration by greater than 99% throughout the treatment period. In another embodiment, the treatment reduces free C5 concentration greater than 99.5% throughout the treatment period.

The term "antibody" describes polypeptides comprising at least one antibody derived antigen binding site (e.g., VH/VL region or Fv, or CDR). Antibodies include known forms of antibodies. For example, the antibody can be a human antibody, a humanized antibody, a bispecific antibody, or a chimeric antibody. The antibody also can be a Fab, Fab'2, ScFv, SMIP, Affibody®, nanobody, or a domain antibody. The antibody also can be of any of the following isotypes: IgG1, IgG2, IgG3, IgG4, IgM, IgA1, IgA2, IgAsec, IgD, and IgE. The antibody may be a naturally occurring antibody or may be an antibody that has been altered by a protein engineering technique (e.g., by mutation, deletion, substitution, conjugation to a non-antibody moiety). For example, an antibody may include one or more variant amino acids (compared to a naturally occurring antibody), which changes a property (e.g., a functional property) of the antibody. For example, numerous such alterations are known in the art which affect, e.g., half-life, effector function, and/or immune responses to the antibody in a patient. The term antibody also includes artificial or engineered polypeptide constructs which comprise at least one antibody-derived antigen binding site.

II. Anti-C5 Antibodies

The anti-C5 antibodies described herein bind to complement component C5 (e.g., human C5) and inhibit the cleavage of C5 into fragments C5a and C5b. Anti-C5 antibodies (or VH/VL domains derived therefrom) suitable for use in the invention can be generated using methods well known in the art. Alternatively, art recognized anti-C5 antibodies can be used. Antibodies that compete with any of these art-recognized antibodies for binding to C5 also can be used.

Eculizumab (also known as SOLIRIS®) is an anti-C5 antibody comprising heavy and light chains having sequences shown in SEQ ID NO: 10 and 11, respectively, or antigen binding fragments and variants thereof. Eculizumab is described in PCT/US1995/005688 and U.S. Pat. No. 6,355,245, the teachings or which are hereby incorporated by reference. In one embodiment the anti-C5 antibody, comprises the CDR1, CDR2, and CDR3 domains of the VH region of eculizumab having the sequence set forth in SEQ ID NO: 7, and the CDR1, CDR2 and CDR3 domains of the VL region of eculizumab having the sequence set forth in SEQ ID NO: 8. In another embodiment, the antibody comprises heavy chain CDR1, CDR2 and CDR3 domains having the sequences set forth in SEQ ID NOs: 1, 2, and 3, respectively, and light chain CDR1, CDR2 and CDR3 domains having the sequences set forth in SEQ ID NOs: 4, 5, and 6, respectively. In another embodiment, the antibody comprises VH and VL regions having the amino acid sequences set forth in SEQ ID NO: 7 and SEQ ID NO: 8, respectively.

An exemplary anti-C5 antibody is ravulizumab comprising heavy and light chains having the sequences shown in SEQ ID NOs: 14 and 11, respectively, or antigen binding fragments and variants thereof. Ravulizumab (also known as ULTOMIRIS®, BNJ441, and ALXN1210) is described in PCT/US2015/019225 and U.S. Pat. No. 9,079,949, the teachings or which are hereby incorporated by reference. The terms ravulizumab, ULTOMIRIS®, BNJ441, and ALXN1210 may be used interchangeably throughout this document, but all refer to the same antibody. Ravulizumab selectively binds to human complement protein C5, inhibiting its cleavage to C5a and C5b during complement activation. This inhibition prevents the release of the proinflammatory mediator C5a and the formation of the cytolytic pore-forming membrane attack complex (MAC) C5b-9 while preserving the proximal or early components of complement activation (e.g., C3 and C3b) essential for the opsonization of microorganisms and clearance of immune complexes.

In other embodiments, the antibody comprises the heavy and light chain CDRs or variable regions of ravulizumab. For example, in one embodiment, the antibody comprises the CDR1, CDR2, and CDR3 domains of the VH region of ravulizumab having the sequence set forth in SEQ ID NO:12, and the CDR1, CDR2 and CDR3 domains of the VL region of ravulizumab having the sequence set forth in SEQ ID NO:8. In another embodiment, the antibody comprises heavy chain CDR1, CDR2 and CDR3 domains having the sequences set forth in SEQ ID NOs:19, 18, and 3, respectively, and light chain CDR1, CDR2 and CDR3 domains having the sequences set forth in SEQ ID NOs:4, 5, and 6, respectively. In another embodiment, the antibody comprises VH and VL regions having the amino acid sequences set forth in SEQ ID NO:12 and SEQ ID NO:8, respectively.

Another exemplary anti-C5 antibody is antibody BNJ421 comprising heavy and light chains having the sequences shown in SEQ ID NOs: 20 and 11, respectively, or antigen binding fragments and variants thereof. BNJ421 (also known as ALXN1211) is described in PCT/US2015/019225 and U.S. Pat. No. 9,079,949, the teachings or which are hereby incorporated by reference.

In other embodiments, the antibody comprises the heavy and light chain CDRs or variable regions of BNJ421. Accordingly, in one embodiment, the antibody comprises the CDR1, CDR2, and CDR3 domains of the VH region of BNJ421 having the sequence set forth in SEQ ID NO:12, and the CDR1, CDR2 and CDR3 domains of the VL region of BNJ421 having the sequence set forth in SEQ ID NO:8. In another embodiment, the antibody comprises heavy chain CDR1, CDR2 and CDR3 domains having the sequences set forth in SEQ ID NOs:19, 18, and 3, respectively, and light chain CDR1, CDR2 and CDR3 domains having the sequences set forth in SEQ ID NOs:4, 5, and 6, respectively. In another embodiment, the antibody comprises VH and VL regions having the amino acid sequences set forth in SEQ ID NO:12 and SEQ ID NO:8, respectively.

The exact boundaries of CDRs have been defined differently according to different methods. In some embodiments, the positions of the CDRs or framework regions within a light or heavy chain variable domain can be as defined by Kabat et al. [(1991) "Sequences of Proteins of Immunological Interest." NIH Publication No. 91-3242, U.S. Department of Health and Human Services, Bethesda, MD]. In such cases, the CDRs can be referred to as "Kabat CDRs" (e.g., "Kabat LCDR2" or "Kabat HCDR1"). In some embodiments, the positions of the CDRs of a light or heavy chain variable region can be as defined by Chothia et al. (1989) *Nature* 342:877-883. Accordingly, these regions can be referred to as "Chothia CDRs" (e.g., "Chothia LCDR2"

or "Chothia HCDR3"). In some embodiments, the positions of the CDRs of the light and heavy chain variable regions can be as defined by a Kabat-Chothia combined definition. In such embodiments, these regions can be referred to as "combined Kabat-Chothia CDRs". Thomas et al. [(1996) *Mol Immunol* 33(17/18):1389-1401] exemplifies the identification of CDR boundaries according to Kabat and Chothia definitions.

In some embodiments, an anti-C5 antibody described herein comprises a heavy chain CDR1 comprising, or consisting of, the following amino acid sequence: GHIFSNY-WIQ (SEQ ID NO: 19). In some embodiments, an anti-C5 antibody described herein comprises a heavy chain CDR2 comprising, or consisting of, the following amino acid sequence: EILPGSGHTEYTENFKD (SEQ ID NO:18). In some embodiments, an anti-C5 antibody described herein comprises a heavy chain variable region comprising the following amino acid sequence:

```
                                         (SEQ ID NO: 12)
QVQLVQSGAEVKKPGASVKVSCKASGHIFSNYWIQWVRQAPGQGLEWMG

EILPGSGHTEYTENFKDRVTMTRDTSTSTVYMELSSLRSEDTAVYYCAR

YFFGSSPNWYFDVWGQGTLVTVSS.
```

In some embodiments, an anti-C5 antibody described herein comprises a light chain variable region comprising the following amino acid sequence:

```
                                          (SEQ ID NO: 8)
DIQMTQSPSSLSASVGDRVTITCGASENIYGALNWYQQKPGKAPKLLIY

GATNLADGVPSRFSGSGSGTDFTLTISSLQPEDFATYYCQNVLNTPLTF

GQGTKVEIK.
```

Another exemplary anti-C5 antibody is the 7086 antibody described in U.S. Pat. Nos. 8,241,628 and 8,883,158. In one embodiment, the antibody comprises the heavy and light chain CDRs or variable regions of the 7086 antibody (see U.S. Pat. Nos. 8,241,628 and 8,883,158). In another embodiment, the antibody, or antigen binding fragment thereof, comprises heavy chain CDR1, CDR2 and CDR3 domains having the sequences set forth in SEQ ID NOs: 21, 22, and 23, respectively, and light chain CDR1, CDR2 and CDR3 domains having the sequences set forth in SEQ ID NOs: 24, 25, and 26, respectively. In another embodiment, the antibody, or antigen binding fragment thereof, comprises the VH region of the 7086 antibody having the sequence set forth in SEQ ID NO:27, and the VL region of the 7086 antibody having the sequence set forth in SEQ ID NO:28.

Another exemplary anti-C5 antibody is the 8110 antibody also described in U.S. Pat. Nos. 8,241,628 and 8,883,158. In one embodiment, the antibody comprises the heavy and light chain CDRs or variable regions of the 8110 antibody. In another embodiment, the antibody, or antigen binding fragment thereof, comprises heavy chain CDR1, CDR2 and CDR3 domains having the sequences set forth in SEQ ID NOs: 29, 30, and 31, respectively, and light chain CDR1, CDR2 and CDR3 domains having the sequences set forth in SEQ ID NOs: 32, 33, and 34, respectively. In another embodiment, the antibody comprises the VH region of the 8110 antibody having the sequence set forth in SEQ ID NO: 35, and the VL region of the 8110 antibody having the sequence set forth in SEQ ID NO: 36.

Another exemplary anti-C5 antibody is the 305LO5 antibody described in US2016/0176954A1. In one embodiment, the antibody comprises the heavy and light chain CDRs or variable regions of the 305LO5 antibody. In another embodiment, the antibody, or antigen binding fragment thereof, comprises heavy chain CDR1, CDR2 and CDR3 domains having the sequences set forth in SEQ ID NOs: 37, 38, and 39, respectively, and light chain CDR1, CDR2 and CDR3 domains having the sequences set forth in SEQ ID NOs: 40, 41, and 42, respectively. In another embodiment, the antibody comprises the VH region of the 305LO5 antibody having the sequence set forth in SEQ ID NO: 43, and the VL region of the 305LO5 antibody having the sequence set forth in SEQ ID NO: 44.

Another exemplary anti-C5 antibody is the SKY59 antibody described in Fukuzawa T., et al., Rep. 2017 Apr. 24; 7(1):1080). In one embodiment, the antibody comprises the heavy and light chain CDRs or variable regions of the SKY59 antibody. In another embodiment, the antibody, or antigen binding fragment thereof, comprises a heavy chain comprising SEQ ID NO: 45 and a light chain comprising SEQ ID NO: 46.

Another exemplary anti-C5 antibody is the REGN3918 antibody (also known as H4H12166PP) described in US20170355757. In one embodiment, the antibody comprises a heavy chain variable region comprising SEQ ID NO:47 and a light chain variable region comprising SEQ ID NO:48. In another embodiment, the antibody comprises a heavy chain comprising SEQ ID NO:49 and a light chain comprising SEQ ID NO:50.

In another embodiment, the antibody competes for binding with, and/or binds to the same epitope on C5 as, the above-mentioned antibodies (e.g., eculizumab, ravulizumab, 7086 antibody, 8110 antibody, 305LO5 antibody, SKY59 antibody, or REGN3918 antibody). In another embodiment, the antibody has at least about 90% variable region amino acid sequence identity with the above-mentioned antibodies (e.g., at least about 90%, 91%, 92%, 93%, 94%, 95%, 96%, 97%, 98% or 99% variable region identity).

An anti-C5 antibody described herein can, in some embodiments, comprise a variant human Fc constant region that binds to human neonatal Fc receptor (FcRn) with greater affinity than that of the native human Fc constant region from which the variant human Fc constant region was derived. For example, the Fc constant region can comprise one or more (e.g., two, three, four, five, six, seven, or eight or more) amino acid substitutions relative to the native human Fc constant region from which the variant human Fc constant region was derived. At a pH level of 6.0, the substitutions can increase the binding affinity of an IgG antibody containing the variant Fc constant region to FcRn, while maintaining the pH dependence of the interaction.

Substitutions that enhance the binding affinity of an antibody Fc constant region for FcRn are known in the art and include, e.g., (1) the M252Y/S254T/T256E triple substitution described by Dall'Acqua et al. (2006) *J Biol Chem* 281: 23514-23524; (2) the M428L or T250Q/M428L substitutions described in Hinton et al. (2004) *J Biol Chem* 279:6213-6216 and Hinton et al. (2006) *J Immunol* 176: 346-356; and (3) the N434A or T307/E380A/N434A substitutions described in Petkova et al. (2006) *Int Immunol* 18(12):1759-69. The additional substitution pairings: P257I/Q311I, P257I/N434H, and D376V/N434H are described in, e.g., Datta-Mannan et al. (2007) *J Biol Chem* 282(3):1709-1717, the disclosure of which is incorporated herein by reference in its entirety. Methods for testing whether one or more substitutions in the Fc constant region of an antibody increase the affinity of the Fc constant region for FcRn at pH 6.0 (while maintaining pH dependence of the interaction) are known in the art and exemplified in the working examples. See, e.g., PCT/US2015/019225 and U.S. Pat. No. 9,079,949 the disclosures of each of which are incorporated herein by reference in their entirety.

In some embodiments, the variant constant region has a substitution for valine at EU amino acid residue 255. In some embodiments, the variant constant region has a substitution at EU amino acid residue 309 for asparagine. In some embodiments, the variant constant region has a substitution for isoleucine at EU amino acid residue 312. In some embodiments, the variant constant region has a substitution at EU amino acid residue 386.

In some embodiments, the variant Fc constant region comprises no more than 30 (e.g., no more than 29, 28, 27, 26, 25, 24, 23, 22, 21, 20, 19, 18, 17, 16, 15, 14, 13, 12, 11, 10, nine, eight, seven, six, five, four, three, or two) amino acid substitutions, insertions, or deletions relative to the native constant region from which it was derived. In some embodiments, the variant Fc constant region comprises one or more amino acid substitutions selected from the group consisting of: M252Y, S254T, T256E, N434S, M428L, V259I, T250I, and V308F. In some embodiments, the variant human Fc constant region comprises a methionine at position 428 and an asparagine at position 434 of a native human IgG Fc constant region, each in EU numbering. In some embodiments, the variant Fc constant region comprises a 428L/434S double substitution as described in, e.g., U.S. Pat. No. 8,088,376.

In some embodiments, the variant constant region comprises a substitution at amino acid position 237, 238, 239, 248, 250, 252, 254, 255, 256, 257, 258, 265, 270, 286, 289, 297, 298, 303, 305, 307, 308, 309, 311, 312, 314, 315, 317, 325, 332, 334, 360, 376, 380, 382, 384, 385, 386, 387, 389, 424, 428, 433, 434, or 436 (EU numbering) relative to the native human Fc constant region. In some embodiments, the substitution is selected from the group consisting of: methionine for glycine at position 237; alanine for proline at position 238; lysine for serine at position 239; isoleucine for lysine at position 248; alanine, phenylalanine, isoleucine, methionine, glutamine, serine, valine, tryptophan, or tyrosine for threonine at position 250; phenylalanine, tryptophan, or tyrosine for methionine at position 252; threonine for serine at position 254; glutamic acid for arginine at position 255; aspartic acid, glutamic acid, or glutamine for threonine at position 256; alanine, glycine, isoleucine, leucine, methionine, asparagine, serine, threonine, or valine for proline at position 257; histidine for glutamic acid at position 258; alanine for aspartic acid at position 265; phenylalanine for aspartic acid at position 270; alanine, or glutamic acid for asparagine at position 286; histidine for threonine at position 289; alanine for asparagine at position 297; glycine for serine at position 298; alanine for valine at position 303; alanine for valine at position 305; alanine, aspartic acid, phenylalanine, glycine, histidine, isoleucine, lysine, leucine, methionine, asparagine, proline, glutamine, arginine, serine, valine, tryptophan, or tyrosine for threonine at position 307; alanine, phenylalanine, isoleucine, leucine, methionine, proline, glutamine, or threonine for valine at position 308; alanine, aspartic acid, glutamic acid, proline, or arginine for leucine or valine at position 309; alanine, histidine, or isoleucine for glutamine at position 311; alanine or histidine for aspartic acid at position 312; lysine or arginine for leucine at position 314; alanine or histidine for asparagine at position 315; alanine for lysine at position 317; glycine for asparagine at position 325; valine for isoleucine at position 332; leucine for lysine at position 334; histidine for lysine at position 360; alanine for aspartic acid at position 376;

alanine for glutamic acid at position 380; alanine for glutamic acid at position 382; alanine for asparagine or serine at position 384; aspartic acid or histidine for glycine at position 385; proline for glutamine at position 386; glutamic acid for proline at position 387; alanine or serine for asparagine at position 389; alanine for serine at position 424; alanine, aspartic acid, phenylalanine, glycine, histidine, isoleucine, lysine, leucine, asparagine, proline, glutamine, serine, threonine, valine, tryptophan, or tyrosine for methionine at position 428; lysine for histidine at position 433; alanine, phenylalanine, histidine, serine, tryptophan, or tyrosine for asparagine at position 434; and histidine for tyrosine or phenylalanine at position 436, all in EU numbering.

In some embodiments the precise location of these mutations may be shifted from the native human Fc constant region position due to antibody engineering. For example, the 428L/434S double substitution when used in a IgG2/4 chimeric Fc may correspond to 429L and 435S as in the M429L and N435S variants found in BNJ441 (ravulizumab) and described in U.S. Pat. No. 9,079,949, the disclosure of which is incorporated herein by reference in its entirety.

Suitable anti-C5 antibodies for use in the methods described herein, in some embodiments, comprise a heavy chain polypeptide comprising the amino acid sequence depicted in SEQ ID NO:14 and/or a light chain polypeptide comprising the amino acid sequence depicted in SEQ ID NO:11. Alternatively, the anti-C5 antibodies for use in the methods described herein, in some embodiments, comprise a heavy chain polypeptide comprising the amino acid sequence depicted in SEQ ID NO:20 and/or a light chain polypeptide comprising the amino acid sequence depicted in SEQ ID NO:11.

In one embodiment, the antibody binds to C5 at a pH of 7.4 at 25° C. (and, otherwise, under physiologic conditions) with an affinity dissociation constant ($K_D$) that is at least 0.1 (e.g., at least 0.15, 0.175, 0.2, 0.25, 0.275, 0.3, 0.325, 0.35, 0.375, 0.4, 0.425, 0.45, 0.475, 0.5, 0.525, 0.55, 0.575, 0.6, 0.625, 0.65, 0.675, 0.7, 0.725, 0.75, 0.775, 0.8, 0.825, 0.85, 0.875, 0.9, 0.925, 0.95, or 0.975) nM. In some embodiments, the $K_D$ of the anti-C5 antibody, or antigen binding fragment thereof, is no greater than 1 (e.g., no greater than 0.9, 0.8, 0.7, 0.6, 0.5, 0.4, 0.3, or 0.2) nM.

In other embodiments, the dissociation quotient [($K_D$ of the antibody for C5 at pH 6.0 at 25° C.)/($K_D$ of the antibody for C5 at pH 7.4 at 25° C.)] is greater than 21 (e.g., greater than 22, 23, 24, 25, 26, 27, 28, 29, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 350, 400, 450, 500, 600, 700, 800, 900, 1000, 1500, 2000, 2500, 3000, 3500, 4000, 4500, 5000, 5500, 6000, 6500, 7000, 7500, or 8000).

Methods for determining whether an antibody binds to a protein antigen and/or the affinity for an antibody to a protein antigen are known in the art. For example, the binding of an antibody to a protein antigen can be detected and/or quantified using a variety of techniques such as, but not limited to, Western blot, dot blot, surface plasmon resonance (SPR) method (e.g., BIAcore system; Pharmacia Biosensor AB, Uppsala, Sweden and Piscataway, N.J.), or enzyme-linked immunosorbent assay (ELISA). See, e.g., Benny K. C. Lo (2004) "Antibody Engineering: Methods and Protocols," Humana Press (ISBN: 1588290921); Johne et al. (1993) *J Immunol Meth* 160:191-198; Jonsson et al. (1993) *Ann Biol Clin* 51:19-26; and Jonsson et al. (1991) *Biotechniques* 11:620-627. In addition, methods for measuring the affinity (e.g., dissociation and association constants) are set forth in the working examples.

As used herein, the term "$k_a$" refers to the rate constant for association of an antibody to an antigen. The term "$k_d$" refers to the rate constant for dissociation of an antibody from the antibody/antigen complex. And the term "$K_D$" refers to the equilibrium dissociation constant of an anti- body-antigen interaction. The equilibrium dissociation con- stant is deduced from the ratio of the kinetic rate constants, $K_D = k_d/k_a$. Such determinations preferably are measured at 25° C. or 37° C. (see the working examples). For example, the kinetics of antibody binding to human C5 can be determined at pH 8.0, 7.4, 7.0, 6.5 and 6.0 via surface plasmon resonance (SPR) on a BIAcore 3000 instrument using an anti-Fc capture method to immobilize the antibody.

In one embodiment, the anti-C5 antibody, or antigen binding fragment thereof, blocks the generation or activity of the C5a and/or C5b active fragments of a C5 protein (e.g., a human C5 protein). Through this blocking effect, the antibodies inhibit, e.g., the pro-inflammatory effects of C5a and the generation of the C5b-9 membrane attack complex (MAC) at the surface of a cell.

Methods for determining whether a particular antibody described herein inhibits C5 cleavage are known in the art. Inhibition of human complement component C5 can reduce the cell-lysing ability of complement in a subject's bodily fluids. Such reductions of the cell-lysing ability of comple- ment present in the body fluid(s) can be measured by methods well known in the art such as, for example, by a conventional hemolytic assay such as the hemolysis assay described by Kabat and Mayer (eds.), "Experimental Immu- nochemistry, 2$^{nd}$ Edition," 135-240, Springfield, IL, CC Thomas (1961), pages 135-139, or a conventional variation of that assay such as the chicken erythrocyte hemolysis method as described in, e.g., Hillmen et al. (2004) *N Engl J Med* 350(6):552. Methods for determining whether a can- didate compound inhibits the cleavage of human C5 into forms C5a and C5b are known in the art and described in Evans et al. (1995) *Mol Immunol* 32(16):1183-95. For example, the concentration and/or physiologic activity of C5a and C5b in a body fluid can be measured by methods well known in the art. For C5b, hemolytic assays or assays for soluble C5b-9, as discussed herein, can be used. Other assays known in the art can also be used. Using assays of these or other suitable types, candidate agents capable of inhibiting human complement component C5 can be screened.

Immunological techniques such as, but not limited to, ELISA can be used to measure the protein concentration of C5 and/or its split products to determine the ability of an anti-C5 antibody, or antigen binding fragment thereof, to inhibit conversion of C5 into biologically active products. In some embodiments, C5a generation is measured. In some embodiments, C5b-9 neoepitope-specific antibodies are used to detect the formation of terminal complement.

Hemolytic assays can be used to determine the inhibitory activity of an anti-C5 antibody, or antigen binding fragment thereof, on complement activation. For example, sheep erythrocytes coated with hemolysin or chicken erythrocytes sensitized with anti-chicken erythrocyte antibody can be used as target cells to determine the effect of an anti-C5 antibody, or antigen binding fragment thereof, on classical complement pathway-mediated hemolysis in a serum test solution in vitro. The percentage of lysis is normalized by considering 100% lysis equal to the lysis occurring in the absence of the inhibitor. In some embodiments, the classical complement pathway is activated by a human IgM antibody, for example, as utilized in the Wieslab@Classical Pathway Complement Kit (Wieslab® COMPL CP310, Euro-Diagnostica, Sweden). Briefly, the test serum is incubated with an anti-C5 antibody, or antigen binding fragment thereof, in the presence of a human IgM antibody. The amount of C5b-9 that is generated is measured by contacting the mixture with an enzyme conjugated anti-C5b-9 antibody and a fluoro- genic substrate and measuring the absorbance at the appro- priate wavelength. As a control, the test serum is incubated in the absence of the anti-C5 antibody, or antigen binding fragment thereof. In some embodiments, the test serum is a C5-deficient serum reconstituted with a C5 polypeptide.

Unsensitized rabbit or guinea pig erythrocytes can be used as target cells to determine the effect of an anti-C5 antibody, or antigen binding fragment thereof, on alternative pathway- mediated hemolysis. In some embodiments, the serum test solution is a C5-deficient serum reconstituted with a C5 polypeptide. The percentage of lysis is normalized by con- sidering 100% lysis equal to the lysis occurring in the absence of the inhibitor. In some embodiments, the alterna- tive complement pathway is activated by lipopolysaccharide molecules, for example, as utilized in the Wieslab® Alter- native Pathway Complement Kit (Wieslab® COMPL AP330, Euro-Diagnostica, Sweden). Briefly, the test serum is incubated with an anti-C5 antibody, or antigen binding fragment thereof, in the presence of lipopolysaccharide. The amount of C5b-9 that is generated is measured by contacting the mixture with an enzyme conjugated anti-C5b-9 antibody and a fluorogenic substrate, and measuring the fluorescence at the appropriate wavelength. As a control, the test serum is incubated in the absence of the anti-C5 antibody, or antigen binding fragment thereof.

In some embodiments, C5 activity, or inhibition thereof, is quantified using a CH50eq assay. The CH50eq assay is a method for measuring the total classical complement activ- ity in serum. This is a lytic assay test, which uses antibody- sensitized erythrocytes as the activator of the classical complement pathway, and various dilutions of the test serum to determine the amount required to give 50% lysis (CH50). The percent hemolysis can be determined, for example, using a spectrophotometer. The CH50eq assay provides an indirect measure of terminal complement complex (TCC) formation, since the TCC itself is directly responsible for the measured hemolysis.

The assay is well known and commonly practiced by those of skill in the art. Briefly, to activate the classical complement pathway, undiluted serum samples (e.g., recon- stituted human serum samples) are added to microassay wells containing the antibody-sensitized erythrocytes to thereby generate TCC. Next, the activated sera are diluted in microassay wells, which are coated with a capture reagent (e.g., an antibody that binds to one or more components of the TCC). The TCC present in the activated samples bind to the monoclonal antibodies coating the surface of the microassay wells. The wells are washed and a detection reagent, which is detectably labeled and recognizes the bound TCC, is added to each well. The detectable label can be, e.g., a fluorescent label or an enzymatic label. The assay results are expressed in CH50 unit equivalents per milliliter (CH50 U Eq/mL).

Inhibition, e.g., as it pertains to terminal complement activity, includes at least a 5 (e.g., at least a 6, 7, 8, 9, 10, 15, 20, 25, 30, 35, 40, 45, 50, 55, or 60) % decrease in the activity of terminal complement in, e.g., a hemolytic assay or CH50eq assay as compared to the effect of a control antibody (or antigen-binding fragment thereof) under simi- lar conditions and at an equimolar concentration. Substantial inhibition, as used herein, refers to inhibition of a given activity (e.g., terminal complement activity) of at least 40

(e.g., at least 45, 50, 55, 60, 65, 70, 75, 80, 85, 90, or 95 or greater) %. In some embodiments, an anti-C5 antibody described herein contains one or more amino acid substitutions relative to the CDRs of eculizumab (i.e., SEQ ID NOs:1-6), yet retains at least 30 (e.g., at least 31, 32, 33, 34, 35, 36, 37, 38, 39, 40, 41, 42, 43, 44, 45, 46, 47, 48, 49, 50, 55, 60, 65, 70, 75, 80, 85, 90, or 95) % of the complement inhibitory activity of eculizumab in a hemolytic assay or CH50eq assay.

An anti-C5 antibody described herein has a serum half-life in humans that is at least 20 (e.g., at least 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, or 55) days. In another embodiment, the anti-C5 antibody described herein has a serum half-life in humans that is at least 40 days. In another embodiment, the anti-C5 antibody described herein has a serum half-life in humans that is approximately 43 days. In another embodiment, the anti-C5 antibody described herein has a serum half-life in humans that is between 39-48 days. Methods for measuring the serum half-life of an antibody are known in the art. In some embodiments, an anti-C5 antibody, or antigen binding fragment thereof, described herein has a serum half-life that is at least 20 (e.g., at least 30, 35, 40, 45, 50, 55, 60, 65, 70, 75, 80, 85, 90, 95, 100, 125, 150, 175, 200, 250, 300, 400, 500) % greater than the serum half-life of eculizumab, e.g., as measured in one of the mouse model systems described in the working examples (e.g., the C5-deficient/NOD/SCID mouse or hFcRn transgenic mouse model system).

In one embodiment, the antibody competes for binding with, and/or binds to the same epitope on C5 as the antibodies described herein. The term "binds to the same epitope" with reference to two or more antibodies means that the antibodies bind to the same segment of amino acid residues, as determined by a given method. Techniques for determining whether antibodies bind to the "same epitope on C5" with the antibodies described herein include, for example, epitope mapping methods, such as, x-ray analyses of crystals of antigen:antibody complexes, which provide atomic resolution of the epitope and hydrogen/deuterium exchange mass spectrometry (HDX-MS). Other methods monitor the binding of the antibody to peptide antigen fragments or mutated variations of the antigen where loss of binding due to a modification of an amino acid residue within the antigen sequence is often considered an indication of an epitope component. In addition, computational combinatorial methods for epitope mapping can also be used. These methods rely on the ability of the antibody of interest to affinity isolate specific short peptides from combinatorial phage display peptide libraries. Antibodies having the same VH and VL or the same CDR1, 2 and 3 sequences are expected to bind to the same epitope.

Antibodies that "compete with another antibody for binding to a target" refer to antibodies that inhibit (partially or completely) the binding of the other antibody to the target. Whether two antibodies compete with each other for binding to a target, i.e., whether and to what extent one antibody inhibits the binding of the other antibody to a target, may be determined using known competition experiments. In certain embodiments, an antibody competes with, and inhibits binding of another antibody to a target by at least 10%, 20%, 30%, 40%, 50%, 60%, 70%, 80%, 90% or 100%. The level of inhibition or competition may be different depending on which antibody is the "blocking antibody" (i.e., the cold antibody that is incubated first with the target). Competing antibodies bind to the same epitope, an overlapping epitope or to adjacent epitopes (e.g., as evidenced by steric hindrance).

Anti-C5 antibodies, or antigen-binding fragments thereof described herein, used in the methods described herein can be generated using a variety of art-recognized techniques. Monoclonal antibodies may be obtained by various techniques familiar to those skilled in the art. Briefly, spleen cells from an animal immunized with a desired antigen are immortalized, commonly by fusion with a myeloma cell (see, Kohler & Milstein, Eur. J. Immunol. 6: 511-519 (1976)). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody, or a binding fragment thereof, by screening a DNA library from human B cells according to the general protocol outlined by Huse, et al., Science 246: 1275-1281 (1989).

III. Compositions

Also, provided herein are compositions (e.g., formulations) comprising an anti-C5 antibody, or antigen binding fragment thereof, for use in the treatment methods described herein. In one embodiment, the composition comprises an anti-C5 antibody comprising the CDR1, CDR2 and CDR3 domains in a heavy chain variable region having the sequence set forth in SEQ ID NO:12, and the CDR1, CDR2 and CDR3 domains in a light chain variable region having the sequence set forth in SEQ ID NO:8. In another embodiment, the anti-C5 antibody comprises heavy and light chains having the sequences shown in SEQ ID NOs:14 and 11, respectively. In another embodiment, the anti-C5 antibody comprises heavy and light chains having the sequences shown in SEQ ID NOs:20 and 11, respectively.

The compositions can be formulated as a pharmaceutical solution, e.g., for administration to a subject for the treatment or prevention of a complement-associated condition, such as PNH. The pharmaceutical compositions will generally include a pharmaceutically acceptable carrier. As used herein, a "pharmaceutically acceptable carrier" refers to, and includes, any and all solvents, dispersion media, coatings, antibacterial and antifungal agents, isotonic and absorption delaying agents, and the like that are physiologically compatible. The compositions can include a pharmaceutically acceptable salt, e.g., an acid addition salt or a base addition salt, sugars, carbohydrates, polyols and/or tonicity modifiers.

The compositions can be formulated according to standard methods. Pharmaceutical formulation is a well-established art, and is further described in, e.g., Gennaro (2000) "Remington: The Science and Practice of Pharmacy," 20$^{th}$ Edition, Lippincott, Williams & Wilkins (ISBN: 0683306472); Ansel et al. (1999) "Pharmaceutical Dosage Forms and Drug Delivery Systems," 7$^{th}$ Edition, Lippincott Williams & Wilkins Publishers (ISBN: 0683305727); and Kibbe (2000) "Handbook of Pharmaceutical Excipients American Pharmaceutical Association," 3$^{rd}$ Edition (ISBN: 091733096X). In some embodiments, a composition can be formulated, for example, as a buffered solution at a suitable concentration and suitable for storage at 2-8° C. (e.g., 4° C.).

In some embodiments, a composition can be formulated for storage at a temperature below 0° C. (e.g., –20° C. or –80° C.). In some embodiments, the composition can be formulated for storage for up to 2 years (e.g., one month, two months, three months, four months, five months, six months, seven months, eight months, nine months, 10 months, 11 months, 1 year, 11⁄2 years, or 2 years) at 2-8° C. (e.g., 4° C.). Thus, in some embodiments, the compositions described herein are stable in storage for at least 1 year at 2-8° C. (e.g., 4° C.).

The pharmaceutical compositions can be in a variety of forms. These forms include, e.g., liquid, semi-solid and solid dosage forms, such as liquid solutions (e.g., injectable and infusible solutions), dispersions or suspensions, tablets, pills, powders, liposomes and suppositories. The preferred form depends, in part, on the intended mode of administration and therapeutic application. For example, compositions containing a composition intended for systemic or local delivery can be in the form of injectable or infusible solutions. Accordingly, the compositions can be formulated for administration by a parenteral mode (e.g., intravenous, subcutaneous, intraperitoneal, or intramuscular injection). "Parenteral administration," "administered parenterally," and other grammatically equivalent phrases, as used herein, refer to modes of administration other than enteral and topical administration, usually by injection, and include, without limitation, intravenous, intranasal, intraocular, pulmonary, intramuscular, intraarterial, intrathecal, intracapsular, intraorbital, intracardiac, intradermal, intrapulmonary, intraperitoneal, transtracheal, subcutaneous, subcuticular, intraarticular, subcapsular, subarachnoid, intraspinal, epidural, intracerebral, intracranial, intracarotid and intrasternal injection and infusion.

In one embodiment, the anti-C5 antibody, or antigen binding fragment thereof, (e.g., ravulizumab) is formulated for intravenous administration. For example, in one embodiment, the formulation for intravenous administration comprises 300 mg of ravulizumab (10 mg/mL) in 10 mM sodium phosphate, 150 mM sodium chloride, 0.02% polysorbate 80, and water for injection. In another embodiment, the formulation for intravenous administration consists of 300 mg of ravulizumab (10 mg/mL) in 10 mM sodium phosphate, 150 mM sodium chloride, 0.02% polysorbate 80, and water for injection. In another embodiment, ravulizumab for intravenous administration is formulated as a concentrated, sterile, preservative-free aqueous solution (10 mg/mL) in single-use 30 mL vials.

In one embodiment, the anti-C5 antibody, or antigen binding fragment thereof, (e.g., ravulizumab) is formulated for subcutaneous administration. For example, in one embodiment, the formulation for subcutaneous administration comprises 262.5 mg ravulizumab (70 mg/mL) in 50 mM sodium phosphate, 25 mM arginine, 5% sucrose, 0.05% polysorbate 80, and water for injection. In another embodiment, the formulation for subcutaneous administration comprises 262.5 mg ravulizumab (70 mg/mL) in 50 mM sodium phosphate, 25 mM arginine, 5% sucrose, 0.05% polysorbate 80, and water for injection. In another embodiment, the formulation for subcutaneous administration comprises 245 mg ravulizumab (70 mg/mL) in 50 mM sodium phosphate, 25 mM arginine, 5% sucrose, 0.05% polysorbate 80, and water for injection. In another embodiment, the formulation for subcutaneous administration comprises 245 mg ravulizumab (70 mg/mL) in 50 mM sodium phosphate, 25 mM arginine, 5% sucrose, 0.05% polysorbate 80, and water for injection. In another embodiment, ravulizumab for subcutaneous administration is formulated at a pH of 7.4. In another embodiment, ravulizumab for subcutaneous administration is supplied in 3.5 mL single-use cartridges. In another embodiment, each cartridge of ravulizumab for subcutaneous administration contains 262.5 mg ravulizumab (70 mg/mL) in 50 mM sodium phosphate, 25 mM arginine, 5% sucrose, 0.05% polysorbate 80, and water for injection. In another embodiment, each cartridge of ravulizumab for subcutaneous administration contains 245 mg ravulizumab (70 mg/mL) in 50 mM sodium phosphate, 25 mM arginine, 5% sucrose, 0.05% polysorbate 80, and water for injection. In another embodiment, ravulizumab for subcutaneous administration is formulated as a concentrated, sterile, preservative-free aqueous solution (70 mg/mL) in a single-use, 3.5 mL prefilled cartridge designed for use in a single-use on-body delivery system.

IV. Methods

Provided herein are compositions and methods for treating a complement-associated condition (e.g., PNH) in a human patient, comprising administering to the patient an anti-C5 antibody, or antigen binding fragment thereof, wherein the anti-C5 antibody, or antigen binding fragment thereof, is administered (or is for administration) subcutaneously according to a particular clinical dosage regimen (i.e., at a particular dose amount and according to a specific dosing schedule). In one embodiment, the patient has previously been treated with eculizumab (SOLIRIS®).

Exemplary complement-associated conditions that can be treated according to the methods described herein include, but are not limited to, rheumatoid arthritis, antiphospholipid antibody syndrome, lupus nephritis, ischemia-reperfusion injury, atypical hemolytic uremic syndrome (aHUS), typical hemolytic uremic syndrome, paroxysmal nocturnal hemoglobinuria (PNH), dense deposit disease, neuromyelitis optica spectrum disorder (NMOSD), hematopoietic stem cell transplant-associated thrombotic microangiopathy (HSCT-TMA), amyotrophic lateral sclerosis (ALS), complement mediated thrombotic microangiopathy (CM-TMA), preeclampsia hemolysis, elevated liver enzymes, low platelet count (PE-HELLP), pregnancy-induced aHUS (p-aHUS), multifocal motor neuropathy, multiple sclerosis, macular degeneration, HELLP syndrome, spontaneous fetal loss, thrombotic thrombocytopenic purpura, Pauci-immune vasculitis, epidermolysis bullosa, recurrent fetal loss, traumatic brain injury, myocarditis, a cerebrovascular disorder, a peripheral vascular disorder, a renovascular disorder, a mesenteric/enteric vascular disorder, vasculitis, Henoch-Schonlein purpura nephritis, systemic lupus erythematosus-associated vasculitis, vasculitis associated with rheumatoid arthritis, immune complex vasculitis, Takayasu's disease, dilated cardiomyopathy, diabetic angiopathy, Kawasaki's disease, venous gas embolus, restenosis following stent placement, rotational atherectomy, percutaneous transluminal coronary angioplasty, generalized myasthenia gravis (gMG), cold agglutinin disease, dermatomyositis, paroxysmal cold hemoglobinuria, antiphospholipid syndrome, Graves' disease, atherosclerosis, Alzheimer's disease, systemic inflammatory response sepsis, septic shock, spinal cord injury, glomerulonephritis, transplant rejection, Hashimoto's thyroiditis, type I diabetes, psoriasis, pemphigus, autoimmune hemolytic anemia, idiopathic thrombocytopenic purpura, Goodpasture's syndrome, Degos disease, catastrophic antiphospholipid syndrome, and severe acute respiratory syndrome coronavirus 2 (also known as "SARS-CoV-2", "COVID-19", and "coronavirus"). In a particular embodiment, the complement-associated condition is atypical hemolytic uremic syndrome (aHUS). In another particular embodiment, the complement-associated condition is paroxysmal nocturnal hemoglobinuria (PNH).

In one aspect, methods of subcutaneously administering an anti-C5 antibody, or antigen binding fragment thereof, (e.g., ravulizumab) to a patient (e.g., a PNH patient) at a dose between 400 mg-600 mg are provided. In one embodiment, the anti-C5 antibody, or antigen binding fragment thereof, is administered subcutaneously to a patient (e.g., a PNH patient) at a dose between 450-550 mg. In another embodiment, the anti-C5 antibody, or antigen binding fragment thereof, is administered subcutaneously to a patient at a dose of about 400 mg, 405 mg, 410 mg, 420 mg, 425 mg, 430 mg, 435 mg, 440 mg, 445 mg, 450 mg, 455 mg, 460 mg, 465 mg, 470 mg, 475 mg, 480 mg, 485 mg, 490 mg, 495 mg, 500 mg, 505 mg, 510 mg, 515 mg, 520 mg, 525 mg, 530 mg, 535 mg, 540 mg, 545 mg, 550 mg, 555 mg, 560 mg, 565 mg, 570 mg, 575 mg, 580 mg, 585 mg, 590 mg, 595 mg, or 600 mg. In another embodiment, the anti-C5 antibody, or antigen binding fragment thereof, is administered subcutaneously to a patient at a dose of or about 490 mg.

In another embodiment, the anti-C5 antibody, or antigen binding fragment thereof, is administered subcutaneously to a patient having a complement-associated condition (e.g., PNH) at a dose of or about 490 mg once every week (e.g., for two weeks, three weeks, one month, two months, three months, four months, five months, six months, seven months, eight months, nine months, ten months, eleven months, 1 year, 2 years, 3 years, or chronically, e.g., for the remainder of the patient's life).

In another aspect, methods of treating patients having a complement-associated condition (e.g., PNH) are provided, wherein the patient is intravenously administered an initial dose (e.g., a loading dose) of an anti-C5 antibody, or antigen binding fragment thereof (e.g., ravulizumab), followed by subcutaneous administration of the anti-C5 antibody, or antigen binding fragment thereof (e.g., two weeks later). In one embodiment, the intravenous dose of the anti-C5 antibody, or antigen binding fragment thereof, is based on the patient's weight. For example, in one embodiment, a patient weighing ≥40 to <60 kg is intravenously administered 2400 mg of the anti-C5 antibody, or antigen binding fragment thereof, prior to being treated subcutaneously with the anti-C5 antibody, or antigen binding fragment thereof. In another embodiment, a patient weighing ≥60 to <100 kg is intravenously administered 2700 mg of the anti-C5 antibody, or antigen binding fragment thereof, prior to being treated subcutaneously with the anti-C5 antibody, or antigen binding fragment thereof.

In another embodiment, a patient is intravenously administered a dose (e.g., 2400 mg or 2700 mg) of an anti-C5 antibody, or antigen binding fragment thereof, on Day 1 of an administration cycle, followed by subcutaneous administration of the anti-C5 antibody, or antigen binding fragment thereof, (e.g., at a dose of 490 mg) on Day 15 of the administration cycle and every week thereafter (e.g., for two weeks, three weeks, one month, two months, three months, four months, five months, six months, seven months, eight months, nine months, ten months, eleven months, 1 year, 2 years, 3 years, or chronically, e.g., for the remainder of the patient's life).

In another embodiment, a method of treating a human patient having a complement-associated condition (e.g., PNH) is provided, the method comprising administering to the patient during an administration cycle an effective amount of an anti-C5 antibody, or antigen binding fragment thereof, wherein the anti-C5 antibody, or antigen binding fragment thereof, is administered:
(a) intravenously once on Day 1 of the administration cycle at a dose of:
    i. 2400 mg to a patient weighing ≥40 to <60 kg, or
    ii. 2700 mg to a patient weighing ≥60 to <100 kg; and
(b) subcutaneously on Day 15 of the administration cycle and every week thereafter at a dose of 490 mg.

In another embodiment, the anti-C5 antibody, or antigen binding fragment thereof, is administered to a patient (e.g., PNH patient) weighing ≥40 to <60 kg: (a) intravenously once on Day 1 of the administration cycle at a dose of 2400 mg and (b) subcutaneously on Day 15 of the administration cycle and every week thereafter at a dose of 490 mg.

In another embodiment, the anti-C5 antibody, or antigen binding fragment thereof, is administered to a patient (e.g., PNH patient) weighing ≥60 to <100 kg: (a) intravenously once on Day 1 of the administration cycle at a dose of 2700 mg and (b) subcutaneously on Day 15 of the administration cycle and every week thereafter at a dose of 490 mg.

In another embodiment, a method of treating a human patient having a complement-associated condition is provided, the method comprising administering to the patient during an administration cycle an effective amount of an anti-C5 antibody, or antigen binding fragment thereof, comprising CDR1, CDR2, and CDR3 heavy chain sequences as set forth in SEQ ID NOs:19, 18, and 3, respectively, and CDR1, CDR2, and CDR3 light chain sequences as set forth in SEQ ID NOs:4, 5, and 6, respectively, wherein the anti-C5 antibody, or antigen binding fragment thereof, is administered:
(a) intravenously once on Day 1 of the administration cycle at a dose of:
    i. 2400 mg to a patient weighing ≥40 to <60 kg, or
    ii. 2700 mg to a patient weighing ≥60 to <100 kg; and
(b) subcutaneously on Day 15 of the administration cycle and every week thereafter at a dose of 490 mg.

In another embodiment, a method of treating a human patient with a complement associated condition (e.g., PNH), is provided, the method comprising administering to the patient during an administration cycle an effective amount of an anti-C5 antibody, or antigen binding fragment thereof, comprising CDR1, CDR2, and CDR3 heavy chain sequences as set forth in SEQ ID NOs:19, 18, and 3, respectively, CDR1, CDR2, and CDR3 light chain sequences as set forth in SEQ ID NOs:4, 5, and 6, respectively, and a variant human Fc constant region that binds to human neonatal Fc receptor (FcRn), wherein the variant human Fc CH3 constant region comprises Met-429-Leu and Asn-435-Ser substitutions at residues corresponding to methionine 428 and asparagine 434 of a native human IgG Fc constant region, each in EU numbering, wherein the anti-C5 antibody, or antigen binding fragment thereof, is administered:
(a) intravenously on Day 1 of the administration cycle at a dose of:
    i. 2400 mg to a patient weighing ≥40 to <60 kg, or
    ii. 2700 mg to a patient weighing ≥60 to <100 kg; and
(b) subcutaneously on Day 15 of the administration cycle and every week thereafter at a dose of 490 mg.

In one embodiment, an administration cycle is 10 total weeks of treatment. In another embodiment, the anti-C5 antibody, or antigen binding fragment thereof, is administered subcutaneously at a dose of 490 mg once weekly after the administration cycle for up to 3 months, 6 months, 9 months, 12 months, 15 months, 18 months, 21 months, two years, or chronically, e.g., for the remainder of the patient's life.

In some embodiments, the patients treated according to the methods described herein have previously been treated with a complement inhibitor. In one embodiment, the patient has previously been treated with eculizumab. In another embodiment, the patient has previously been treated for at least 1 month, at least 2 months, at least 3 months, at least 4 months, at least 5 months, at least 6 months, at least 7 months, at least 8 months, at least 9 months, at least 10 months, at least 11 months, at least 12 months, at least 18 months, or at least 24 months with eculizumab. In a particular embodiment, the patient has previously been treated for at least 6 months with eculizumab. In another embodiment, the anti-C5 antibody, or antigen binding fragment thereof, (e.g., ravulizumab) is administered to a patient, where in the patient has been treated with eculizumab for at least about 1 month, at least about 2 months, at least about 3 months, at least about 4 months, at least about 5 months, at least about 6 months, at least about 7 months, at least about 8 months, at least about 9 months, at least about 10 months, at least about 11, months, or at least about 12 months prior to Day 1 of the administration cycle. In another embodiment, the anti-C5 antibody, or antigen binding fragment thereof, is administered to a patient, where in the patient has been treated with eculizumab for at least about 1 year prior to Day 1 of the administration cycle. In another embodiment, the anti-C5 antibody, or antigen binding fragment thereof, is administered to a patient, where in the patient has been treated with eculizumab for at least about 6 months prior to Day 1 of the administration cycle.

In some embodiments, an anti-C5 antibody, or antigen binding fragment thereof, is administered to a patient, wherein the patient has previously been treated with eculizumab at a dose of about 600 mg, about 700 mg, about 800 mg, or about 900 mg every 2 weeks. In another embodiment, the anti-C5 antibody, or antigen binding fragment thereof, is administered to a patient, wherein the patient has previously been treated with eculizumab at a dose of about 900 mg every 2 weeks ([q2w]).

In some embodiment, the anti-C5 antibody, or antigen binding fragment thereof (e.g., ravulizumab), is administered to a patient, wherein the administration cycle starts at least about two weeks, at least about three weeks, at least about four weeks, at least about six weeks, at least about seven weeks, or at least about eight weeks after the patient's last dose of eculizumab. In another embodiment, the anti-C5 antibody, or antigen binding fragment thereof (e.g., ravulizumab), is administered to a patient, wherein the administration cycle starts at least two weeks after the patient's last dose of eculizumab.

In some embodiments, the patients treated according to the methods described herein have been vaccinated against meningococcal infections within 3 years prior to, or at the time of, initiating treatment. In one embodiment, patients who received treatment less than 2 weeks after receiving a meningococcal vaccine are also treated with appropriate prophylactic antibiotics until 2 weeks after vaccination. In another embodiment, patients treated according to the methods described herein are vaccinated against meningococcal serotypes A, C, Y, W135, and/or B.

In another aspect, the treatment regimens described are sufficient to maintain particular serum trough concentrations of the anti-C5 antibody, or antigen binding fragment thereof. For example, in one embodiment, the treatment maintains a serum trough concentration of the anti-C5 antibody, or antigen binding fragment thereof, of 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, or 400 µg/ml or greater. In one embodiment, the treatment maintains a serum trough concentration of the anti-C5 antibody, or antigen binding fragment thereof, of 100 µg/ml or greater. In another embodiment, the treatment maintains a serum trough concentration of the anti-C5 antibody, or antigen binding fragment thereof, of 150 µg/ml or greater. In another embodiment, the treatment maintains a serum trough concentration of the anti-C5 antibody, or antigen binding fragment thereof, of 200 µg/ml or greater. In another embodiment, the treatment maintains a serum trough concentration of the anti-C5 antibody, or antigen binding fragment thereof, of 250 µg/ml or greater. In another embodiment, the treatment maintains a serum trough concentration of the anti-C5 antibody, or antigen binding fragment thereof, of 300 µg/ml or greater. In another embodiment, the treatment maintains a serum trough concentration of the anti-C5 antibody, or antigen binding fragment thereof, of between 100 µg/ml and 200 µg/ml. In another embodiment, the treatment maintains a serum trough concentration of the anti-C5 antibody, or antigen binding fragment thereof, of about 175 µg/ml.

In another embodiment, to obtain an effective response, the anti-C5 antibody is administered to the patient in an amount and with a frequency to maintain at least 50 µg, 55 µg, 60 µg, 65 µg, 70 µg, 75 µg, 80 µg, 85 µg, 90 µg, 95 µg, 100 µg, 105 µg, 110 µg, 115 µg, 120 µg, 125 µg, 130 µg, 135 µg, 140 µg, 145 µg, 150 µg, 155 µg, 160 µg, 165 µg, 170 µg, 175 µg, 180 g, 185 µg, 190 µg, 195 µg, 200 µg, 205 µg, 210 µg, 215 µg, 220 µg, 225 µg, 230 µg, 235 µg, 240 µg, 245 µg, 250 µg, 255 µg, or 260 µg of antibody per milliliter of the patient's blood. In another embodiment, the anti-C5 antibody is administered to the patient in an amount and with a frequency to maintain between 50 µg and 250 µg of antibody per milliliter of the patient's blood. In another embodiment, the anti-C5 antibody is administered to the patient in an amount and with a frequency to maintain between 100 µg and 200 µg of antibody per milliliter of the patient's blood. In another embodiment, the anti-C5 antibody is administered to the patient in an amount and with a frequency to maintain about 175 µg of antibody per milliliter of the patient's blood.

V. Outcomes

Symptoms of PNH include, but are not limited to, fatigue (e.g., tiredness, difficultly performing daily activities, trouble concentrating, dizziness, weakness), pain (e.g., stomach pain, leg pain or swelling, chest pain, back pain), dark-colored urine, shortness of breath, anemia, difficulty swallowing, yellowing of the skin and/or eyes, erectile dysfunction, blood clots, kidney disease, damage to organs, stroke, or heart attack. Patients treated according to the methods disclosed herein preferably experience improvement in at least one sign of PNH. For example, the treatment may produce at least one therapeutic effect selected from the group consisting of a reduction or cessation in fatigue, abdominal pain, dyspnea, dysphagia, chest pain, and erectile dysfunction.

LDH is a marker of intravascular hemolysis (Hill, A. et al., *Br. J. Haematol.*, 149:414-25, 2010; Hillmen, P. et al., *N. Engl. J Med.*, 350:552-9, 2004; Parker, C. et al., *Blood*, 106:3699-709, 2005). Red blood cells contain large amounts of LDH, and a correlation between cell-free hemoglobin and LDH concentration has been reported in vitro (Van Lente, F. et al., *Clin. Chem.,* 27:1453-5, 1981) and in vivo (Kato, G. et al., *Blood,* 107:2279-85, 2006). The consequences of hemolysis are independent of anemia (Hill, A. et al., *Hae-matologica,* 93(sl):359 Abs.0903, 2008; Kanakura, Y et al., *Int. J. Hematol.,* 93:36-46, 2011). LDH concentration obtained at baseline and then serially throughout a treatment period is an important measure of hemolysis. Baseline levels of cell-free plasma hemoglobin are highly elevated in patients with PNH with LDH≥1.5-fold above the upper limit of normal (LDH≥1.5×ULN), with a significant correlation between LDH and cell-free plasma hemoglobin (Hillmen, P. et al., *N. Engl. J. Med.,* 355:1233-43, 2006). The normal LDH value range is 105-333 IU/L (international units per liter).

Published data support LDH as a reliable, objective, and direct measure of intravascular hemolysis in patients with PNH and is considered by experts to be the best measure of complement-mediated hemolysis, the hallmark of PNH disease activity (Dale J. et al., *Acta Med Scand.,* 191(1-2):133-136, 1972; Parker C. et al., *Blood.* 106(12):3699-3709, 2005; Canalejo K et al., *Int J Lab Hemat.,* 36(2):1213-1221, 2013). Results from the eculizumab clinical program showed that LDH concentrations remained markedly elevated and unchanged in untreated (placebo) patients, while eculizumab-treated patients had an immediate reduction (within 1 week following initiation of treatment) in serum LDH to normal or near normal levels (Brodsky R A et al., *Blood,* 111(4):1840-1847, 2008; Hillmen P et al., *Am J Hematol.,* 85(8):553-559, 2010. Erratum in Am J Hematol. 2010; 85(11):911). This reduction mirrored a rapid reduction in symptoms and improvement in fatigue (Hillmen P et al., *Am J Hematol.,* 85(8):553-559, 2010; Brodsky R A et al., *Blood,* 111(4):1840-1847, 2008).

LDH levels can be measured using any suitable test or assay, such as those described by Ferri F F, ed. *Ferri's ClinicalAdvisor* 2014. *Philadelphia: Pa: Elsevier Mosby;* 2014: Section IV-Laboratory tests and interpretation of results. LDH concentration can be measured in various samples obtained from a patient, in particular, serum samples. As used herein, the term "sample" refers to biological material from a subject. Although serum LDH concentration is of interest, samples can be derived from other sources, including, for example, single cells, multiple cells, tissues, tumors, biological fluids, biological molecules or supernatants or extracts of any of the foregoing. Examples include tissue removed for biopsy, tissue removed during resection, blood, urine, lymph tissue, lymph fluid, cerebro-spinal fluid, mucous, and stool samples. The sample used will vary based on the assay format, the detection method and the nature of the tumors, tissues, cells or extracts to be assayed. Methods for preparing samples are known in the art and can be readily adapted to obtain a sample that is compatible with the method utilized.

In one embodiment, LDH levels are used to evaluate responsiveness to a therapy (e.g., a reduction of hemolysis as assessed by LDH levels is indicative of an improvement in at least one sign of PNH). For example, in one embodiment, the treatments described herein result in a normalization of LDH levels. In another embodiment, patients treated according to the disclosed methods experience reductions in LDH levels to near normal levels or to within 10%, or within 20% above what is considered the normal level (e.g., within 105-333 IU/L (international units per liter). In another embodiment, the patient's LDH levels are ≥1.5 fold above the upper limit of normal (LDH≥1.5×ULN) prior to initiating treatment. In another embodiment, the patient's LDH levels are normalized throughout the maintenance period of treatment. In another embodiment, the treated patient's LDH levels are normalized at least 95% of the time while on the maintenance period of treatment. In another embodiment, the treated patient's LDH levels are normalized at least 90%, 85% or 80% of the time while on the maintenance period of treatment. In one embodiment, the patient's LDH levels are ≥1.5 fold above the upper limit of normal (LDH≥1.5×ULN) prior to initiating treatment.

In another embodiment, the treatment results in a reduction in breakthrough hemolysis relative to treatment with eculizumab. In another embodiment, the treatment results in an elimination of breakthrough hemolysis during the treatment period. In another embodiment, the treatment results in a reduction of breakthrough hemolysis compared to pretreatment baseline amount of breakthrough hemolysis.

In another embodiment, the treatment produces a reduction in the need for blood transfusions. In another embodiment, the treatment produces an increase in transfusion avoidance. In another embodiment, the treatment produces an increase of at least 50% in transfusion avoidance. In another embodiment, the treatment produces an increase of at least 60% in transfusion avoidance. In another embodiment, the treatment produces a greater than 70% increase in transfusion avoidance. In all cases the transfusion avoidance is measured against pretreatment frequency for the requirement to receive transfusions.

In another embodiment, the treatment produces a reduction in major adverse vascular events (MAVEs) (e.g., thrombophlebitis/deep vein thrombosis, pulmonary embolus, myocardial infarction, transient ischemic attack, unstable angina, renal vein thrombosis/renal artery thrombosis/glomerular thrombosis, renal infarction, acute peripheral vascular occlusion, mesenteric/visceral vein/arterial thrombosis or infarction, hepatic/portal vein thrombosis, cerebral arterial occlusion/cerebrovascular accident, cerebral venous occlusion, renal arterial thrombosis, or multi-infarct dementia), as described in further detail in the Examples. In another embodiment, the treatment produces a shift toward normal levels of a hemolysis-related hematologic biomarker selected from the group consisting of free hemoglobin, haptoglobin, reticulocyte count, PNH red blood cell (RBC) clone and D-dimer. In another embodiment, the treatment produces an increase in hemoglobin stabilization from the patient's pre-treatment baseline.

In another embodiment, the treatment produces a shift toward normal levels of a chronic disease associated biomarker selected from the group consisting estimated glomerular filtration rate (eGFR) and spot urine:albumin:creatinine and plasma brain natriuretic peptide (BNP).

In another embodiment, the treatment produces a change from baseline in quality of life as assessed via the Functional Assessment of Chronic Illness Therapy (FACIT)-Fatigue Scale, version 4 and the European Organisation for Research and Treatment of Cancer, Quality of Life Questionnaire-Core 30 Scale, and described in further detail in the Examples. In another embodiment, the treatment produces a change from baseline in quality of life, as assessed via the Functional Assessment of Chronic Illness Therapy (FACIT)-Fatigue Scale, version 4 and the European Organisation for Research and Treatment of Cancer, Quality of Life Questionnaire-Core 30 Scale by at least 7 points from the patients untreated baseline score.

VI. Kits

Also provided herein are kits which include a pharmaceutical composition containing an anti-C5 antibody, or antigen binding fragment thereof, such as ravulizumab, and a pharmaceutically-acceptable carrier, in a therapeutically effective amount adapted for use in the preceding methods. The kits optionally also can include instructions, e.g., comprising administration schedules, to allow a practitioner (e.g., a physician, nurse, or patient) to administer the composition contained therein to administer the composition to a patient having a complement-associated condition (e.g., PNH). The kit also can include a syringe or an on-body delivery system (OBDS). In one embodiment, the OBDS is the SmartDose® Drug Delivery Platform. In another embodiment, the ravulizumab is administered by subcutaneous injection via the single-use OBDS using the West SmartDose® Gen. I 3.5 mL.

In one embodiment, a kit for treating a complement-associated condition (e.g., PNH) in a human patient is provided, the kit comprising: (a) a dose of an anti-C5 antibody, or antigen binding fragment thereof, comprising CDR1, CDR2 and CDR3 domains of the heavy chain variable region having the sequence set forth in SEQ ID NO:12, and CDR1, CDR2 and CDR3 domains of the light chain variable region having the sequence set forth in SEQ ID NO:8; and (b) instructions for using the anti-C5 antibody, or antigen binding fragment thereof, in the methods described herein. In one embodiment, the anti-C5 antibody, or antigen binding fragment thereof, is administered to a patient weighing ≥40 to <60 kg: (a) intravenously once on Day 1 of the administration cycle at a dose of 2400 mg; and (b) subcutaneously on Day 15 of the administration cycle and every week thereafter at a dose of 490 mg. In another embodiment, the anti-C5 antibody, or antigen binding fragment thereof, is administered to a patient weighing ≥60 to <100 kg: (a) intravenously once on Day 1 of the administration cycle at a dose of 2700 mg; and (b) subcutaneously on Day 15 of the administration cycle and every week thereafter at a dose of 490 mg. In a particular embodiment, the anti-C5 antibody is ravulizumab.

VII. Devices

Further provided is a device (e.g., an on-body delivery system (OBDS) comprising a prefilled cartridge of ravulizumab for subcutaneous administration co-packaged with an on-body injector. In one embodiment, the device is sterile, for single use, disposable, and/or electro-mechanical. In another embodiment, the on-body injector comprises a 29-gauge needle. In another embodiment, the prefilled cartridge is a 3.5 mL cartridge. In another embodiment, ravulizumab for subcutaneous administration comprises 262.5 mg ravulizumab (70 mg/mL) in 50 mM sodium phosphate, 25 mM arginine, 5% sucrose, 0.05% polysorbate 80, and water for injection. In another embodiment, ravulizumab for subcutaneous administration consists of 262.5 mg ravulizumab (70 mg/mL) in 50 mM sodium phosphate, 25 mM arginine, 5% sucrose, 0.05% polysorbate 80, and water for injection. In another embodiment, ravulizumab for subcutaneous administration comprises 245 mg ravulizumab (70 mg/mL) in 50 mM sodium phosphate, 25 mM arginine, 5% sucrose, 0.05% polysorbate 80, and water for injection. In another embodiment, ravulizumab for subcutaneous administration consists of 245 mg ravulizumab (70 mg/mL) in 50 mM sodium phosphate, 25 mM arginine, 5% sucrose, 0.05% polysorbate 80, and water for injection. In another embodiment, ravulizumab for subcutaneous administration is formulated at a pH of about 7.4.

An exemplary device for use in conjunction with ravulizumab for subcutaneous administration as described herein is the on-body delivery system (OBDS) manufactured by West Pharmaceuticals, Inc., which is currently approved for use with evolocumab (Repatha®) as a combination agent in the United States and CE marked in the European Union as a class IIA Medical Device. In one embodiment, the OBDS is the SmartDose® Drug Delivery Platform (see, worldwide-web at westpharma(dot)com/products/self-injection-platforms/smartdose/smartdose-gen-I; West Catalog #11262 0919 (2019)). In another embodiment, the device is a compact, sterile, single-use, disposable, electro-mechanical (battery powered, microprocessor controlled), investigational medical device with a 29-gauge integrated needle (manufactured by West Pharmaceuticals, Inc.) designed to be used together with a prefilled stoppered Crystal Zenith® cartridge with a piston and telescopic screw assembly (TSA). In another embodiment, the ravulizumab is administered by subcutaneous injection via the single-use OBDS using the West SmartDose® Gen. I 3.5 mL. In another embodiment, the OBDS is the complete co-packaged combination product consisting of the Device Constituent for the Drug Delivery platform, and the prefilled cartridge (PFC) containing 3.5 mL ravulizumab 70 mg/mL, with an assembled TSA. In another embodiment, the "On-body injector" is only the device constituent (the OBDS without the PFC and TSA). In another embodiment, user interaction is required to activate the OBDS, such as activation force. In another embodiment, a design requirement at point of use and essential to achieve intended use (e.g., deliverable volume/dose accuracy) is an essential performance requirement irrespective of the associated risk/severity level (low or high). In another embodiment, an essential performance requirement is a delivery status notification at end of injection (i.e., successful or unsuccessful delivery notification to the user).

The following examples are merely illustrative and should not be construed as limiting the scope of this disclosure in any way as many variations and equivalents will become apparent to those skilled in the art upon reading the present disclosure.

The contents of all references, GENBANK/UNIPROT/PUBMED entries, patents and published patent applications cited throughout this application are expressly incorporated herein by reference.

EXAMPLES

Example 1: Phase 3 Clinical Trial

A Phase 3, randomized, parallel-group, multicenter, open-label, pharmacokinetic, noninferiority study of ravulizumab administered subcutaneously versus intravenously in adult patients with paroxysmal nocturnal hemoglobinuria (PNH) currently treated with eculizumab is conducted according to the following protocol.

The purpose of this study is to compare the pharmacokinetics (PK) of ravulizumab subcutaneous (SC) administered via an on-body delivery system (OBDS) to ravulizumab intravenous (IV) in patients with paroxysmal nocturnal hemoglobinuria (PNH) who are clinically stable and have been previously treated with eculizumab for at least 3 months prior to study entry. Based on the established relationship between PK exposure and clinical efficacy of ravulizumab IV, the PK noninferiority of ravulizumab SC to ravulizumab IV enables bridging of efficacy and safety data from ravulizumab IV to ravulizumab SC. The study hypothesis is that Day 71 ravulizumab SC serum $C_{trough}$ is noninferior compared with Day 71 ravulizumab IV serum $C_{trough}$. The study is also intended to demonstrate the safety and tolerability of ravulizumab SC and the ravulizumab OBDS, a drug-device combination product.

1. Objectives and Endpoints

The primary objective of the study is to evaluate PK noninferiority of ravulizumab SC versus ravulizumab IV in adult patients with PNH (e.g., as assessed by Day 71 serum ravulizumab $C_{trough}$ (predose concentration).

Secondary objectives include (1) characterizing PK of ravulizumab SC (e.g., as assessed By $C_{trough}$ over time (2) characterizing PD of ravulizumab SC (e.g., as assessed by free serum C5 concentrations over time), (3) characterizing immunogenicity of ravulizumab SC (e.g., as assessed by incidence of treatment-emergent antidrug antibodies (ADAs) over time, (4) evaluating health-related quality of life (HRQoL) and treatment satisfaction on ravulizumab subcutaneous (SC) (e.g., as assessed by (a) change in Functional Assessment of Chronic Illness Therapy (FACIT)-Fatigue Scale, Version 4, from Baseline to Day 183, (b) change in European Organisation for Research and Treatment of Cancer (EORTC) Quality of Life Questionnaire-Core 30 Scale (QLQ-C30) Version 3.0, from Baseline to Day 183, and (c) reported treatment satisfaction and patient preference as measured by the Treatment Administration Satisfaction Questionnaire (TASQ) score at Baseline and Day 183), (5) evaluating safety of ravulizumab SC and ravulizumab OBDS (e.g., as assessed by (a) change in physical examinations, vital signs, electrocardiograms, and laboratory assessments over time, (b) incidence of adverse events and serious adverse events, and (c) incidence of adverse device effects and serious adverse device effects), (6) evaluating efficacy of ravulizumab SC (e.g., as assessed by (a) change over time in lactate dehydrogenase (LDH), (b) incidence of breakthrough hemolysis, (c) achievement of transfusion avoidance, and (d) achievement of stabilized hemoglobin), and (7) assessing performance of ravulizumab OBDS (e.g., as assessed by reported outcome of attempted full-dose administration (including device failure/malfunction)).

2. Overall Design

This is a Phase 3, randomized, open-label, parallel-group, multicenter study to evaluate PK noninferiority of ravulizumab SC administered via an OBDS compared with intravenously administered ravulizumab IV in adult patients with PNH who are clinically stable and have been previously treated with eculizumab for at least 3 months prior to study entry.

The study consists of an up to a 30-day Screening Period, a 10-week Randomized Treatment Period, and an Extension Period of up to 3.5 years (182 weeks) or until the product is registered or approved (in accordance with country-specific regulations), whichever occurs first. Patients are stratified by weight group (≥40 kg to <60 kg and >60 kg to <100 kg) and then randomized in a 2:1 ratio to receive either ravulizumab SC or ravulizumab IV.

Ravulizumab IV dosing during the Randomized Treatment Period is administered in the clinic by a trained member of the site study team. Day 1 of study treatment occurs 12 to 16 days from the patient's last dose of eculizumab. Timing for study drug administration and predose PK sample collection is critical to ensure adequate numbers of patients with evaluable PK data (Table 1). The time for the start of the dose administered on Day 1 is the nominal time for all subsequent doses and PK/PD sample collections. Specifically, all subsequent doses during the Randomized Treatment Period are administered at the same time of day that the dose was administered on Day 1. The PK samples are drawn as close as possible to the administration of the dose (or from the nominal time from the start of the Day 1 dose on nondosing days).

Ravulizumab OBDS is supplied in a kit, comprising 245 mg of ravulizumab SC in a sterile, single-use, prefilled cartridge assembly copackaged with a single-use injector. Two kits are used to deliver the full 490 mg dose of ravulizumab SC.

Ravulizumab IV loading and maintenance doses are based on patient body weight prior to dosing at each dosing visit, as set forth in Table 1.

During the Randomized Treatment Period, patients assigned to the ravulizumab SC group receive a loading dose of ravulizumab IV on Day 1, followed by maintenance doses of ravulizumab SC on Day 15 and every week (qw) thereafter through completion of the Randomized Treatment Period. Patients assigned to the ravulizumab IV group receive a loading dose of ravulizumab IV on Day 1 followed by a maintenance dose of ravulizumab IV on Day 15, as set forth in Table 1.

TABLE 1

| | Study Drug Dosing | | |
|---|---|---|---|
| Treatment Group | Randomized Treatment Period (10 weeks) | | Extension Period (up to 182 weeks) |
| Ravulizumab SC | Loading Dose on Day 1: Ravulizumab IV 2400 mg[a] or Ravulizumab IV 2700 mg[b] | SC Doses on Days 15, 22, 29, 36, 43, 50, 57, and 64: Ravulizumab SC 490 mg[c] (2 ravulizumab OBDS kits per weekly dose) | Maintenance Doses on Day 71 and every week (qw) through Day 1275: Ravulizumab SC 490 mg[d] (2 ravulizumab OBDS kits per weekly dose) |
| Ravulizumab IV | | Maintenance Dose on Day 15: Ravulizumab IV 3000 mg[a] or Ravulizumab IV 3300 mg[b] | |

[a]Weight group ≥40 to <60 kg.

[b]Weight group ≥60 to <100 kg.

[c]On Day 15, patients who randomized to the ravulizumab SC group self-administer ravulizumab SC in the clinic with oversight by trained study site personnel as part of the required training program for at-home self-administration. On Days 29, 43, 57, and 64, ravulizumab SC is self-administered by the patient in the clinic with oversight by trained study site personnel. On Days 22, 36, and 50, ravulizumab dosing can be self-administered by the patient at home. With approval, the patient can self-administer ravulizumab SC at the clinic at these visits.

[d]Self-administered by the patient at home or self-administered in the clinic with oversight by trained study site personnel on scheduled visit days. With approval, the patient can self-administer ravulizumab SC at the clinic on dosing days that are not scheduled in-clinic visits. On Day 71, patients who had been randomized to the ravulizumab IV group self-administer ravulizumab SC in the clinic with oversight by trained study site personnel as part of the required training program for at-home self-administration.

Day 71 is the end of the Randomized Treatment Period and the beginning of the Extension Period. All Day 71 assessments completed prior to dosing are considered part of the Randomized Treatment Period. Dosing on Day 71 is the start of the Extension Period. During the Extension Period, patients who had been randomized to the ravulizumab SC group continue to receive 490 mg of ravulizumab SC using 2 OBDS kits on Day 71 and every week thereafter through the end of the Extension Period (up to Day 1275). Patients who had been randomized to the ravulizumab IV group switch to 490 mg of ravulizumab SC using 2 OBDS kits on Day 71 and every week thereafter through the end of the Extension Period (up to Day 1275) Ravulizumab SC dosing during the Extension Period can be self-administered by the patient at home with the following exceptions where ravulizumab SC is administered in the clinic. For patients who had been randomized to the ravulizumab IV group, ravulizumab SC 490 mg dose on Day 71 is self-administered by the patient in the clinic with oversight by trained study site personnel as part of the required training program for at-home self-administration. For all patients, doses that coincide with study visits specified in the Schedule of Activities are self-administered by the patient in the clinic with oversight by trained study site personnel. With approval, the patient can self-administer ravulizumab SC at the clinic on dosing days that are not scheduled in-clinic visits (with oversight by trained study site personnel).

The end of the study for each patient occurs when the safety follow-up is completed. The safety follow-up consists of a phone call 30 days after the last dose. Data collection during the safety follow-up is limited to reporting adverse events and concomitant medications. If a patient discontinues treatment, but does not discontinue from the study, the end of study for such a patient is their last visit as long as that visit is more than 30 days from their last dose. The end of the study is defined as the date of the last patient visit or safety follow up, whichever occurs later.

Approximately 105 patients (70 patients in the ravulizumab SC group and 35 patients in the ravulizumab IV group) are enrolled in the study. An interim analysis for sample size re-estimation is conducted and the sample size can be increased to a maximum of 144 patients.

3. Inclusion and Exclusion Criteria

Patients must meet all inclusion and no exclusion criteria. Patients who fail study eligibility may be rescreened once based on discussion and agreement. Patients are eligible to be included in the study only if they fulfill all of the following criteria:

A. Patients must be at least 18 years of age at the time of signing the informed consent.

B. Treated with eculizumab according to the labeled dosing recommendation for PNH (900 mg every 14 days+2 days) for at least 3 months prior to study entry with no missed doses within 2 months prior to study entry and no more than 2 doses outside of the visit window.

C. Lactate dehydrogenase levels ≤1.5×ULN (upper limit of normal), according to central laboratory, at Screening. Sample must be obtained within 24 hours of or immediately prior to a scheduled eculizumab dose administration (i.e., at trough eculizumab level).

D. Documented diagnosis of PNH confirmed by high-sensitivity flow cytometry evaluation (see, e.g., Borowitz et al., "Guidelines for the diagnosis and monitoring of paroxysmal nocturnal hemoglobinuria and related disorders by flow cytometry", Cytometry B. Clin. Cytom. 2010; 78(4):211-230).

E. Vaccinated against meningococcal infections within 3 years prior to, or at the time of, initiating study drug to reduce the risk of meningococcal infection (*N meningitidis*).

F. Body weight ≥40 to <100 kg, and likely to remain within this body weight range for the duration of the study.

G. Female patients of childbearing potential and male patients with female partners of childbearing potential must follow protocol-specified contraception guidance while on treatment and for at least 8 months after last dose of study drug.

H. Patients must be willing and able to give written informed consent and to comply with all study visits and procedures, including self-administration of ravulizumab SC doses, and the use of any data collection device(s) to directly record patient data.

Patients are excluded from the study if any of the following criteria are met:

A. More than 1 LDH value >2×ULN within the 3 months prior to study entry.

B. Major adverse vascular event (MAVE) in the 6 months prior to study entry.

C. Platelet count <30,000/mm$^3$ (30×10$^9$/L) at Screening.

D. Absolute neutrophil count <500/μL (0.5×10$^9$/L) at Screening.

E. History of bone marrow transplantation.

F. History of *N meningitidis* infection.

G. History of unexplained infections.

H. Active systemic bacterial, viral, or fungal infection within 14 days prior to study drug administration on Day 1.

I. Presence of fever ≥38° C. (100.4° F.) within 7 days prior to study drug administration on Day 1.

J. Human immunodeficiency virus (HIV) infection (evidenced by HIV-1 or HIV-2 antibody titer).

K. History of malignancy within 5 years of Screening with the exception of nonmelanoma skin cancer or carcinoma in situ of the cervix that has been treated with no evidence of recurrence.

L. History of or ongoing major cardiac, pulmonary, renal, endocrine, or hepatic disease (e.g., active hepatitis) that precludes the patient's participation in an investigational clinical study.

M. Unstable medical conditions (e.g., myocardial ischemia, active gastrointestinal bleed, severe congestive heart failure, anticipated need for major surgery within 6 months of Day 1, coexisting chronic anemia unrelated to PNH) that would make patients unlikely to tolerate the requirements of the protocol).

N. History of hypersensitivity to any ingredient contained in the study drug including hypersensitivity to murine proteins.

O. Female patients who plan to become pregnant or are currently pregnant or breastfeeding.

P. Female patients who have a positive pregnancy test result at screening or on Day 1.

Q. Known medical or psychological condition(s) or risk factor that might interfere with the patient's full participation in the study, pose an additional risk for the patient, or confound the outcome of the study.

R. Known or suspected history of drug or alcohol abuse or dependence within 1 year prior to Screening.

S. Inability to complete the requirements for SC self-administration.

T. Inability to travel to the clinic for specified visits during the Randomized Treatment Period or fulfill the logistic requirements of study drug.

U. Concomitant use of anticoagulants is prohibited if not on a stable regimen for at least 2 weeks prior to study entry.

V. Participation in another study or use of any experimental therapy within 30 days before initiation of study drug on Day 1 in this study or within 5 half-lives of that investigational product, whichever is greater (except for participation in observational studies [e.g., PNH Registry]).

W. Received any other experimental C5 antagonist at any time.

4. Schedule of Activities

The Schedule of Activities (SoA) for Screening and the Randomized Treatment Period is provided for the ravulizumab SC group in Table 2 for the ravulizumab IV group in Table 3. Day 71 is the end of the Randomized Treatment Period. All assessments for Day 71 are performed prior to dosing. On Day 15, a qualified member of the site study team trains patients randomized to ravulizumab SC on self-administration of ravulizumab SC using the OBDS kits prior to self-administration by the patient. The patient self-administers the Day 15 dose of ravulizumab SC in the clinic with oversight by trained study site personnel. On Days 22, 36, and 50, ravulizumab SC can be self-administered by the patient at home. With approval, the patient can self-administer ravulizumab SC at the clinic on these days (with oversight by trained study site personnel). On Days 29, 43, 57, and 64, ravulizumab SC is self-administered by the patient in the clinic with oversight by trained study site personnel.

The Schedule of Assessments for the Extension Period is provided in Table 4 and Table 5. Dosing on Day 71 is the start of the Extension Period. The first dose of ravulizumab SC for patients who had been randomized to ravulizumab IV during the Randomized Treatment Period is on Day 71. On Day 71, a qualified member of the site study team trains patients who had been randomized to ravulizumab IV on self-administration of ravulizumab SC using the OBDS kits prior to self-administration by the patient. The patient self-administers the Day 71 dose of ravulizumab SC in the clinic with oversight by trained study site personnel. For patients who had been randomized to ravulizumab SC, dosing on Day 71 is by self-administration during the in-clinic visit. For the remainder of the Extension Period, weekly dosing of ravulizumab SC for all patients can be by self-administration by the patient at home or in the clinic at visits specified in Table 4 and Table 5. With approval, the patient can self-administer ravulizumab SC at the clinic on dosing days that are not scheduled in-clinic visits (with oversight by trained study site personnel).

Procedures conducted as part of the patient's routine clinical management (e.g., hematology assessments) and obtained before signing of the informed consent form (ICF) may be utilized for screening purposes provided the procedures meet protocol-specified criteria and were performed within the time frame specified in the Schedule of Assessments.

Quality of life assessments are administered and recorded on paper throughout the study. Data associated with ravulizumab SC dosing when it is administered in the home setting during the Extension Period is recorded in a patient e-diary.

The site monitors self-administration of ravulizumab SC by the patient via telephone calls with the patient on scheduled at-home dosing days during the Randomized Treatment Period (patients randomized to ravulizumab SC) to ensure that the patient is queried about study drug dose administered and device condition. During the Extension Period, the site contacts patients by telephone on Day 78 to query the patient on study drug administration and completion of the patient e-diary. After Day 78, sites monitor self-administration of ravulizumab SC via the patient e-diary.

Laboratory specimen handling and processing instructions are provided in the study laboratory manual. Blood samples are not collected from a heparinized line. Post IV dose (Day 1 for both cohorts, and also Day 15 for the ravulizumab IV cohort) blood samples should be collected from the contralateral arm.

Unscheduled visits that occur outside the protocol-specified visits are permitted with discretion. Procedures, tests, and assessments conducted during unscheduled visits are performed with discretion.

If breakthrough hemolysis is suspected, LDH, PK, PD, and antidrug antibody (ADA) samples must be collected for analysis at the central laboratory. If the suspected event of breakthrough hemolysis occurs outside of a scheduled visit, patient is expected to return to the site for an Unscheduled Visit for evaluation and collection of the required LDH, PK, PD, and ADA samples. For the purposes of defining breakthrough hemolysis, assessment of LDH must be based on a central laboratory value.

TABLE 2

| | Ravulizumab Subcutaneous Treatment Group: Schedule of Study Visits and Activities—Screening Through End of Randomized Treatment Period | | | | | | | | | | |
|---|---|---|---|---|---|---|---|---|---|---|---|
| Study Day | Screening −30 to −1 | 1 | 15 | 22 | 29 | 36 | 43 | 50 | 57 | 64 | 71[a] |
| Study Week | | | 2 | 3 | 4 | 5 | 6 | 7 | 8 | 9 | 10 |
| Site visit (V) or at-home dosing of ravulizumab SC (H) | | V | V | H | V | H | V | H | V | V | V |
| Dose window (nominal time in hours from the start of the first dose on Day 1)[b] | | | ±1 | ±6 | ±6 | ±6 | ±6 | ±6 | ±1 | ±1 | ±1 |
| Informed consent | X | | | | | | | | | | |
| Inclusion/exclusion | X | X | | | | | | | | | |
| Medical history and demographics | X | | | | | | | | | | |
| Confirmation or administration of meningococcal vaccination[c] | X | X | | | | | | | | | |
| HIV testing | X | | | | | | | | | | |
| PNH clone size[d] | X | X | | | | | | | | | X |
| Height | X | | | | | | | | | | |

TABLE 2-continued

Ravulizumab Subcutaneous Treatment Group:
Schedule of Study Visits and Activities—Screening Through End of Randomized Treatment Period

| Study Day | Screening −30 to −1 | 1 | 15 | 22 | 29 | 36 | 43 | 50 | 57 | 64 | 71[a] |
|---|---|---|---|---|---|---|---|---|---|---|---|
| Weight | X | X | X | | X | | X | | X | X | X |
| Pregnancy test[e] | X | X | X | | | | | | | | X |
| Randomization | | X | | | | | | | | | |
| Ravulizumab IV loading dose administration[f] | | X | | | | | | | | | |
| Ravulizumab SC administration[g] | | | X[h] | X[i] | X[h] | X[i] | X[h] | X[i] | X[h] | X[h] | |
| Patient training on dose administration[j] | | | X | | | | | | | | |
| Scheduled telephone call[k] | | | | X | | X | | X | | | |
| Infusion site evaluation[l] | | X | X | | X | | X | | X | X | |
| PK/PD sampling (within 30 minutes predose)[m] | | X | X | | | | | | X | X | X |
| Postdose PK/PD sampling (within 30 minutes postdose) | | X | | | | | | | | | |
| Immunogenicity (ADA) (within 30 minutes predose)[m] | | X | | | | | | | | | X |
| PNH symptomatology | X | X | X | | | | X | | | | X |
| FACIT-Fatigue | X | X | | | | | X | | | | X |
| EORTC QLQ-C30 | X | X | | | | | X | | | | X |
| TASQ-IV[n] | X | X | X | | | | | | | | |
| TASQ-SC[o] | | | | | | | X | | | | X |
| Vital signs[p] | X | X | X | | X | | X | | X | X | X |
| Safety 12-lead ECG | X | | | | | | | | | | X |
| Chemistry, including LDH[q] | X | X | X | | X | | X | | X | | X |
| Hematology, including coagulation | X | X | X | | X | | X | | X | | X |
| Urinalysis and urine chemistry | X | X | X | | X | | X | | X | | X |
| Physical examination | X | | | | | | | | | | |
| Abbreviated physical examination[r] | | X | X | | X | | X | | X | | X |
| Review safety card | | X | X | | X | | X | | X | X | X |
| Breakthrough hemolysis[s] | | | | | ←Monitor continuously→ | | | | | | |
| Adverse events/adverse device effects | | | | | ←Monitor continuously→ | | | | | | |
| Concomitant medications | | | | | ←Monitor continuously→ | | | | | | |
| Record transfusions and transfusion parameters | | | | | ←Monitor continuously→ | | | | | | |

[a]Day 71 assessments for the Randomized Treatment Period must be performed predose on Day 71.

[b]Dosing must be administered on the visit day indicated during the Randomized Treatment Period. Doses after Day 1 are expected to be administered at the same nominal time as the dose on Day 1.

[c]All patients must be vaccinated against meningococcal infections within 3 years prior to, or at the time of, initiating study drug.

[d]White blood cell (granulocyte and monocyte) and red blood cell clone size measured by high-sensitivity flow cytometry at Screening and Day 1; red blood cell clone size only on Day 71.

[e]Female patients of childbearing potential only: serum pregnancy test at Screening and Day 71; urine pregnancy test at all other required time points. A negative urine test result is required prior to administering ravulizumab to female patients of childbearing potential at the indicated visits.

[f]Ravulizumab IV weight-based dosing on Day 1 (2400 mg for patients ≥40 to <60 kg and 2700 mg for patients ≥60 to <100 kg) is administered after Day 1 assessments are performed.

[g]Ravulizumab SC 490 mg qw maintenance dose on Day 15 and thereafter.

[h]Ravulizumab SC self-administered in the clinic.

[i]Ravulizumab SC self-administered at home. With approval, the patient can self-administer ravulizumab SC at the clinic on these days (with oversight by trained study site personnel).

[j]A qualified member of the site study team provides initial (and ongoing as appropriate) training on how to properly self-administer ravulizumab SC using the 2 required OBDS kits.

[k]Site will contact patient via telephone at scheduled dosing times to ensure patient is queried about study drug dose administration and device condition.

[l]New or worsening abnormalities should be reported as adverse events (AEs).

[m]The timing for PK sample collection is critical to the primary endpoint for this study. Serum samples for PK/PD/ADA analyses are collected as close as possible, but no more than 30 minutes prior to dosing. Day 71 dosing is included in the Extension Period. Samples are collected from the contralateral arm used for IV dosing. Samples are not collected from a heparinized line.

[n]At screening, patients complete TASQ-IV within 24 hours of receiving their eculizumab dose.

[o]Patients randomized to ravulizumab SC group complete TASQ-IV at Screening, Day 1 and Day 15 and then complete TASQ-SC at Day 43 and Day 71.

[p]On dosing days, vital signs are obtained before study drug administration.

[q]Follicle stimulating hormone levels are measured during Screening only in order to confirm postmenopausal status.

[r]Abbreviated physical examination consists of a body system relevant examination based upon Investigator (or designee) judgment and patient symptoms. At least 1 body system must be checked for an abbreviated physical examination.

[s]If a suspected event of breakthrough hemolysis occurs, blood samples for LDH, PK, PD, and ADA parameters are collected and sent to the central laboratory for analysis. If the suspected event of breakthrough does not occur at a scheduled visit, an unscheduled visit occurs for evaluation of the patient and collection of the required blood samples.

47 48

TABLE 3

Ravulizumab Intravenous Treatment Group: Schedule of Study
Visits and Activities—Screening Through End of Randomized Treatment Period

| Study Day | Screening −30 to −1 | 1 | 15 | 29 | 43 | 57 | 71[a] |
|---|---|---|---|---|---|---|---|
| Study Week | | | 2 | 4 | 6 | 8 | 10 |
| Site visit (V) | | V | V | V | V | V | V |
| Dose window (nominal time in hours from the start of first dose on Day 1)[b] | | | ±1 | | | | ±1 |
| Informed consent | X | | | | | | |
| Inclusion/Exclusion | X | X | | | | | |
| Medical history and demographics | X | | | | | | |
| Confirmation or administration of meningococcal vaccination[c] | X | X | | | | | |
| HIV testing | X | | | | | | |
| PNH clone size[d] | X | X | | | | | X |
| Height | X | | | | | | |
| Weight | X | X | X | | | | X |
| Pregnancy test[e] | X | X | X | | | | X |
| Randomization | | X | | | | | |
| Ravulizumab IV loading dose administration[f] | | X | | | | | |
| Ravulizumab IV administration[g] | | | X | | | | |
| Infusion site evaluation[h] | | X | X | | | | |
| PK/PD sampling (within 30 minutes predose)[i] | | X | X | | | | X |
| Postdose PK/PD sampling (within 30 minutes postdose) | | X | X | | | X[j] | |
| Immunogenicity (ADA) (within 30 minutes predose)[i] | | X | | | | | X |
| PNH symptomatology | X | X | X | | X | | X |
| FACIT-Fatigue | X | X | | | X | | X |
| EORTC QLQ-C30 | X | X | | | X | | X |
| TASQ-IV | X[k] | X | | | X | | X |
| Vital signs[l] | X | X | X | X | X | X | X |
| Safety 12-Lead ECG | X | | | | | | X |
| Chemistry, including LDH[m] | X | X | X | X | X | X | X |
| Hematology, including coagulation | X | X | X | X | X | X | X |
| Urinalysis and urine chemistry | X | X | X | X | X | X | X |
| Physical examination | X | | | | | | |
| Abbreviated physical examination[n] | | X | X | X | X | X | X |
| Review safety card | | X | X | X | X | X | X |
| Breakthrough hemolysis[o] | | ←Monitor continuously→ | | | | | |
| Adverse events | | ←Monitor continuously→ | | | | | |
| Concomitant medications | | ←Monitor continuously→ | | | | | |
| Record transfusions and transfusion parameters | | ←Monitor continuously→ | | | | | |

[a]Day 71 assessments for the Randomized Treatment Period must be performed predose on Day 71.

[b]Dosing must be administered on the visit day indicated during the Randomized Treatment Period. Doses after Day 1 are expected to be administered at the same nominal time as the dose on Day 1.

[c]All patients must be vaccinated against meningococcal infections within 3 years prior to, or at the time of, initiating study drug.

[d]White blood cell (granulocyte and monocyte) and red blood cell clone size measured by high-sensitivity flow cytometry at Screening and Day 1; red blood cell clone size only on Day 71.

[e]Female patients of childbearing potential only. Serum pregnancy test at Screening and Day 71; urine pregnancy test at all other required time points. A negative urine test result is required prior to administering ravulizumab to female patients of childbearing potential at the indicated visits.

[f]Ravulizumab IV weight-based loading dose on Day 1 (2400 mg for patients weighing ≥40 to <60 kg and 2700 mg for patients weighing ≥60 to <100 kg) is to be administered after Day 1 assessments are performed.

[g]Ravulizumab weight-based maintenance dosing on Day 15 is: 3000 mg for patients weighing ≥40 to <60 kg and 3300 mg for patients weighing ≥60 to <100 kg.

[h]New or worsening abnormalities should be reported as adverse events.

[i]The timing for PK sample collection is critical to the primary endpoint for this study. Serum samples for PK/PD/ADA analyses are collected as close as possible but no more than 30 minutes prior to dosing. Day 71 dosing is included in the Extension Period. Samples are collected from the contralateral arm used for IV dosing. Samples are not collected from a heparinized line.

[j]There is no dose of ravulizumab administered on Day 57; sample collected anytime during the assessments on Day 57.

[k]During Screening, patients complete TASQ-IV within 24 hours of receiving a dose of eculizumab.

[l]On dosing days, vital signs are obtained before study drug administration.

[m]Follicle stimulating hormone levels are measured during Screening only in order to confirm postmenopausal status.

[n]Abbreviated physical examination consists of a body system relevant examination based upon Investigator (or designee) judgment and patient symptoms. At least 1 body system is checked for an abbreviated physical examination.

[o]If a suspected event of breakthrough hemolysis occurs, blood samples for LDH, PK, PD, and ADA parameters are collected and sent to the central laboratory. If the suspected event of breakthrough does not occur at a scheduled visit, an Unscheduled Visit occurs for evaluation of the patient and collection of the required blood samples.

TABLE 4

Schedule of Study Visits and Activities, Exten. Period Through Day 365 (1 Year)

| Study Day | 71 | 78 | 85 | 99 | 127 | 183 | 239 | 295 | 365 |
|---|---|---|---|---|---|---|---|---|---|
| Study Week | 10 | | 12 | 14 | 18 | 26 | 34 | 42 | 52 |
| Site visit (V) or at-home dosing of ravulizumab SC (H) | V | H | V | V | V | V | V | V | V |
| Visit Window (±Day) | NA | | 1 | 1 | 1 | 1 | 1 | 1 | 1 |
| Dose window (nominal time in hours from the start of first dose on Day 1)[a] | ±1 | | | | | | | | |
| Patient training on dose administration[b] | X | | | | | | | | |
| Ravulizumab SC administration | X | X | X | X | X | X | X | X | X |
| Telephone call check | | X[c] | | | | | | | |
| Infusion site evaluation[d] | X | | X | X | X | X | X | X | X |
| PK/PD sampling[e] | X | | X | X | X | X | X | X | X |
| Immunogenicity (ADA)[e] | | | X | X | X | X | X | X | X |
| PNH symptomatology | | | | X | X | X | | X | X |
| FACIT-Fatigue | | X | | X | | X | | X | X |
| EORTC QLQ-C30 | | X | | X | | X | | X | X |
| TASQ-SC | | | X | | | | | | X |
| Vital signs[f] | | | X | X | X | X | X | X | X |
| Chemistry, including LDH | | | X | X | X | X | X | X | X |
| Hematology, including coagulation | | | X | X | X | X | X | X | X |
| Urinalysis and urine chemistry | | | X | X | X | X | X | X | X |
| Pregnancy test[g] | | | X | X | X | X | X | X | X |
| Weight | | | X | X | X | X | X | X | X |
| Abbreviated physical examination[h] | | | X | X | X | X | X | X | X |
| Review safety card | | | X | X | X | X | X | X | X |
| Treatment adherence monitoring by e-diary | | | ←At every weekly dose→ | | | | | | |
| Breakthrough hemolysis[i] | | | ←Monitor continuously→ | | | | | | |
| Record transfusions and transfusion parameters | | | ←Monitor continuously→ | | | | | | |
| Concomitant medications | | | ←Monitor continuously→ | | | | | | |
| Adverse events | | | ←Monitor continuously→ | | | | | | |

[a]Day 71 dosing is the beginning of the Extension Period. The Day 71 dose is to be administered at the same nominal time as the dose on Day 1. The ravulizumab SC 490 mg dose on Day 71 is self-administered in the clinic. For patients who had been randomized to the ravulizumab IV group, this is part of the required training program.
[b]For patients who had been randomized to the ravulizumab IV group, a qualified member of the site study team provides initial (and ongoing as appropriate) training on how to properly self-administer ravulizumab SC using the 2 required OBDS kits. For all patients, doses that coincide with study visit days are self-administered in the clinic with oversight by trained study site personnel. All other doses can be self-administered at home. With approval, the patient can self-administer ravulizumab SC at the clinic on dosing days that are not scheduled in-clinic visits (with oversight by trained study site personnel).
[c]Site contacts patients by telephone to query the patient on ravulizumab SC administration and completion of the patient e-diary.
[d]New or worsening abnormalities should be reported as adverse events.
[e]Serum samples for PK/PD/ADA analyses are collected predose (Day 71 included). Samples are not collected from a heparinized line.
[f]Vital signs are obtained before study drug administration.
[g]For female patients of childbearing potential only. A negative urine test result is required prior to administering ravulizumab to female patients of childbearing potential at the indicated visits.
[h]Abbreviated physical examination consists of a body system relevant examination based upon Investigator (or designee) judgment and patient symptoms. At least 1 body system is checked for an abbreviated physical examination.
[i]If a suspected event of breakthrough hemolysis occurs, blood samples for LDH, PK, PD, and ADA parameters are collected and sent to the central laboratory for analysis. If the suspected event of breakthrough does not occur at a scheduled visit, an unscheduled visit occurs for evaluation of the patient and collection of the required blood samples.

TABLE 5

Schedule of Study Visits and Activities—Extension Period, Day 421 Through Day 1275 (3.5 Years)

| Study Day | 421 | 477 | 533 | 589 | 645 | 701 | 757 | 813 | 869 | 925 | 981 | 1037 | 1093 | 1149 | 1205 | 1275/ ET | Safety Follow-up |
|---|---|---|---|---|---|---|---|---|---|---|---|---|---|---|---|---|---|
| Study Week | 60 | 68 | 76 | 84 | 92 | 100 | 108 | 116 | 124 | 132 | 140 | 148 | 156 | 164 | 172 | 182 | |
| Site Visit Window (±Day) | 3 | 3 | 3 | 3 | 3 | 3 | 3 | 3 | 3 | 3 | 3 | 3 | 3 | 3 | 3 | 3 | |
| Ravulizumab SC administration[a] | X | X | X | X | X | X | X | X | X | X | X | X | X | X | X | X | |
| Telephone call check | | | | | | | | | | | | | | | | | X[b] |
| PK/PD sampling[c] | X | X | X | X | X | X | X | X | X | X | X | X | X | X | X | X | |
| Immunogenicity (ADA)[c] | | X | | X | | X | | X | | X | | X | | X | | X | |
| FACIT-Fatigue | | | | | | | X | | | | | | X | | | X | |
| EORTC QLQ-C30 | | | | | | | X | | | | | | X | | | X | |

TABLE 5-continued

Schedule of Study Visits and Activities—Extension Period, Day 421 Through Day 1275 (3.5 Years)

| Study Day | 421 | 477 | 533 | 589 | 645 | 701 | 757 | 813 | 869 | 925 | 981 | 1037 | 1093 | 1149 | 1205 | 1275/ ET | Safety Follow- up |
|---|---|---|---|---|---|---|---|---|---|---|---|---|---|---|---|---|---|
| TASQ-SC | | | | | | | X | | | | | | X | | | X | |
| Vital signs[d] | X | X | X | X | X | X | X | X | X | X | X | X | X | X | X | X | |
| Safety 12-Lead ECG | | | | | | | | | | | | | | | | X | |
| Chemistry, including LDH | X | X | X | X | X | X | X | X | X | X | X | X | X | X | X | X | |
| Hematology, including coagulation | X | X | X | X | X | X | X | X | X | X | X | X | X | X | X | X | |
| Urinalysis and urine chemistry | X | X | X | X | X | X | X | X | X | X | X | X | X | X | X | X | |
| Pregnancy test[e] | X | X | X | X | X | X | X | X | X | X | X | X | X | X | X | X | |
| Weight | X | X | X | X | X | X | X | X | X | X | X | X | X | X | X | X | |
| Abbreviated physical examination[f] | X | X | X | X | X | X | X | X | X | X | X | X | X | X | X | | |
| Physical examination | | | | | | | | | | | | | | | | X | |
| Review safety card | X | X | X | X | X | X | X | X | X | X | X | X | X | X | X | X | |
| Treatment adherence monitoring by e-diary | | | | | | | ←At every weekly dose→ | | | | | | | | | | |
| Breakthrough hemolysis[g] | | | | | | | ←Monitor continuously→ | | | | | | | | | | |
| Record transfusions and transfusion parameters | | | | | | | ←Monitor continuously→ | | | | | | | | | | |
| Concomitant medications | | | | | | | ←Monitor continuously→ | | | | | | | | | | |
| Adverse events | | | | | | | ←Monitor continuously→ | | | | | | | | | | |

[a]For all patients, doses that coincide with study visit days can be self-administered in the clinic with oversight by trained study site personnel. All other doses can be self-administered at home.
[b]A follow-up phone call is to be conducted 30 days after the last dose of study drug and is limited to adverse event and concomitant medication monitoring.
[c]Serum samples for PK/PD/ADA analyses are collected predose. Samples are not collected from a heparinized line.
[d]Vital signs are obtained before study drug administration.
[e]For female patients of childbearing potential only. Serum pregnancy test at ET only; urine pregnancy test at all other time points. A negative urine test result is required prior to administering ravulizumab to female patients of childbearing potential at the indicated visits.
[f]Abbreviated physical examination consists of a body system relevant examination based upon Investigator (or designee) judgment and patient symptoms. At least 1 body system is checked for an abbreviated physical examination.
[g]If a suspected event of breakthrough hemolysis occurs, blood samples for LDH, PK, PD, and ADA parameters are collected and sent to the central laboratory for analysis. If the suspected event of breakthrough does not occur at a scheduled visit, an unscheduled visit occurs for evaluation of the patient and collection of the required blood samples.

5. Ravulizumab

The study drug formulations are set forth in Table 6.

TABLE 6

Study Drug Formulations

| Treatment | Formulation | Delivery Mechanism |
|---|---|---|
| Ravulizumab IV | 10 mg/mL ravulizumab in 10 mM sodium phosphate containing 150 mM sodium chloride, 0.02% polysorbate 80, and water for injection, pH 7.0 | Intravenous infusion |
| Ravulizumab SC | 70 mg/mL ravulizumab in 50 mM sodium phosphate containing 25 mM arginine, 5% sucrose, 0.05% polysorbate 80, and water for infusion, pH 7.4 | Subcutaneous infusion via on-body delivery system (OBDS) |

Ravulizumab SC is formulated at pH 7.4 and is supplied in 3.5-mL single-use cartridges. Each cartridge of ravulizumab SC contains 245 mg of ravulizumab (70 mg/mL) in 50 mM sodium phosphate, 25 mM arginine, 5% sucrose, 0.05% polysorbate 80, and water for injection.

Ravulizumab IV is formulated at pH 7.0 and is supplied in 30-mL single-use vials. Each vial of ravulizumab IV contains 300 mg of ravulizumab (10 mg/mL) in 10 mM sodium phosphate, 150 mM sodium chloride, 0.02% polysorbate 80, and water for injection.

Both ravulizumab SC and ravulizumab IV formulations are suitable for human use and manufactured under current Good Manufacturing Practices.

Details regarding ravulizumab SC and ravulizumab IV formulations are presented in Table 7. The dosing reference charts for ravulizumab SC and ravulizumab IV groups are presented in Table 8 and Table 9, respectively.

TABLE 7

| | Study Drug Administered | |
|---|---|---|
| | Ravulizumab SC (Test Therapy) | Ravulizumab IV (Reference Therapy) |
| Dosage Form | Concentrated, sterile, preservative-free aqueous solution (70 mg/mL) in single-use, 3.5-mL prefilled cartridge designed for use in a single-use on-body delivery system | Concentrated sterile, preservative-free aqueous solution (10 mg/mL) in single-use 30-mL vials |
| Route of Administration | SC infusion via the ravulizumab OBDS [a] | IV infusion by diluting into commercially available saline (0.9% sodium chloride injection; country-specific pharmacopeia) |
| Packaging and Supply | Ravulizumab primary container closure is cyclic olefinic polymer crystal zenith cartridge stoppered with butyl rubber stopper and a telescopic screw assembly. The ravulizumab OBDS is supplied in kits copackaged with the prefilled cartridge and device. | The US Pharmacopeia/European Pharmacopeia Type 1 borosilicate glass vials and stoppered with a butyl rubber stopper with an aluminum overseal and a flip-off cap. Study drug is supplied in kits. |
| Physical Description of Study Drug | Clear to translucent, slight yellowish in color, practically free from particles | Clear to translucent, slight whitish color, practically free from particles |
| Manufacturer | Alexion or contracted manufacturing organization | Alexion or contracted manufacturing organization |

[a] The ravulizumab on-body delivery system (OBDS) is a drug-device combination product of a prefilled cartridge containing ravulizumab and the West SmartDose device that is copackaged for SC administration.

TABLE 8

| | Dosing Reference Chart for Ravulizumab Subcutaneous Group | | | | | | |
|---|---|---|---|---|---|---|---|
| Dose Type | Body Weight (kg)[a] | Dose (mg) | Ravulizumab Volume (mL) | Saline Volume (mL) | Total Volume (mL) | Minimum Infusion Duration minutes (hours) | Maximum Infusion Rate (mL/hour) |
| Loading (IV) | ≥40 to <60 | 2400[a] | 240 | 240 | 480 | 114 (1.9) | 253 |
| | ≥60 to <100 | 2700[a] | 270 | 270 | 540 | 102 (1.7) | 318 |
| Maintenance (SC) | ≥40 to <100 | 490 | 3.5 mL × 2 | NA | 7.0 mL | 9 minutes (0.15)[b] | 23.3 |

Note:
Additional dose preparation instructions are provided in the pharmacy manual.
[a] Ravulizumab IV dose is based on the body weight at the last recorded study visit.
[b] The rate of the SC infusion is preprogrammed into the device. Nine minutes is an approximate based on the instructions for use.

TABLE 9

| | Dosing Reference Chart for Ravulizumab Intravenous Group | | | | | | |
|---|---|---|---|---|---|---|---|
| Dose Type | Body Weight (kg)[a] | Dose (mg) | Ravulizumab Volume (mL) | Saline Volume (mL) | Total Volume (mL) | Minimum Infusion Duration minutes (hours) | Maximum Infusion Rate (mL/hour) |
| Loading (IV) | ≥40 to <60 | 2400 | 240 | 240 | 480 | 114 (1.9) | 253 |
| | ≥60 to <100 | 2700 | 270 | 270 | 540 | 102 (1.7) | 318 |
| Maintenance (IV) | ≥40 to <60 | 3000 | 300 | 300 | 600 | 140 (2.4) | 250 |
| | ≥60 to <100 | 3300 | 330 | 330 | 660 | 120 (2.0) | 330 |
| Extension (SC) | ≥40 to <100 | 490 | 3.5 mL × 2 | NA | 7.0 mL | 9 minutes (0.15)[b] | 23.3 |

Note:
Additional dose preparation instructions are provided in the pharmacy manual.
[a] Ravulizumab IV dose is based on the body weight at the last recorded study visit.
[b] The rate of the SC infusion is preprogrammed into the device. Nine minutes is an approximate based on the instructions for use.
Abbreviations:
IV = intravenous;
NA = not applicable;
SC = subcutaneous.

Ravulizumab SC can be self-administered by patients who have completed the required training for self-administration of ravulizumab SC. Study drug is to be dispensed only to enrolled patients who are confirmed eligible for participation.

On Day 15 during the Randomized Treatment Period (for patients randomized to ravulizumab SC) and Day 71 during the Extension Period (for patients randomized to ravulizumab IV), a qualified member of the site study team provides initial (and ongoing as appropriate) training on how to properly self-administer ravulizumab SC using the 2 required OBDS kits. Following completion of required training, all patients self-administer their weekly SC infusions at home or in the clinic (with oversight by trained study site personnel), on days specified in the Schedule of Activities. With approval, the patient can self-administer ravulizumab SC at the clinic on dosing days that are not scheduled in-clinic visits.

The patient is required to follow the instructions for use (IFU) as written. Detailed instructions regarding self-administration of the study drug are provided in the IFU.

In the event of OBDS malfunction where no dose or a partial dose is delivered, the patient uses a new OBDS to ensure that the patient receives at least 490 mg of ravulizumab SC.

Ravulizumab IV is not administered as an IV push or bolus injection. Infusions of ravulizumab IV are prepared using aseptic technique. The patient's required dose of ravulizumab are further diluted as specified in Table 7 and Table 8. Once the dosing solution is prepared for a patient, it can only be administered to that patient. Drug is administered using an IV tubing set via an infusion pump. Use of a 0.2-micron filter is required during infusion of ravulizumab IV. Vials of study drug are for one time use only and any drug product remaining in the vial is not used for another patient.

The in-use shelf life of the dosing solution is 6 hours at ambient temperature. The expiration date and time of the dosing solution is calculated from breach of the first vial. The dose is administered within the expiration date and time.

The primary packaging of ravulizumab IV consists of a 30-mL vial (Type I borosilicate glass) with a stopper and a seal. The secondary packaging consists of a single vial carton. Both primary (vial) and secondary (carton) packaging include a booklet label with relevant information.

6. On-Body Delivery System

Ravulizumab SC is intended to be self-administered via SC infusion for maintenance dosing using the ravulizumab OBDS in the clinic or home setting. The drivers for the SC device selection were dose volume capability, demonstrated reliability, and patient-centered usability requirements including ease of use with minimal steps, minimal discomfort, hidden needle, as well as the ability to move about and perform moderate physical activities during the infusion such as walking, reaching, and bending. The West Smart-Dose Gen 1 device platform meets these criteria.

The ravulizumab OBDS drug-device combination product consists of a prefilled cartridge containing ravulizumab SC and an on-body injector. The ravulizumab OBDS is a compact, sterile, single-use, electro-mechanical, wearable infusion device that administers a fixed dose of ravulizumab from a prefilled cartridge assembly into an SC tissue at a fixed rate via a stainless steel 29-gauge needle. The device is a sterile, single use, surgically invasive active medical device for transient use as per definitions from Medical Device Directive 93/42/EEC. The device contains non removable batteries and includes a biocompatible adhesive patch. The device with adhesive is removed from the skin following completion of the dose.

The primary container closure (cartridge) consists of a 5-mL CZ cartridge with a chlorobutyl elastomeric septum, a chlorobutyl elastomeric piston, and a TSA that is threaded into the piston. The prefilled CZ cartridge is copackaged with the on-body injector in a 2-compartment blister tray. The prefilled cartridge assembly is loaded into the device immediately prior to use by the patient. The device is designed for use only with the provided 3.5-mL prefilled cartridge.

After loading the cartridge into the device, adhering the device to the skin, and device activation the 3.5-mL dose is delivered in less than 10 minutes.

Following the completion of training on the use of the device by a qualified member of the site study team, all patients self-administer ravulizumab SC doses as specified in the SoA. Additional instructions are provided in the IFU. vAdditional details on the device are located in the Ravulizumab OBDS Investigator's Brochure.

The ravulizumab OBDS drug-device combination consists of 2 parts: a prefilled cartridge containing ravulizumab and the on-body injector. The prefilled cartridge and device constituent parts are copackaged in a thermoformed blister pack with a Tyvek lid over the compartment containing the device to provide a sterile barrier. The secondary packaging consists of a blank carton containing the blister pack and a booklet label with relevant instructions.

An identification trace label is attached to the Tyvek covered blister, a serial number label attached to the side of the device, and a single panel label is affixed to each cartridge.

7. Ravulizumab IV and Ravulizumab SC—In-Clinic Administration

Study drug kits are released to each site upon receipt of all required documentation based upon applicable regulations.

Upon arrival of the study drug kits at the study site, the pharmacist or designee promptly remove the study drug kits from the shipping cooler and store them in their original cartons under refrigerated conditions at 2° C. to 8° C. (35° F. to 47° F.) and protected from light. Ravulizumab IV admixed drug product and ravulizumab OBDS kits is at ambient temperature prior to administration. The material must not be heated (e.g., by using a microwave or other heat source).

Only authorized site staff may supply or administer study drug at times.

The patient undergoes training, by a qualified member of the site study team, to self-administer using the ravulizumab OBDS on Day 15 (patients randomized to ravulizumab SC) and on Day 71 during the Extension Period (patients who had been randomized to ravulizumab IV). After completion of training, ravulizumab SC can be self-administered by the patient at home or self-administered in the clinic with oversight by trained study site personnel at times noted. All study drugs must be stored in a secure, environmentally controlled, and monitored (manual or automated) area in accordance with the labeled storage conditions with access limited to the Investigator and authorized site staff.

The Investigator, institution, pharmacist, or the head of the medical institution (if applicable) is responsible for study drug accountability, reconciliation, and record maintenance (i.e., receipt, reconciliation, and final disposition records).

Unless institutional procedures require immediate destruction of used ravulizumab IV drug, accountability is performed on used and unused IV study drug vials.

The ravulizumab OBDS is a single-use device that is immediately disposed in a biological waste container after drug administration. Accountability is performed on used and unused cartridges and devices.

At study drug kits supplied, dispensed, and subsequently destroyed or returned to Alexion.

8. Ravulizumab SC—At-Home Administration

Ravulizumab OBDS kits for self-administration are provided to patients in accordance with regional and local requirements.

Upon receipt of the ravulizumab OBDS kits the patient is expected to promptly store them in accordance with the IFU.

Patients are expected to follow the training instructions and IFU on each dosing day to ensure appropriate administration of their ravulizumab dose. The study site personnel monitor self-administration of ravulizumab SC via telephone calls with the patient on scheduled at-home dosing days during the Randomized Treatment Period to ensure that the patient is queried about study drug dose administered and device condition. During the Extension Period, ravulizumab SC is self-administered by the patient at home or self-administered in the clinic with oversight by trained study site personnel on scheduled visit days. With approval, the patient can self-administer ravulizumab SC at the clinic on dosing days that are not scheduled in-clinic visits. On Day 71, patients who had been randomized to the ravulizumab IV group self-administer ravulizumab SC in the clinic with oversight by trained study site personnel as part of the required training program for at-home self-administration.

A biological waste container is supplied to each patient for at-home disposal of used ravulizumab OBDS.

9. Measures to Minimize Bias: Randomization and Blinding

This is an open-label study. Measures implemented to reduce potential bias include stratification and randomization. Following stratification by weight (≥40 to <60 kg or ≥60 to <100 kg) each patient is randomly assigned to a treatment group in a 2:1 ratio using a centralized interactive voice- or web response system.

10. Prior and Concomitant Therapy

Prior medications (including vitamins and herbal preparations), including those discussed in the exclusion criteria and procedures (any therapeutic intervention, such as surgery/biopsy or physical therapy) the patient takes or undergoes within 28 days prior to the start of Screening until the first dose of study drug, are recorded in the patient's electronic case report forms (eCRF). In addition, history of meningococcal vaccination is collected for the 3 years prior to first dose of study drug.

Transfusions of packed red blood cells received within 1 year prior to first study drug administration are recorded in the patient's eCRF.

All medication use and procedures undertaken during the study are recorded in the patient's source document/medical chart and eCRF. This record includes all prescription drugs, herbal products, vitamins, minerals, over-the-counter medications, and current medications for PNH. Concomitant medications are recorded from the first infusion of study drug through 30 days after the patient's last dose of study drug, unless the patient transitions to an alternate treatment for PNH. Any changes in concomitant medications also are recorded in the patient's source document/medical chart and eCRF. Any concomitant medication deemed necessary for the patient's standard of care during the study, or for the treatment of any AE, along with the allowed medications described below may be given with discretion.

Concomitant use of anticoagulants is prohibited if not on a stable dose regimen for at least 2 weeks prior to study entry. Use of complement inhibitors other than the patient's assigned study treatment is prohibited.

11. Dose or Treatment Group Modification

Patients who received ravulizumab IV during the Randomized Treatment Period switch to ravulizumab SC 490 mg once weekly w at the start of the Extension Period and continue with this treatment for the duration of the study.

During the Randomized Treatment Period, if any patient administered ravulizumab IV reaches a body weight ≥100 kg before Day 71, the patient's data is excluded from the primary endpoint analysis and the patient is discontinued from the study. If the patient's body weight is <100 kg on Day 71, the patient's data is included in the primary analysis. The patient is discontinued from the study following completion of Day 71 predose assessments.

During the Randomized Treatment Period, if any patient administered ravulizumab SC reaches a body weight ≥100 kg, the patient is discontinued from treatment. The patient's data is not included in the primary endpoint analysis, unless the first observation of such a weight for this patient was at the Day 71 assessment. The patient is discontinued from the study.

If any patient administered ravulizumab SC reaches a body weight ≥100 kg, the patient is discontinued from treatment.

No other dose or treatment group modification is permitted in the study.

12. Potential and Identified Risks

Increased susceptibility to infection with *Neisseria meningitidis* is a known risk associated with terminal complement inhibition. Similar to eculizumab, the main risk associated with ravulizumab is the risk of meningococcal infections.

Specific risk mitigation measures are in place to address this risk.

Administration of any therapeutic protein, including ravulizumab, may induce an immunogenic response potentially resulting in ADAs. The spectrum of potential clinical consequences may include severe hypersensitivity-type reactions and decrease in efficacy (PK and/or PD neutralization) due to development of neutralizing ADA.

Of the 261 patients with PNH who were treated with ravulizumab in the ravulizumab IV clinical studies, 1 patient developed a treatment-emergent ADA. Treatment-emergent ADAs have been observed in 3 healthy subjects treated with ravulizumab SC and 1 healthy subject treated with ravulizumab IV in Study ALXN1210-SC-101, and in 4 healthy Japanese subjects in Study ALXN1210-HV-104. All ADA positive titer values were low and negative for eculizumab cross-reactivity. There was no apparent impact of immunogenicity on the PK or PD of ravulizumab.

In studies of patients with atypical hemolytic uremic syndrome (aHUS), only 1 treatment-emergent ADA has been reported with ravulizumab.

Protein therapies administered either SC or IV have the potential risk of causing local (infusion-site reactions) and systemic reactions (infusion-associated reactions). Infusion-site reactions are those localized to the site of SC or IV drug administration and may include reactions such as erythema, pruritus, and bruising. Infusion-associated reactions are those systemic in nature which may be immune or non immune-mediated generally occurring within hours of drug administration. Immune-mediated reactions may include allergic reactions (eg, anaphylaxis), while non immune-mediated reactions are nonspecific (eg, headache, dizziness, nausea). Monitoring for these reactions is conducted as part of routine safety assessments for this study.

No studies of ravulizumab have been conducted in pregnant women.

Pregnant or nursing female patients are excluded from the clinical study. Patients enrolled in the study, and their spouses/partners, use a highly effective or acceptable method of contraception. In the event of a pregnancy, the patient is discontinued from study drug.

There is no clinical experience with the ravulizumab OBDS. It is considered an investigational medical device and as such bears some potential risks resulting from device deficiencies or user error. Risk management activities (risk control and mitigation measures) have been conducted. Reference may be made to the Ravulizumab OBDS Investigator's Brochure for a more complete description of the device and potential benefit/risk.

Data supporting the development of the ravulizumab OBDS include the data from the healthy volunteer study using the SmartDose device, that showed the device was well tolerated and safe to use. A risk management study was performed on the ravulizumab OBDS by Alexion and West Pharmaceutical Services, Inc. and risk analyses were performed in accordance with EN ISO 14971:2012. The results of these risk assessments show that all residual risks fall under the low/acceptable or medium/investigate risk category. Control strategies are in place to further mitigate the medium/investigate category risks. Therefore, it is considered that these potential risks are balanced by the opportunity to develop ravulizumab OBDS as an alternative and more convenient way of drug administration in patients requiring chronic treatment.

13. End of Study Definition

The end of the study for each patient occurs when the safety follow-up is completed. The safety follow-up consists of a telephone call 30 days after the last dose. Data collection during the safety follow-up is limited to reporting adverse events and concomitant medications. If a patient discontinues treatment, but does not discontinue from the study, the end of study for such a patient is their last visit as long as that visit is more than 30 days from their last dose. The end of the study is defined as the date of the last patient visit or safety follow up, whichever occurs later.

14. Efficacy Assessments

Blood and urine samples are collected at the time points indicated in the Schedule of Assessments. The following disease-related laboratory parameters are measured during the study: (1) lactate dehydrogenase, (2) reticulocyte count, (3) paroxysmal nocturnal hemoglobinuria RBC clone size evaluated by high-sensitivity flow cytometry, (4) estimated glomerular filtration rate (calculated using the Modification of Diet in Renal Disease formula).

Achievement of transfusion avoidance is defined as patients who remained transfusion free and did not require a transfusion after the first dose of study drug.

Breakthrough hemolysis is defined as at least 1 new or worsening symptom or sign of intravascular hemolysis (fatigue, hemoglobinuria, abdominal pain, shortness of breath [dyspnea], anemia [hemoglobin <10 g/dL], MAVE including thrombosis, dysphagia, or erectile dysfunction) in the presence of elevated LDH≥2×ULN as assessed by the central laboratory.

Stabilized hemoglobin is defined as the avoidance of a ≥2 g/dL decrease in hemoglobin level from Baseline in the absence of transfusion from Baseline to the end of the period of interest.

The Investigator or designee assesses each patient for signs and symptoms of PNH, which may include the following: fatigue, chest pain, abdominal pain, dyspnea, dysphagia, erectile Two validated HRQoL scales are administered to patients before study drug administration and at the time points specified in the Schedule of Assessments. The Functional Assessment of Chronic Illness Therapy (FACIT)-Fatigue scale, Version 4.0, is a collection of HRQoL questionnaires pertaining to the management of fatigue symptoms due to a chronic illness (see FIG. 1). The FACIT-Fatigue is a 13-item questionnaire that assesses self-reported fatigue and its impact upon daily activities and function over the preceding 7 days. Patients score each item on a 5-point scale: 0 (not at all) to 4 (very much). Total scores range from 0 to 52 with higher score indicating better HRQoL.

The European Organisation for Research and Treatment of Cancer (EORTC) Quality of Life Questionnaire-Core 30 Scale (QLQ-C30), Version 3.0, is a questionnaire developed to assess the HRQoL of cancer patients (See FIGS. 2A-2B). The questionnaire includes the following subscales: global health status, functional scales (physical functioning, role functioning, emotional functioning, cognitive functioning, and social activity), symptom scales (fatigue, nausea and vomiting, and pain), and single items (dyspnea, insomnia, appetite loss, constipation, diarrhea, and financial difficulties). Thirty questions are related to HRQoL, with the first 28 questions scored on a 4-point scale (1=not at all to 4=very much) and the final 2 questions that probe the patient's overall health and HRQoL scored on a scale of 1 (very poor) to 7 (excellent). Each subscale has a range of 0% to 100%, with a high score representing a higher response level. Thus, a high score for a functional scale represents a high level of functioning, but a high score for a symptom scale represents a high level of symptomatology/problem.

Treatment satisfaction will also be assessed at the time points specified in the Schedule of Assessments. The Treatment Administration Satisfaction Questionnaire (TASQ) is a validated questionnaire that will assess patients' perceptions and satisfaction with eculizumab IV, ravulizumab IV, or ravulizumab SC treatment (see FIG. 3, FIG. 4, and Theodore-Oklota et al., Patient Prefer Adherence. 2016; 10:1767-1776). The TASQ scores treatment satisfaction through 5 domains: physical impact, psychological impact, impact on ADL, convenience, and satisfaction. Each domain offers up to 5 response options with lower scores indicating a more positive response. Scoring is completed by summing each of the 5 domains.

The FACIT-Fatigue, EORTC QLQ-C30, and TASQ-IV/TASQ-SC are administered and recorded on paper.

15. Safety Assessments

The Investigator or designee meets with the patients to discuss the potential safety risks of ravulizumab SC, ravulizumab OBDS, and ravulizumab IV to give the Investigator the opportunity to address any of the patient's safety concerns regarding the study.

The time points for all safety assessments are provided in the Schedule of Assessments.

The description of the major adverse vascular events (MAVE), including the method of diagnosis (e.g., magnetic resonance imaging, ultrasound, angiogram), date of diagnosis, and date resolved (or ongoing) are collected on the eCRF as part of the patient's medical history (prior to Baseline) and throughout the study.

A MAVE is defined as follows: Thrombophlebitis/deep vein thrombosis, Pulmonary embolus, Myocardial infarction, Transient ischemic attack, Unstable angina, Renal vein thrombosis, Acute peripheral vascular occlusion, Mesenteric/visceral vein thrombosis or infarction, Mesenteric/visceral arterial thrombosis or infarction, Hepatic/portal vein thrombosis (Budd-Chiari syndrome), Cerebral arterial occlusion/cerebrovascular accident, Cerebral venous occlusion, Renal arterial thrombosis, gangrene (nontraumatic; nondiabetic), amputation (nontraumatic; nondiabetic), dermal thrombosis, or other (specify)

A physical examination includes the following assessments: general appearance; skin; head, ear, eye, nose, and throat; neck; lymph nodes; chest; heart; abdominal cavity; limb; central nervous system; and musculoskeletal system. An abbreviated physical examination consists of a body system relevant examination based upon Investigator judgment and patient symptoms.

Subcutaneous or IV infusion site evaluations are performed at the time points specified in the Schedule of Assessments.

Vital sign measurements are taken after the patient has been resting for at least 5 minutes, and include systolic and diastolic blood pressure (BP; mm Hg), heart rate (beats/minute), respiratory rate (breaths/minute), and temperature (° C. or ° F.).

Single 12-lead electrocardiogram (ECG) is obtained as outlined in the Schedule of Assessments using an ECG machine that automatically calculates the heart rate and measures PR, QRS, QT, and QTc intervals.

Patients must be supine for approximately 5 to 10 minutes before ECG collection and remain supine, but awake during ECG collection.

The Investigator or designee is responsible for reviewing the ECG to assess whether the ECG is within normal limits and determine the clinical significance of the results. These assessments are indicated on the eCRF.

Urine samples are analyzed for the parameters listed in Table 10. A microscopic examination of urine samples is performed if the results of the macroscopic analysis are abnormal. Urine samples are also analyzed to measure protein and creatinine to calculate the urine protein:creatinine ratio.

TABLE 10

Protocol-Required Safety Laboratory Assessments

| Laboratory Assessments | Parameters | | |
|---|---|---|---|
| Hematology | Platelet Count Red blood cell (RBC) Count Hemoglobin Hematocrit | RBC Indices: Distribution width Mean corpuscular volume Mean corpuscular hemoglobin % Reticulocytes | White blood cell (WBC) count with Differential: Neutrophils Lymphocytes Monocytes Eosinophils Basophils |
| Clinical Chemistry | Blood urea nitrogen (BUN) C-reactive protein Creatinine | Aspartate aminotransferase (AST)/serum glutamic oxaloacetic transaminase (SGOT) | Total and direct bilirubin |
| | Chloride Potassium Bicarbonate Sodium | Alanine aminotransferase (ALT)/serum glutamic pyruvic transaminase (SGPT) | Total protein |
| | Glucose (nonfasting) | Alkaline phosphatase, Gamma glutamyltransferase, Lactate dehydrogenase | Albumin Uric acid |
| Coagulation | D-dimer, international normalized ratio, partial thromboplastin time, prothrombin time | | |
| Routine urinalysis | Appearance, color, specific gravity, pH, glucose, protein, blood, ketones, bilirubin, urobilinogen, nitrite, creatinine and protein:creatinine ratio Microscopic examination (if blood or protein is abnormal) | | |
| Other Screening tests | Serum human chorionic gonadotropin (hCG) pregnancy test (as needed for women of childbearing potential) Follicle stimulating hormone testing Human immunodeficiency virus (HIV)-1 and HIV-2 antibodies The results of each test must be entered into the eCRF. | | |
| Complement activity | Free C5, PNH clone size | | |

Human immunodeficiency virus testing for HIV-1 and HIV-2 is required of all patients prior to enrollment. Patients who are HIV positive are not enrolled.

Blood samples are collected to test for presence of ADAs to ravulizumab in serum prior to study drug administration. Further characterization of antibody responses may be conducted as appropriate, including binding and neutralizing antibodies, PK/PD, safety, and activity of ravulizumab. Antibodies to ravulizumab are evaluated in serum samples collected from all patients according to the Schedule of Assessments. Serum samples are screened for antibodies binding to ravulizumab and the titer of confirmed positive samples is reported. The detection and characterization of antibodies to ravulizumab is performed using a validated assay.

Adverse events and serious adverse events are reported. An adverse event (AE) is any untoward medical occurrence in a patient administered a pharmaceutical product and which does not necessarily have a causal relationship with this treatment. An adverse event can therefore be any unfavorable or unintended sign (e.g., an abnormal laboratory finding), symptom, or disease temporally associated with the use of a medicinal product, whether or not considered related to the medicinal product.

Events that meet the adverse event definition include: (1) any abnormal laboratory test results (hematology, clinical chemistry, or urinalysis) or other safety assessments (e.g., ECG, radiological scans, vital signs measurements), including those that worsen from baseline, considered clinically significant in the medical and scientific judgment of the Investigator (i.e., not related to progression of underlying disease), (2) exacerbation of a chronic or intermittent pre-existing condition including either an increase in frequency and/or intensity of the condition, (3) new conditions detected or diagnosed after study drug administration even though it may have been present before the start of the study, (4) signs, symptoms, or the clinical sequelae of a suspected drug-drug interaction, (5) "Lack of efficacy" or "failure of expected pharmacological action" per se are be reported as an AE or SAE. Such instances are captured in the efficacy assessments. However, the signs, symptoms, and/or clinical sequelae resulting from lack of efficacy are reported as AE or SAE if they fulfil the definition of an AE or SAE, and (6) the signs, symptoms, and/or clinical sequelae resulting from lack of efficacy are reported as AE or SAE if they fulfil the definition of an AE or SAE.

Events that do not meet the adverse event definition include: (1) medical or surgical procedure (e.g., endoscopy, appendectomy): the condition that leads to the procedure is the AE. Situations in which an untoward medical occurrence did not occur (e.g., hospitalization for elective surgery if planned before the signing the ICF, admissions for social reasons or for convenience), (2) anticipated day-to-day fluctuations of pre-existing disease(s) or condition(s) present or detected at the start of the study that do not worsen, (3) lack of drug effect is not an AE in clinical studies, because the purpose of the clinical study is to establish drug effect, (4) medication error (including intentional misuse, abuse, and overdose of the product) or use other than what is defined in the protocol is not considered an AE unless there is an untoward medical occurrence as a result of a medication error, and (5) cases of pregnancy that occur during maternal or paternal exposure to investigational product are reported within 24 hours of Investigator/site awareness. Data on fetal outcome and breastfeeding is collected for regulatory reporting and safety evaluation.

If an event is not an adverse event per definition above, then it cannot be an serious adverse event (SAE) even if serious conditions are met (e.g., hospitalization for signs/symptoms of the disease under study, death due to progression of disease). Transfusions administered in the inpatient or outpatient setting are not captured as adverse events or serious adverse events unless identified as such by the Investigator. The definition of a serious adverse event is set forth in Table 11.

TABLE 11

| Serious Adverse Event |
|---|
| A serious adverse event is defined as any untoward medical occurrence that, at any dose: |

1. Results in death
2. Is life-threatening
The term 'life-threatening' in the definition of 'serious' refers to an event in which the patient was at risk of death at the time of the event. It does not refer to an event, which hypothetically might have caused death, if it were more severe.
3. Requires inpatient hospitalization or prolongation of existing hospitalization
In general, hospitalization signifies that the patient has been detained (usually involving at least an overnight stay) at the hospital or emergency ward for observation and/or treatment that would not have been appropriate in the physician's office or outpatient setting. Complications that occur during hospitalization are AEs. If a complication prolongs hospitalization or fulfills any other serious criteria, the event is serious. When in doubt as to whether "hospitalization" occurred or was necessary, the AE should be considered serious.
Hospitalization for elective treatment of a pre-existing condition that did not worsen from baseline is not considered an AE.
4. Results in persistent disability/incapacity
The term disability means a substantial disruption of a person's ability to conduct normal life functions.
This definition is not intended to include experiences of relatively minor medical significance such as uncomplicated headache, nausea, vomiting, diarrhea, influenza, and accidental trauma (e.g., sprained ankle) which may interfere with or prevent everyday life functions but do not constitute a substantial disruption.
5. Is a congenital anomaly/birth defect
6. Other situations:
Medical or scientific judgment should be exercised in deciding whether SAE reporting is appropriate in other situations such as important medical events that may not be immediately life-threatening or result in death or hospitalization but based upon appropriate medical judgment may jeopardize the patient or may require medical or surgical intervention to prevent one of the other outcomes listed in the above definition. These events should usually be considered serious.

A suspected unexpected serious adverse reaction (SUSARs) is a serious event that is not listed in the IB and that the Investigator identifies as related to investigational product or procedure.

An adverse device effect (ADE) is an adverse event deemed related to the use of an investigational medical device. This includes any adverse event resulting from insufficiencies or inadequacies in the instructions for use, the deployment, the installation, the operation, or any malfunction of the investigational medical device. An ADE includes any event that is a result of use error or intentional misuse. Use error refers to an act or omission of an act which results in a different device response than intended by the manufacturer or the user. An unexpected physiological response of the subject does not in itself constitute a use error. Missing dose (no dose) and partial dose (under dose) medication errors occurring with the use of the device are considered ADEs. Each ADE must be associated with 1 study device (i.e., 1 OBDS kit in the current study). Ravulizumab SC overdose involving multiple OBDS kits is a medication error pertaining to the SC drug administration route therefore is not considered an ADE.

ADEs can arise from the following occasions: (1) normal use example: injection site reactions not associated with any apparent device deficiency, use error or abnormal use of the device (2) device deficiency example: A bent needle leading to injection site laceration, (3) use error example: With all the intentions to follow the IFU to complete the required dosing, a subject forgot to properly prepare the device application site skin by trimming the hairs leading to the device falling off in the middle of the dosing that led to a partial dosing, (4) misuse (abnormal use) example: A subject, against the device indications specified in the ravulizumab OBDS IB, used the device to administer a substance other than the investigational drug, resulting in toxicity stemming from the substance.

Two OBDS kits are used to deliver the full 490 mg dose of ravulizumab SC. Missed dose (no dose) and partial dose (under dose) medication errors associated with study devices or the use of study devices are considered ADEs. Any missing dose or no dose delivered associated with ravulizumab SC administration using OBDS is considered an ADE. The kit number associated with the no dose ADE should be recorded together with the ADE. Following a partial dose there may be an ADE associated with one device. Therefore, one partial dose ADE is associated with one OBDS unit and one kit number is required in the recording of the partial dose ADE.

A serious adverse device effect (SADE) is an ADE that has resulted in any of the consequences characteristic of an SAE.

An unanticipated serious adverse device effect (USADE) is an SADE which by its nature, incidence, severity or outcome has not been identified in the current version of the ravulizumab OBDS IB as an expected event.

A device deficiency is an inadequacy of an investigational medical device related to its identity, quality, durability, reliability, safety or performance. This may be due to malfunction, misuse, user error, inadequate labeling or insufficient information provided by the manufacturer. If a medication error is associated with a device deficiency/malfunction, it is considered an ADE.

The Investigator makes an assessment of severity for each AE and SAE reported during the study and assign it to 1 of the following categories from National Cancer Institute Common Terminology Criteria for Adverse Events (CTCAE) v4.03, published 14 Jun. 2010. Each CTCAE term is a Lowest Level Term (LLT) per the MedDRA. Each LLT will be coded to a MedDRA Preferred Term: (1) Grade 1: Mild (asymptomatic or mild symptoms; clinical or diagnostic observations only; intervention not indicated), (2) Grade 2: Moderate (minimal, local or noninvasive intervention indicated; limiting age-appropriate instrumental ADL), (3) Grade 3: Severe (severe or medically significant, but not immediately life-threatening; hospitalization or prolongation of hospitalization indicated; disabling; limiting self-care ADL), (4) Grade 4: Life-threatening (urgent intervention indicated), and (5) Grade 5: Fatal (death related to AE). Any change in the severity of an AE should be documented based on specific guidelines in the eCRF Completion Guidelines. Severity and seriousness must be differentiated: severity describes the intensity of an AE, while the term seriousness refers to an AE that has met specific criteria for an SAE as described above.

The Investigator is obligated to assess the relationship between study drug and occurrence of each AE/SAE and between study device and occurrence of each ADE/SADE. An Investigator causality assessment must be provided for all AEs and ADEs (both nonserious and serious). This assessment must be recorded in the eCRF and on any additional forms, as appropriate. The definitions for the causality assessments are as follows: (1) not related (unrelated): There is no evidence to suggest that there was a reasonable possibility that the drug caused the adverse event and (2) related: There is evidence to suggest that there was a reasonable possibility that the drug caused the adverse event. The Investigator will use clinical judgment to determine the relationship to the study drug or the investigational medical device. Alternative causes, such as underlying disease(s), concomitant therapy, and other risk factors, as well as the temporal relationship of the event to study drug administration are considered and investigated. This protocol uses the current IB as the Reference Safety Document. The expectedness and reporting criteria of an SAE are determined by the Sponsor, based on the Reference Safety Document. There may be situations in which an SAE has occurred and the Investigator has minimal information to include in the initial report. However, it is very important that the Investigator always make an assessment of causality for every event before the initial transmission of the SAE data.

All events are collected from the signing of the ICF until the follow-up contact specified in the Schedule of Assessments.

As with any terminal complement antagonist, the use of ravulizumab increases the patient's susceptibility to meningococcal infection (*N meningitidis*). To reduce the risk of meningococcal infection, all patients must have been vaccinated against meningococcal infections within 3 years prior to, or at the time of, initiating study drug. Patients who initiate study drug treatment less than 2 weeks after receiving a meningococcal vaccine must receive treatment with appropriate prophylactic antibiotics until 2 weeks after vaccination.

Vaccines against serotypes A, C, Y, W135, and B, where available, are recommended to prevent common pathogenic meningococcal serotypes. Patients must be vaccinated or revaccinated according to current national vaccination guidelines or local practice for vaccination use with complement inhibitors (e.g., eculizumab).

Vaccination may not be sufficient to prevent meningococcal infection. Consideration should be given per official guidance and local practice on the appropriate use of antibacterial agents. All patients are monitored for early signs of meningococcal infection, evaluated immediately if infection is suspected, and treated with appropriate antibiotics, if necessary.

To increase risk awareness and promote quick disclosure of any potential signs or symptoms of infection experienced by the patients during the course of the study patients are provided a safety card to carry with them at all times. Additional discussion and explanation of the potential risks, signs, and symptoms occur at each visit as part of the review of the patient safety card as described in the Schedule of Assessments. Vaccination(s) for *N meningitidis* is recorded in the patient's eCRF.

Infusion-site reactions are those localized to the site of SC or IV drug administration and may include those such as erythema, pruritus, and bruising. Infusion-associated reactions are those systemic in nature which may be immune or nonimmune-mediated generally occurring within hours of drug administration. Immune-mediated reactions may include allergic reactions (e.g., anaphylaxis), while non immune-mediated reactions are nonspecific (e.g., headache, dizziness, nausea). Monitoring for these reactions is conducted as part of routine safety assessments for this study.

Infusion-associated reactions are defined as systemic adverse events (e.g., fever, chills, flushing, alterations in heart rate and BP, dyspnea, nausea, vomiting, diarrhea, and generalized skin rashes) occurring during or within 24 hours of the start of IV or SC infusion that are assessed by the Investigator to be related to the study drug.

Device performance is assessed using the reported outcome of attempted full dose administration (including device failure/malfunction) per the requirements in the IFU.

In the event of a device deficiency, whether or not associated with a missed dose, the ravulizumab OBDS may be sent to a core laboratory for analysis.

For this study, any IV or SC dose of ravulizumab greater than that specified/required in the protocol is considered an overdose medication error. Overdoses are medication errors which are not considered AEs or ADEs unless there is an untoward medical occurrence resulting from them.

Overdose associated with SC administration of ravulizumab via OBDS is defined as administration of ravulizumab SC greater than the dose contained in 2 full OBDS cartridges. The definition is developed for the practical considerations that a full dose ravulizumab SC administration entails the use of multiple OBDS units, each with a cartridge containing a fixed dose/volume of ravulizumab. The definition is based on the overdose definition for a study drug and the wide dose range of safety tolerance for ravulizumab previously clinically investigated (up to 5400 mg IV, equivalent to <ravulizumab in ten full OBDS cartridges).

16. Pharmacokinetic Assessments

The timing for collection of samples for PK is critical to the primary endpoint for this study. The time of the start of the dose administered on Day 1 is the nominal time for all subsequent doses and associated samples. A sample obtained outside of the allotted PK visit windows is considered a protocol deviation. The timing for the next sample collection remains relative to the nominal time of the start of dose administration on Day 1.

Blood samples for determination of serum drug concentrations are collected before administration of study drug at the time points and within the windows indicated in the Schedule of Assessments. For Day 1 of the SC group and Days 1 and 15 of the IV group, a postdose blood sample is collected within 30 minutes of the end of the infusion. For Day 57 of the IV group, a blood sample is collected during the site visit; no dose is administered on Day 57. The date and time (24-hour clock time) of each sample acquisition is recorded.

In the event of breakthrough hemolysis an additional PK sample is required. Unused samples may be retained for a period of up to 5 years to perform additional ravulizumab-related assessments as necessary.

Serum ravulizumab concentration over time are evaluated with primary endpoint ($C_{trough}$ at Day 71) as the main PK parameter of interest. Other PK parameters may be explored.

17. Pharmacodynamics

Free C5 concentrations are evaluated over time. Blood samples are collected before administration of study drug at the time points and within the windows indicated in the Schedule of Assessments. For Day 1 of the SC group and Days 1 and 15 of the IV group, a postdose blood sample is collected within 30 minutes of the end of the infusion. For Day 57 of the IV group, a blood sample is collected during the site visit; no dose is administered on Day 57. Samples obtained outside of the allotted visit windows are considered protocol deviations. In the event of breakthrough hemolysis, an additional PD sample is required. Unused samples may be retained for a period of up to 5 years to perform additional assessments as necessary.

Additional details on sample collection, including blood volume requirements, are provided in the laboratory manual.

18. Statistical Methods and Planned Analyses

The statistical hypothesis is that the Day 71 $C_{trough}$ concentration of patients treated with ravulizumab SC via an OBDS is noninferior to that of patients treated with ravulizumab IV.

Assuming the ratio of the geometric means of $C_{trough}$ (SC/IV) is 1.03 and the coefficient of variation is 0.4, 62 patients in the ravulizumab SC group and 31 patients in the ravulizumab IV comparison group achieve 90% power to detect noninferiority using a one-sided test at an alpha level of 0.05 and a PK noninferiority boundary (NIB) of 0.8. The alpha level and NIB are based on recommendations in guidance documents "Standard Approaches to Establishing Bioequivalence" and "Guideline on the Investigation of Bioequivalence", from the US Food and Drug Administration and European Medicines Agency, respectively. This sample size is increased to 105 patients (70 patients in the ravulizumab SC group and 35 patients in the ravulizumab IV group) to account for the possibility that up to 10% of patients may not meet the criteria for inclusion in the PK analysis set. An interim analysis to evaluate futility and perform a sample size re-estimation is performed. This sample size re-estimation may lead to an increase of up to 144 patients (up to 96 patients in the ravulizumab SC group and 48 patients in the ravulizumab IV comparison group).

The populations for analyses are defined in Table 12. Dosing windows for inclusion in the PK analysis set are presented in Table 13.

TABLE 12

Populations for Analyses

| Population | Description |
|---|---|
| Enrolled | All patients who sign the Informed Consent Form (ICF) and who are randomized. |
| PD analysis set | All patients who receive at least 1 dose of ravulizumab and who have evaluable PD data. |
| PK analysis set | All patients who have evaluable PK data[a] and for whom: 1. All doses up to Day 64 are compliant with the planned dose and the dosing time windows specified in Table. 2. The predose PK sample on Day 71 has been collected within ±3 hours from the nominal time of the first dose on Day 1. |
| Per protocol analysis set | All patients in the PK analysis set who satisfied all key eligibility criteria for the study (inclusion criteria 2, 3, 4, 6, 8 and exclusion criteria 1 through 4; as described in Section 5). |
| Full analysis set | All patients who receive at least 1 dose of ravulizumab. |
| Safety analysis set | All patients who receive at least 1 dose of ravulizumab. Patients will be analyzed according to the study drug they actually received. |

[a]Evaluable PK data are defined as non missing results generated from samples that comply with sample integrity requirements during sample collection, storage, shipment, and bioanalysis.

TABLE 13

Dosing Window Requirements for Inclusion in the Pharmacokinetic Analysis Set

| Study Day | 15 | 22 | 29 | 36 | 43 | 50 | 57 | 64 |
|---|---|---|---|---|---|---|---|---|
| Window for dosing to be compliant for inclusion in the PK analysis set (nominal time in hours from the start of the first dose on Day 1) | ±3 | ±6 | ±6 | ±6 | ±6 | ±6 | ±3 | ±3 |

The PK analysis set is used for the primary analysis.

All data and all outcomes derived from the data is presented in detailed data listings or summary tabulations. Graphical can may also be provided when appropriate. All analyses will be performed using SAS® release, version 9.4 or higher (SAS Institute Inc., Cary, NC, USA) or other validated statistical software. Continuous variables are summarized using descriptive statistics, including number of observations and mean, standard deviation, median, minimum, and maximum values. Categorical variables are summarized by frequency counts and percentage of patients.

Details of the statistical analyses described below are specified in a separate Statistical Analysis Plan (SAP) before database lock and analysis. Any change to the data analysis methods described in the protocol requires an amendment only if it changes the primary objective or the study conduct. Any other change to the data analysis methods described in the protocol or SAP, and the justification for making the change, are described in the clinical study report. Additional exploratory analyses of the data may be conducted as deemed appropriate.

The primary analysis to evaluate noninferiority in serum $C_{trough}$ of ravulizumab SC compared with ravulizumab IV is conducted after all patients have completed all protocol-required assessments in the Randomized Treatment Period.

The primary analysis is performed on the PK analysis set.

The primary endpoint is the Day 71 serum ravulizumab $C_{trough}$. The ratio of the geometric mean $C_{trough}$ from the ravulizumab SC group over the geometric mean $C_{trough}$ from ravulizumab IV group with a 2-sided 90% CI is calculated. If the lower bound of the 90% CI for the ratio of the geometric means (ravulizumab SC/ravulizumab IV) is greater than the NIB of 80%, then the ravulizumab SC treatment is concluded to be noninferior to the ravulizumab IV treatment.

To obtain the above referenced 90% CI, the $C_{trough}$ data under consideration is analyzed using analysis of variance. In addition to the formulation (SC or IV), the model for statistical analysis takes into account body weight. The data is transformed prior to analysis using a logarithmic transformation. The point estimate and CIs is calculated and constructed for the mean difference of log-transformed parameters. These are then be back-transformed to be presented on the ratio scale.

Sensitivity analyses are performed by repeating the primary analysis on the Full Analysis Set (FAS) patients with evaluable PK data and the Per Protocol Set (PPS).

Secondary analyses are performed on the Full Analysis Set (FAS). When applicable, results from the Randomization Treatment Period are presented in parallel by treatment group, but no formal comparisons will be performed. Summaries of data over time while patients are receiving SC administration of ravulizumab are based on time since first exposure to ravulizumab SC. At the start of the Extension Period, it has been 56 days since their first dose of ravulizumab SC for patients randomized to the SC group, while patients initially randomized to the IV group are getting their first dose of ravulizumab SC. This exposure difference is taken into account and, as an example, a summary for Day 183 (since first dose of ravulizumab SC) use sstudy Day 183 data from patients randomized to the SC group and study Day 239 data from patients randomized to the IV group.

Pharmacokinetic analyses is performed for all patients from the FAS who have evaluable PK data, as described in PK analysis set. Since this is a multicenter patient study censoring of PK or PD data may be considered when a sample collection or handling error is inferred.

Graphs of mean serum ravulizumab concentrations versus time is constructed. Graphs of serum concentrations versus time for individual patients may also be provided. Actual dose administration and sampling times are used for all calculations. Descriptive statistics are calculated for serum concentration data at each sampling time as appropriate.

Pharmacodynamic analyses are performed for all patients from the FAS who have evaluable PD data. The PD effects of ravulizumab is evaluated by assessing the absolute values for free C5 serum concentrations over time. Descriptive statistics are calculated for the PD data at each sampling time as appropriate. Additional assessments of serum free C5 concentration may be considered as appropriate.

Quality of life is evaluated using FACIT-Fatigue Version 4 Questionnaire, as well as the EORTC QLQ-C30 Version 3.0 questionnaire. The data from these questionnaires is summarized at Baseline and Day 183, as well as each applicable postbaseline time point using descriptive statistics for continuous variables for the observed value, as well as the change from Baseline.

Patient satisfaction with treatment is evaluated using TASQ scores. These data are summarized at Baseline and Day 183, as well as each applicable postbaseline time point using descriptive statistics for continuous variables for the observed value as well as the change from Baseline. Any safety data generated from this questionnaire is documented as an adverse event on the AE eCRF as per the Investigator's medical judgement.

Lactate dehydrogenase is summarized at Baseline and each applicable postbaseline time point using descriptive statistics for continuous variables for the observed value, as well as the change from Baseline.

The number and proportion of patients with breakthrough hemolysis are summarized over time by presenting the number and proportion of patients with a breakthrough along with a 2-sided 95% CI for each applicable postbaseline time point. The number and proportion of patients who do not require a transfusion and the number and proportion of patients with stabilized hemoglobin are summarized similarly.

All safety analyses are conducted for the Safety Set, defined as all patients who receive at least 1 dose of ravulizumab.

The following definitions are used for AEs and ADEs. A pretreatment adverse event is any adverse event that starts after providing informed consent, but before the first infusion of study drug. A treatment-emergent AE (TEAE) is any adverse event that starts during or after the first infusion of study drug. All ADEs are by definition occurring during or after the start of the first infusion.

The incidence of TEAEs is summarized by System Organ Class (SOC) and Preferred Term overall, by severity, and by relationship to treatment. The incidence of SAEs is also summarized. The incidence of ADEs and SADEs is summarized similarly by SOC and Preferred Term and by severity. All AEs and ADEs are coded using Medical Dictionary for Regulatory Activities, version 18 or higher.

Adverse changes from Baseline in physical examination findings are classified as adverse events and analyzed accordingly.

Observed values and changes from Baseline (last assessment prior to ravulizumab) in ECGs, vital signs, and laboratory assessments are summarized for all applicable study visits. For laboratory results that can be classified as normal, low, or high based on normal range values, shifts from baseline in classification is summarized for all applicable study visits.

Changes from Baseline in ECG intervals (PR, RR, QT, and QTcF) are summarized for all applicable study visits. The QT interval is corrected for heart rate using Fridericia's formula (QTcF).

For the immunogenicity data the number and proportion of patients who develop ADAs to ravulizumab and the titer values are summarized. The proportion of patients with at least 1 positive ADA result over time (ever positive) and the proportion of patients always negative may be explored.

Device performance is evaluated by the number and proportion of doses that were completely administered successfully out of all attempted full-dose administration. The reasons for doses not being completely administered are summarized. For reasons reported as "device-related technical failure" these technical failures are further summarized by category.

Additional exploration of PK, PD, ravulizumab OBDS performance data, and patient reported outcomes may be performed as considered necessary.

An interim analysis is performed when 50% of the planned patients (n=105) have been assessed for the primary endpoint (i.e., 34 patients in the ravulizumab SC group and 17 patients in the ravulizumab IV comparison group). This is expected to yield at least 45 patients who meet the criteria for inclusion in the PK analysis set.

The initial part of the analysis is to assess futility in order to allow the Sponsor to stop the study early if it is unlikely to lead to a significant final result. This will conserve resources and not expose additional patients to the study drug in the event that noninferiority appears very unlikely.

Following the futility assessment, but using the same set of patients and data, an interim sample size re-estimation analysis to reassess the required size of the study based on estimation of the primary endpoint is also performed.

Enrollment of patients proceeds without interruption while the analysis is ongoing.

There are no plans to stop the study for demonstration of noninferiority at the interim analysis.

A nonbinding futility boundary based on conditional power for noninferiority (CPni) of 20% is used so that if the Sponsor decides to continue the study, even if the futility boundary is crossed, there is no impact to the primary analysis Type I error rate.

The sample size re-estimation (SSR) analysis is also based on the CPni calculated using the results obtained at this interim analysis. The CPni is calculated assuming the 'observed effect' values; i.e., the population mean $C_{trough}$ equals the sample mean $C_{trough}$ at the time of the sample size re-estimation. The maximum total number of patients is 144. The sample size is never reduced from the planned sample size of 105 patients. If the CPni is at least 90% for the planned total sample size of 105 patients, then no increase in sample size is made.

The decision made based on this sample size re-estimation analysis follows the following rule (see Table 14):

If CPmin≤CPni<0.9, increase the sample size by just the right amount such that CPni is increased to 90%, subject to a cap of 144 patients. The range CPmin≤CPni<0.9 is called the promising zone for noninferiority. Specifically, if CPni is in its promising zone, this decision rule increases the sample size, to the smaller of 144 patients or the number needed to boost CPni to 90%.

TABLE 14

| Criteria for Futility Analysis and Sample Size Re-estimation | |
| --- | --- |
| | Decision |
| CPni ≤ 20% | Consider stopping for futility |
| 20% < CPni < CPmin % | Continue to N = 105 |

TABLE 14-continued

| Criteria for Futility Analysis and Sample Size Re-estimation | |
|---|---|
| | Decision |
| CPmin % ≤ CPni < 90% | Increase to smaller of N = 144 or N needed for CPni = 90% |
| 90% ≤ CPni | Continue to N = 105 |

Abbreviations: CPmin = CPni = conditional power for noninferiority; N = number [of patients].

The lower bound of the promising zone, CPmin, is determined following the approach explained in Mehta et al. (Mehta et al., Stat Medicine. 2011; 30:3267-3284) and is not explicitly stated here to avoid potential study bias following any decision made based on this sample size re-estimation analysis. Further details are provided in the SAP.

If a Day 1 assessment is missing the Screening assessment is used as the Baseline assessment.

Missing data for HRQoL instruments are handled as specified in the instructions for each instrument.

Example 2: Interim Results from Phase 3 Clinical Trial

A Phase 3, randomized, parallel-group, multicenter, open-label, PK non-inferiority study (referred to as "ALXN1210-PNH-303") of ravulizumab (ULTOMIRIS®) administered subcutaneously (RAV-SC) versus ravulizumab administered intravenously (RAV-IV) was conducted in adult patients with PNH who have been stable on eculizumab (SO-LIRIS®) for ≥3 months, substantially according to the protocol set forth above in Example 1.

Specifically, this study is a Phase 3, randomized, parallel-group, open-label, PK non-inferiority study of RAV-SC versus RAV-IV. Switch was conducted in adult patients with PNH who have been stable on eculizumab for ≥3 months. Randomization (2:1, SC vs IV) was stratified by baseline weight category (≥40 to <60 kg and ≥60 to <100 kg). The randomized treatment period was 2:1 randomization into treatment arms (ravRAV-SC vs RAV-IV) for 10 weeks.

136 participants were enrolled and received at least one dose. All 7 participants from site 0657 were excluded from main analysis sets due to source documentation deviations. One participant discontinued prior to completion of the Randomized Treatment Period. 113 patients are included in the Primary Analysis Set (PK Analysis Set).

Figure 5:
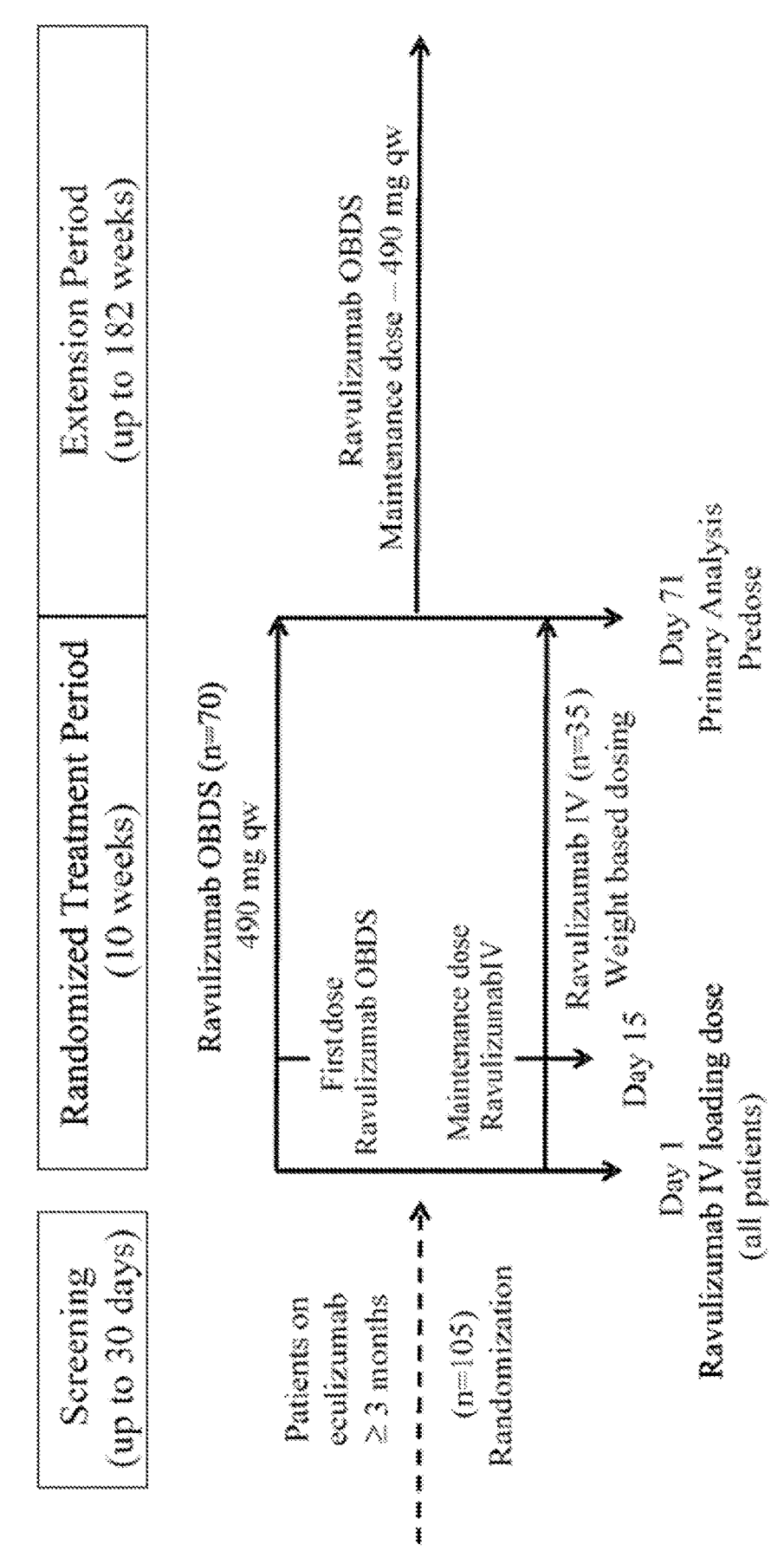
FIG. 5 is a schematic depicting the design of the Phase 3 noninferiority study of ravulizumab (ULTOMIRIS®)

All patients received a weight based IV loading dose at day 1. From day 15 to 71: patients received either QW SC doses (490 mg via 2 RAV-OBDS) or a single Q8W RAV IV maintenance dose. For the extension period all patients self-administered QW SC doses (490 mg via 2 RAV-OBDS) up to 182 weeks. The sample size was 105 (70 SC and 35 IV). Futility analysis and sample size re-estimation analysis were conducted when 50% of the planned total sample size completed the primary endpoint assessment (conducted in January 2020). There was no enrollment pause. The study scheme is set forth in FIG. 5. The patient disposition and analysis sets are summarized in FIG. 6. Patient demographics and baseline characteristics are set forth in FIGS. 7A-7B.

The specific dosing is as follows:

Ravulizumab SC dosage: Day 1 loading dose (IV)=2400 mg for patients weighing ≥40 kg to <60 kg and 2700 mg for patients weighing ≥60 kg to <100 kg; Day 15 and Extension Period maintenance doses (SC)=490 mg qw for all patients.

Ravulizumab IV dosage: Day 1 loading dose (IV)=2400 mg for patients weighing ≥40 mg to <60 kg and 2700 mg for patients weighing ≥60 kg to <100 kg; Day 15 maintenance dose (IV)=3000 mg for patients weighing ≥40 kg to <60 kg, 3300 mg for patients weighing ≥60 kg to <100 kg.

Extension Period maintenance doses (SC)=490 mg qw for all patients.

A. Objectives and Endpoints

The primary objective was to demonstrate the non-inferiority in ravulizumab trough concentration for subcutaneous administration versus intravenous administration. The primary endpoint was Day 71 serum ravulizumab trough concentration (Ctrough). Data is included is from the 10 weeks Randomized Treatment Period on all patients who have not previously discontinued from the study.

The safety objective was to evaluate the safety of ravulizumab administered subcutaneously and the ravulizumab on-body delivery system (OBDS). Safety endpoints included physical exams, vital signs, laboratory assessments, adverse events (AEs) including adverse device effects (ADEs).

Secondary objectives and endpoints included (1) characterizing PK, PD, and immunogenicity of ravulizumab SC (i.e., $C_{trough}$ over time, free C5, and anti-drug antibodies), (2) evaluating health related quality of life and treatment satisfaction on ravulizumab SC (i.e., FACIT-Fatigue, EORTC QLQ-30, treatment administration satisfaction questionnaire), (3) evaluating efficacy of ravulizumab SC (i.e., LDH, breakthrough hemolysis, transfusion avoidance, stable hemoglobin, PNH symptomatology), and (4) assessing performance of ravulizumab OBDS (i.e., reported outcome of attempted full-dose administrations). The interim endpoints are through June 2020 and are limited to data from the randomized treatment period (10 weeks)

B. Primary Analysis

The primary analysis was performed on the PK analysis set. This includes all patients who have evaluable PK data for whom: (1) all doses up to Day 64 are compliant with the planned dose and the protocol specified dosing time windows and (2) the predose PK sample on Day 71 has been collected within +3 hours from the nominal time of the first dose on Day 1.

There is a 90% CI for the ratio of the geometric means (ravulizumab SC/ravulizumab IV). This was done using a weighted test statistic to account for sample size re-estimation interim analysis and avoid inflation of type 1 error. If the lower bound of the CI was greater than the noninferiority bound (NIB) of 80%, then noninferiority was claimed.

Analysis included: (1) ANOVA controlling for treatment (SC and IV) and body weight category, (2) $C_{trough}$ data log transformed prior to analysis, (3) point estimate and CI constructed for the difference of means of log transformed data, and (4) back-transformed to present on the ratio scale.

C. Other Analysis Sets:

Per protocol set, all patients in the PK set who also satisfied all of the following criteria:

(1) Met the following inclusion criteria:

1: Treated with eculizumab according to the labeled dosing recommendation for PNH (900 mg every 14 days+2 days) for at least 3 months prior to study entry with no missed doses within 2 months prior to study entry and no more than 2 doses outside of the visit window.

2: Lactate dehydrogenase levels ≤1.5×ULN, according to central laboratory, at Screening. Sample must be obtained within 24 hours of or immediately prior to a scheduled eculizumab dose administration (ie, at trough eculizumab level).

3: Documented diagnosis of PNH confirmed by high-sensitivity flow cytometry evaluation.

4: Body weight ≥40 to <100 kg, and in the opinion of the Investigator, are likely to remain within this body weight range for the duration of the study.

5: Patients must be willing and able to give written informed consent and to comply with all study visits and procedures, including self-administration of ravulizumab SC doses, and the use of any data collection device(s) to directly record patient data.

(2) Did not meet any of the following exclusion criteria:

1: More than 1 LDH value >2×ULN within the 3 months prior to study entry.

2: MAVE in the 6 months prior to study entry.

3: Platelet count <30,000/mm3 (30×109/L) at Screening.

4: Absolute neutrophil count <500/µL (0.5×109/L) at Screening

The PD Analysis Set included all patients who received at least 1 dose of ravulizumab and who had evaluable PD data. The Full Analysis Set and Safety Set included all patients (except those from site 0657) in the enrolled analysis set who received at least 1 dose of ravulizumab. The Modified Full Analysis Set and Modified Safety Set included all patients in the FAS and Safety Set, but also included patients from site 0657 with at least 1 dose of ravulizumab.

D. Results:

The primary PK noninferiority analysis is set forth in FIG. 8. The Stage 1 population is all patients included in the sample size re-estimation analysis. The Stage 2 population is all patients not analyzed as part of the sample size re-estimation analysis. A mixed model was performed on log-transformed parameters and includes treatment and stratified weight group as fixed effects. Geometric least square means are the least square means from the mixed model after back transformation to the original scale. The 90% confidence interval is presented after back transformation to the original scale. The z-score is calculated at each stage and shown as a combined score using the pre-specified weights of 0.5 and 0.5. Statistical significance was reached if the weighted overall z-score is >1.645. A Forest Plot of PK noninferiority is set forth in FIG. 9. The mean serum ravulizumab concentration is set forth in FIG. 10. Free C5 concentration is depicted in FIG. 11

Non-inferiority of subcutaneous versus intravenous trough ravulizumab concentration was demonstrated in the PK Analysis set. There was a Geometric Mean Ratio (GMR) of 1.257 with 90% CI (1.160, 1.361), p-value <0.0001. With respect to pharmacokinetics (PK) and pharmacodynamics (PD), in both treatment groups, all free C5 results obtained after the first dose through the Randomized Treatment Period were ≤0.5 µg/mL (i.e., the defined threshold for complete terminal complement inhibition). Subcutaneous dosing resulted in ravulizumab exposures ≥175 µg/mL, defined as threshold for complete complement inhibition, for all subjects with no unexpected PK findings. No participants with treatment emergent positive result for ADAs were observed.

With respect to efficacy, mean lactate dehydrogenase is set forth in FIG. 12, breakthrough hemolysis/transfusion avoidance is set forth in FIG. 13, and hemoglobin stability/PNH symptomatology is set forth in FIG. 14. Breakthrough hemolysis was low in both arms (i.e., for the subcutaneous arm there were no events versus one event in the intravenous arm). Transfusion avoidance was maintained in 94% and 87% of participants for both the subcutaneous and intravenous groups, respectively. Transfusion avoidance is defined as patients who remained transfusion free and did not require a transfusion after the first dose of study drug. Stable hemoglobin results were maintained in 94% and 82% of participants for the subcutaneous and intravenous group, respectively. Symptoms of PNH were observed in 45% and 47% of participants for the subcutaneous and intravenous groups, respectively.

With respect to safety, no participants were observed with treatment emergent position results for ADAs. A treatment emergent AE overview is set forth in FIG. 15 and a summary of serious adverse events is set forth in FIG. 16. There was a higher proportion of patients with at least one Adverse Event (AE) in the subcutaneous arm versus the intravenous arm with 81% and 60%, respectively. Proportions were similar when adverse device effect (ADEs) are excluded: subcutaneous (64%) versus intravenous (60%). For ADEs, 23% were injection relates and 4% were contact related. For serious adverse events (SAEs), the results for subcutaneous were 5/84 (6%) versus intravenous 1/45 (2%). No serious adverse device effects (SADEs) were reported. There were no meningococcal cases.

There were two main areas of focus for safety: (1) TEAEs (not ADE related) and (2) ADEs. TEAs had a higher incidence in the subcutaneous arm: (1) Fever—6 patients, All G1, all unrelated, (2) Asthenia—4 patients, Majority G1, 2 related and 2 unrelated, (3) Fatigue—6 patients (2 worsening of fatigue), Majority G1, 1 related, and (4) Diarrhea—10 patients (11 events), All G1, 3 related events. For ADEs, n:38 (45.2%) E=107. There were: (1) Application site events: n=3 (3.6%) E=3, (2) Injection site events n=19 (22.6%) E=73, and (3) Device use n=20 (23.8%) E=31.

E. Summary:

In summary, the primary results demonstrated non-inferiority of subcutaneous versus intravenous trough ravulizumab concentration in the PK Analysis set, with a Geometric Mean Ratio (GMR) of 1.257 with 90% CI (1.160, 1.361), p-value <0.0001. With respect to PK/PD, in both treatment groups, all free C5 results obtained after the first dose through the Randomized Treatment Period were ≤0.5 µg/mL; the defined threshold for complete terminal complement inhibition. Subcutaneous dosing resulted in ravulizumab exposures ≥175 µg/mL, defined as threshold for complete complement inhibition, for all subjects with no unexpected PK findings. No participants with treatment emergent positive result for ADAs were observed. With respect to safety, a higher proportion of patients with at least one AE in the subcutaneous arm versus the intravenous arm, with 81% and 60%, respectively. Proportions were similar when adverse device effect (ADEs) are excluded: SC 64% vs IV 60%. For ADEs, there were Admin site conditions: 26% (Injection related: 23%, Contact related: 4%). For SAEs: SC 5/84 (6%) vs IV 1/45 (2%). No SADEs were reported and there were no meningococcal cases.

With respect to efficacy, breakthrough hemolysis was low in both arm: SC (no events) versus IV (1 event). Transfusion avoidance was maintained in 94% and 87% of participants for SC and IV group, respectively. Stable hemoglobin results were maintained in 94% and 82% of participants for SC and IV group, respectively. Symptoms of PNH were observed in 45% and 47% of participants for SC and IV group, respectively.

SEQUENCE SUMMARY

SEQ ID NO: 1

GYIFSNYWIQ

SEQ ID NO: 2

EILPGSGSTEYTENFKD

-continued

```
                                       SEQ ID NO: 3
YFFGSSPNWYFDV

SEQ ID NO: 4
GASENIYGALN

SEQ ID NO: 5
GATNLAD

SEQ ID NO: 6
QNVLNTPLT

SEQ ID NO: 7
QVQLVQSGAEVKKPGASVKVSCKASGYIFSNYWIQWVRQAPGQGLEWMG

EILPGSGSTEYTENFKDRVTMTRDTSTSTVYMELSSLRSEDTAVYYCAR

YFFGSSPNWYFDVWGQGTLVTVSS

SEQ ID NO: 8
DIQMTQSPSSLSASVGDRVTITCGASENIYGALNWYQQKPGKAPKLLIY

GATNLADGVPSRFSGSGSGTDFTLTISSLQPEDFATYYCQNVLNTPLTF

GQGTKVEIK

SEQ ID NO: 9
ASTKGPSVFPLAPCSRSTSESTAALGCLVKDYFPEPVTVSWNSGALTSG

VHTFPAVLQSSGLYSLSSVVTVPSSNFGTQTYTCNVDHKPSNTKVDKTV

ERKCCVECPPCPAPPVAGPSVFLFPPKPKDTLMISRTPEVTCVVVDVSQ

EDPEVQFNWYVDGVEVHNAKTKPREEQFNSTYRVVSVLTVLHQDWLNGK

EYKCKVSNKGLPSSIEKTISKAKGQPREPQVYTLPPSQEEMTKNQVSLT

CLVKGFYPSDIAVEWESNGQPENNYKTTPPVLDSDGSFFLYSRLTVDKS

RWQEGNVFSCSVMHEALHNHYTQKSLSLSLGK

SEQ ID NO: 10
QVQLVQSGAEVKKPGASVKVSCKASGYIFSNYWIQWVRQAPGQGLEWMG

EILPGSGSTEYTENFKDRVTMTRDTSTSTVYMELSSLRSEDTAVYYCAR

YFFGSSPNWYFDVWGQGTLVTVSSASTKGPSVFPLAPCSRSTSESTAAL

GCLVKDYFPEPVTVSWNSGALTSGVHTFPAVLQSSGLYSLSSVVTVPSS

NFGTQTYTCNVDHKPSNTKVDKTVERKCCVECPPCPAPPVAGPSVFLFP

PKPKDTLMISRTPEVTCVVVDVSQEDPEVQFNWYVDGVEVHNAKTKPRE

EQFNSTYRVVSVLTVLHQDWLNGKEYKCKVSNKGLPSSIEKTISKAKGQ

PREPQVYTLPPSQEEMTKNQVSLTCLVKGFYPSDIAVEWESNGQPENNY

KTTPPVLDSDGSFFLYSRLTVDKSRWQEGNVFSCSVMHEALHNHYTQKS

LSLSLGK

SEQ ID NO: 11
DIQMTQSPSSLSASVGDRVTITCGASENIYGALNWYQQKPGKAPKLLIY

GATNLADGVPSRFSGSGSGTDFTLTISSLQPEDFATYYCQNVLNTPLTF

GQGTKVEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC

SEQ ID NO: 12
QVQLVQSGAEVKKPGASVKVSCKASGHIFSNYWIQWVRQAPGQGLEWMG

EILPGSGHTEYTENFKDRVTMTRDTSTSTVYMELSSLRSEDTAVYYCAR

YFFGSSPNWYFDVWGQGTLVTVSS
```

-continued

```
                                       SEQ ID NO: 13
ASTKGPSVFPLAPCSRSTSESTAALGCLVKDYFPEPVTVSWNSGALTSG

VHTFPAVLQSSGLYSLSSVVTVPSSNFGTQTYTCNVDHKPSNTKVDKTV

ERKCCVECPPCPAPPVAGPSVFLFPPKPKDTLMISRTPEVTCVVVDVSQ

EDPEVQFNWYVDGVEVHNAKTKPREEQFNSTYRVVSVLTVLHQDWLNGK

EYKCKVSNKGLPSSIEKTISKAKGQPREPQVYTLPPSQEEMTKNQVSLT

CLVKGFYPSDIAVEWESNGQPENNYKTTPPVLDSDGSFFLYSRLTVDKS

RWQEGNVFSCSVLHEALHSHYTQKSLSLSLGK

SEQ ID NO: 14
QVQLVQSGAEVKKPGASVKVSCKASGHIFSNYWIQWVRQAPGQGLEWMG

EILPGSGHTEYTENFKDRVTMTRDTSTSTVYMELSSLRSEDTAVYYCAR

YFFGSSPNWYFDVWGQGTLVTVSSASTKGPSVFPLAPCSRSTSESTAAL

GCLVKDYFPEPVTVSWNSGALTSGVHTFPAVLQSSGLYSLSSVVTVPSS

NFGTQTYTCNVDHKPSNTKVDKTVERKCCVECPPCPAPPVAGPSVFLFP

PKPKDTLMISRTPEVTCVVVDVSQEDPEVQFNWYVDGVEVHNAKTKPRE

EQFNSTYRVVSVLTVLHQDWLNGKEYKCKVSNKGLPSSIEKTISKAKGQ

PREPQVYTLPPSQEEMTKNQVSLTCLVKGFYPSDIAVEWESNGQPENNY

KTTPPVLDSDGSFFLYSRLTVDKSRWQEGNVFSCSVLHEALHSHYTQKS

LSLSLGK

SEQ ID NO: 15
ASTKGPSVFPLAPCSRSTSESTAALGCLVKDYFPEPVTVSWNSGALTSG

VHTFPAVLQSSGLYSLSSVVTVTSSNFGTQTYTCNVDHKPSNTKVDKTV

ERKCCVECPPCPAPPVAGPSVFLFPPKPKDTLYITREPEVTCVVVDVSH

EDPEVQFNWYVDGMEVHNAKTKPREEQFNSTFRVVSVLTVVHQDWLNGK

EYKCKVSNKGLPAPIEKTISKTKGQPREPQVYTLPPSREEMTKNQVSLT

CLVKGFYPSDIAVEWESNGQPENNYKTTPPMLDSDGSFFLYSKLTVDKS

RWQQGNVFSCSVMHEALHNHYTQKSLSLSPGK

SEQ ID NO: 16
QVQLVQSGAEVKKPGASVKVSCKASGYIFSNYWIQWVRQAPGQGLEWMG

EILPGSGSTEYTENFKDRVTMTRDTSTSTVYMELSSLRSEDTAVYYCAR

YFFGSSPNWYFDVWGQGTLVTVSSASTKGPSVFPLAPCSRSTSESTAAL

GCLVKDYFPEPVTVSWNSGALTSGVHTFPAVLQSSGLYSLSSVVTVTSS

NFGTQTYTCNVDHKPSNTKVDKTVERKCCVECPPCPAPPVAGPSVFLFP

PKPKDTLYITREPEVTCVVVDVSHEDPEVQFNWYVDGMEVHNAKTKPRE

EQFNSTFRVVSVLTVVHQDWLNGKEYKCKVSNKGLPAPIEKTISKTKGQ

PREPQVYTLPPSREEMTKNQVSLTCLVKGFYPSDIAVEWESNGQPENNY

KTTPPMLDSDGSFFLYSKLTVDKSRWQQGNVFSCSVMHEALHNHYTQKS

LSLSPGK

SEQ ID NO: 17
GASENIYHALN

SEQ ID NO: 18
EILPGSGHTEYTENFKD

SEQ ID NO: 19
GHIFSNYWIQ
```

-continued

SEQ ID NO: 20

QVQLVQSGAEVKKPGASVKVSCKASGHIFSNYWIQWVRQAPGQGLEWMG

EILPGSGHTEYTENFKDRVTMTRDTSTSTVYMELSSLRSEDTAVYYCAR

YFFGSSPNWYFDVWGQGTLVTVSSASTKGPSVFPLAPCSRSTSESTAAL

GCLVKDYFPEPVTVSWNSGALTSGVHTFPAVLQSSGLYSLSSVVTVPSS

NFGTQTYTCNVDHKPSNTKVDKTVERKCCVECPPCPAPPVAGPSVFLFP

PKPKDTLMISRTPEVTCVVVDVSQEDPEVQFNWYVDGVEVHNAKTKPRE

EQFNSTYRVVSVLTVLHQDWLNGKEYKCKVSNKGLPSSIEKTISKAKGQ

PREPQVYTLPPSQEEMTKNQVSLTCLVKGFYPSDIAVEWESNGQPENNY

KTTPPVLDSDGSFFLYSRLTVDKSRWQEGNVFSCSVMHEALHNHYTQKS

LSLSLGK

SEQ ID NO: 21

SYAIS

SEQ ID NO: 22

GIGPFFGTANYAQKFQG

SEQ ID NO: 23

DTPYFDY

SEQ ID NO: 24

SGDSIPNYYVY

SEQ ID NO: 25

DDSNRPS

SEQ ID NO: 26

QSFDSSLNAEV

SEQ ID NO: 27

QVQLVQSGAEVKKPGSSVKVSCKASGGTFSSYAISVWRQAPGQGLEWMG

GIGPFFGTANYAQKFQGRVTITADESTSTAYMELSSLRSEDTAVYYCAR

DTPYFDYWGQGTLVTVSS

SEQ ID NO: 28

DIELTQPPSVSVAPGQTARISCSGDSIPNYYVYWYQQKPGQAPVLVIYD

DSNRPSGIPERFSGSNSGNTATLTISGTQAEDEADYYCQSFDSSLNAEV

FGGGTKLTVL

SEQ ID NO: 29

NYIS

SEQ ID NO: 30

IIDPDDSYTEYSPSFQG

SEQ ID NO: 31

YEYGGFDI

SEQ ID NO: 32

SGDNIGNSYVH

SEQ ID NO: 33

KDNDRPS

SEQ ID NO: 34

GTYDIESYV

SEQ ID NO: 35

EVQLVQSGAEVKKPGESLKISCKGSGYSFTNYISWVRQMPGKGLEWMGI

IDPDDSYTEYSPSFQGQVTISADKSISTAYLQWSSLKASDTAMYYCARY

EYGGFDIWGQGTLVTVSS

-continued

SEQ ID NO: 36

SYELTQPPSVSVAPGQTARISCSGDNIGNSYVHWYQQKPGQAPVLVIYK

DNDRPSGIPERFSGSNSGNTATLTISGTQAEDEADYYCGTYDIESYVFG

GGTKLTVL

SEQ ID NO: 37

SSYYVA

SEQ ID NO: 38

AIYTGSGATYKASWAKG

SEQ ID NO: 39

DGGYDYPTHAMHY

SEQ ID NO: 40

QASQNIGSSLA

SEQ ID NO: 41

GASKTHS

SEQ ID NO: 42

QSTKVGSSYGNH

SEQ ID NO: 43

QVQLVESGGGLVQPGGSLRLSCAASGFTSHSSYYVAWVRQAPGKGLEWV

GAIYTGSGATYKASWAKGRFTISKDTSKNQVVLTMTNMDPVDTATYYCA

SDGGYDYPTHAMHYWGQGTLVTVSS

SEQ ID NO: 44

DVVMTQSPSSLSASVGDRVTITCQASQNIGSSLAWYQQKPGQAPRLLIY

GASKTHSGVPSRFSGSGSGTDFTLTISSLQPEDVATYYCQSTKVGSSYG

NHFGGGTKVEIK

SEQ ID NO: 45

QVQLVESGGGLVQPGRSLRLSCAASGFTVHSSYYMAWVRQAPGKGLEWV

GAIFTGSGAEYKAEWAKGRVTISKDTSKNQVVLTMTNMDPVDTATYYCA

SDAGYDYPTHAMHYWGQGTLVTVSSASTKGPSVFPLAPSSKSTSGGTAA

LGCLVKDYFPEPVTVSWNSGALTSGVHTFPAVLQSSGLYSLSSVVTVPS

SSLGTQTYICNVNHKPSNTKVDKKVEPKSCDKTHTCPPCPAPELRRGPK

VFLFPPKPKDTLMISRTPEVTCVVVDVSHEDPEVKFNWYVDGVEVHNAK

TKPREEQYNSTYRVVSVLTVLHQDWLNGKEYKCKVSNKGLPSSIEKTIS

KAKGQPREPQVYTLPPSREEMTKNQVSLTCLVKGFYPSDIAVEWESNGQ

PENNYKTTPPVLDSDGSFFLYSKLTVDKSRWQQGNVFSCSVLHEALHAH

YTRKELSLSP

SEQ ID NO: 46

DIQMTQSPSSLSASVGDRVTITCRASQGISSSLAWYQQKPGKAPKLLIY

GASETESGVPSRFSGSGSGTDFTLTISSLQPEDFATYYCQNTKVGSSYG

NTFGGGTKVEIKRTVAAPSVFIFPPSDEQLKSGTASVVCLLNNFYPREA

KVQWKVDNALQSGNSQESVTEQDSKDSTYSLSSTLTLSKADYEKHKVYA

CEVTHQGLSSPVTKSFNRGEC

SEQ ID NO: 47

QVQLQESGPGLVKPSETLSLTCTVSGDSVSSSYWTWIRQPPGKGLEWIG

YIYYSGSSNYNPSLKSRATISVDTSKNQFSLKLSSVTAADTAVYYCARE

GNVDTTMIFDYWGQGTLVTVSS

-continued                                          -continued

SEQ ID NO: 48

AIQMTQSPSSLSASVGDRVTITCRASQGIRNDLGWYQQKPGKAPKLLIY

AASSLQSGVPSRFAGRGSGTDFTLTISSLQPEDFATYYCLQDFNYPWTF

GQGTKVEIK

SEQ ID NO: 49

QVQLQESGPGLVKPSETLSLTCTVSGDSVSSSYWTWIRQPPGKGLEWIG

YIYYSGSSNYNPSLKSRATISVDTSKNQFSLKLSSVTAADTAVYYCARE

GNVDTTMIFDYWGQGTLVTVSSASTKGPSVFPLAPCSRSTSESTAALGC

LVKDYFPEPVTVSWNSGALTSGVHTFPAVLQSSGLYSLSSVVTVPSSSL

GTKTYTCNVDHKPSNTKVDKRVESKYGPPCPPCPAPEFLGGPSVFLFPP

KPKDTLMISRTPEVTCVVVDVSQEDPEVQFNWYVDGVEVHNAKTKPREE

QFNSTYRVVSVLTVLHQDWLNGKEYKCKVSNKGLPSSIEKTISKAKGQP

REPQVYTLPPSQEEMTKNQVSLTCLVKGFYPSDIAVEWESNGQPENNYK

TTPPVLDSDGSFFLYSRLTVDKSRWQEGNVFSCSVMHEALHNHYTQKSL

SLSLGK

SEQ ID NO: 50

AIQMTQSPSSLSASVGDRVTITCRASQGIRNDLGWYQQKPGKAPKLLIY

AASSLQSGVPSRFAGRGSGTDFTLTISSLQPEDFATYYCLQDFNYPWTF

GQGTKVEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC

---

What is claimed is:

1. A method of treating a human patient with a complement-associated condition, the method comprising administering to the patient during an administration cycle an effective amount of an anti-C5 antibody or antigen binding fragment thereof, comprising CDR1, CDR2 and CDR3 heavy chain sequences as set forth in SEQ ID NOs: 19, 18 and 3, respectively, and CDR1, CDR2 and CDR3 light chain sequences as set forth in SEQ ID NOs: 4, 5 and 6, respectively, wherein the anti-C5 antibody or antigen binding fragment thereof is administered subcutaneously (SC) by an on-body delivery system (OBDS), and wherein the OBDS comprises a pharmaceutical formulation comprising ravulizumab (70 mg/mL) in 50 mM sodium phosphate, 25 mM arginine, 5% sucrose, 0.05% polysorbate 80, and water for injection.

2. The method of claim 1, wherein the anti-C5 antibody or antigen binding fragment thereof is administered every week thereafter at a dose of 490 mg.

3. The method of claim 1, wherein the human patient receives an intravenous loading dose prior to subcutaneous administration.

4. The method of claim 3, wherein the loading dose is weight-based, wherein i. a dose of 2400 mg is administered to a patient weighing ≥40 to <60 kg, or ii. a dose of 2700 mg is administered to a patient weighing ≥60 to <100 kg.

5. The method of claim 1, wherein the anti-C5 antibody or antigen binding fragment thereof further comprises a variant human Fc constant region that binds to human neonatal Fc receptor (FcRn), wherein the variant human Fc CH3 constant region comprises Met-429-Leu and Asn-435-Ser substitutions at residues corresponding to methionine 428 and asparagine 434 of a native human IgG Fc constant region, each in EU numbering.

6. The method of claim 3, wherein the anti-C5 antibody or antigen binding fragment thereof is administered subcutaneously on Day 15 of the administration cycle and for at least seven weeks thereafter at a dose of 490 mg qlw.

7. The method of claim 6, wherein the administration cycle is a total of 10 weeks of treatment.

8. The method of claim 2, wherein the anti-C5 antibody or antigen binding fragment thereof is administered subcutaneously at a dose of 490 mg qlw for up to 3 months, 6 months, 9 months, 12 months, 15 months, 18 months, 21 months, two years or chronically for the remainder of the patient's life.

9. The method of claim 1, wherein the patient has previously been treated with eculizumab.

10. The method of claim 9, wherein the administration cycle starts at least two weeks after the patient's last dose of eculizumab.

11. The method of claim 1, wherein the anti-C5 antibody or antigen-binding fragment thereof, comprises a heavy chain variable region of SEQ ID NO: 12 and a light chain variable region of SEQ ID NO: 8.

12. The method of claim 1, wherein the anti-C5 antibody or antigen-binding fragment thereof, further comprises a heavy chain constant region of SEQ ID NO: 13.

13. The method of claim 1, wherein the antibody or antigen-binding fragment thereof, comprises a heavy chain polypeptide comprising the amino acid sequence of SEQ ID NO: 14 and a light chain polypeptide comprising the amino acid sequence of SEQ ID NO: 11.

14. The method of claim 1, wherein the anti-C5 antibody or antigen binding fragment thereof, (a) binds to human C5 at pH 7.4 and 25° C. with an affinity dissociation constant (KD) that is in the range $0.1 \text{ nM} \leq KD \leq 1 \text{ nM}$; and/or (b) binds to human C5 at pH 6.0 and 25° C. with a KD >10 nM.

15. The method of claim 1, wherein the anti-C5 antibody is a biosimilar of eculizumab.

16. The method of claim 1, wherein the treatment maintains a serum trough concentration of the anti-C5 antibody or antigen binding fragment thereof, of 100 μg/mL or greater during the administration cycle.

17. The method of claim 1, wherein the complement-associated disorder is selected from the group consisting of atypical hemolytic uremic syndrome (aHUS), complement mediated thrombotic microangiopathy (CM-TMA), paroxysmal nocturnal hemoglobinuria (PNH), neuromyelitis optica spectrum disorder (NMOSD), hematopoietic stem cell transplant-associated thrombotic microangiopathy (HSCT-TMA), amyotrophic lateral sclerosis (ALS), preeclampsia hemolysis, elevated liver enzymes, low platelet count (PE-HELLP), pregnancy-induced aHUS (p-aHUS), generalized myasthenia gravis (gMG), dermatomyositis, Guillain-Barre syndrome (GBS).

18. The method of claim 1, wherein the treatment:
(a) results in terminal complement inhibition;
(b) results in a reduction of hemolysis as assessed by lactate dehydrogenase (LDH) levels;
(c) produces at least one therapeutic effect selected from the group consisting of: a reduction or cessation in fatigue, abdominal pain, dyspnea, anemia, dysphagia, chest pain, and erectile dysfunction;
(d) produces a shift toward normal levels of a hemolysis-related hematologic biomarker selected from the group consisting of: free hemoglobin, haptoglobin, reticulocyte count, PNH red blood cell (RBC) clone and D-dimer;
(e) produces a shift toward normal levels of a chronic disease associated biomarker selected from the group consisting of estimated glomerular filtration rate (eGFR) and spot urine: albumin: creatinine and plasma brain natriuretic peptide (BNP);
(f) produces a reduction in the need for blood transfusions and/or major adverse vascular events (MAVEs); and/or
(g) produces a change from Baseline in quality of life, assessed via the Functional Assessment of Chronic Illness Therapy (FACIT)-Fatigue Scale, version 4, and the European Organisation for Research and Treatment of Cancer, Quality of Life Questionnaire-Core 30 Scale.

19. The method of claim 1, wherein the SC administration attenuates free C5 levels in the patient.

20. The method of claim 1, wherein the SC administration provides a threshold level of ravulizumab for complete complement inhibition in the patient.

21. The method of claim 1, wherein the effective amount of the SC administration (a) attenuates breakthrough hemolysis in the patient; (b) provides transfusion avoidance in the patient; (c) stabilizes hemoglobin levels in the patient; (d) lowers at least one symptom of PNH in the patient.

22. The method of claim 1, wherein the patient is an adult patient between 40 kg and 100 kg.

23. A device for subcutaneous administration of an anti-C5 antibody or antigen binding fragment thereof, comprising:
a) an on-body delivery system (OBDS); and
b) a subcutaneous formulation of the anti-C5 antibody or antigen binding fragment thereof,
wherein the subcutaneous formulation of the anti-C5 antibody or antigen binding fragment thereof comprises ravulizumab (70 mg/mL) in 50 mM sodium phosphate, 25 mM arginine, 5% sucrose, 0.05% polysorbate 80, and water for injection.

\* \* \* \* \*

SEQUENCE LISTING

<160> NUMBER OF SEQ ID NOS: 50

<210> SEQ ID NO 1
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 1

Gly Tyr Ile Phe Ser Asn Tyr Trp Ile Gln
1               5                   10

<210> SEQ ID NO 2
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2

Glu Ile Leu Pro Gly Ser Gly Ser Thr Glu Tyr Thr Glu Asn Phe Lys
1               5                   10                  15

Asp

<210> SEQ ID NO 3
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Tyr Phe Phe Gly Ser Ser Pro Asn Trp Tyr Phe Asp Val
1               5                   10

<210> SEQ ID NO 4
<211> LENGTH: 11
<212> TYPE: PRT
<213> ORGANISM: Artificial Sequence
<220> FEATURE:

-continued

```
<221> NAME/KEY: source
<223> OTHER INFORMATION: /note="Description of Artificial Sequence:
      Synthetic peptide"

<400> SEQUENCE: 4

Gly Ala Ser Glu Asn Ile Tyr Gly Ala Leu Asn
1               5                   10

<210> SEQ ID NO 5
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Gly Ala Thr Asn Leu Ala Asp
1               5

<210> SEQ ID NO 6
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Gln Asn Val Leu Asn Thr Pro Leu Thr
1               5

<210> SEQ ID NO 7
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Ser Asn Tyr
            20                  25                  30

Trp Ile Gln Trp Val Arg Gln Ala Pro Gly Gln Gly Leu Glu Trp Met
        35                  40                  45

Gly Glu Ile Leu Pro Gly Ser Gly Ser Thr Glu Tyr Thr Glu Asn Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Tyr Phe Phe Gly Ser Ser Pro Asn Trp Tyr Phe Asp Val Trp
            100                 105                 110

Gly Gln Gly Thr Leu Val Thr Val Ser Ser
        115                 120

<210> SEQ ID NO 8
<211> LENGTH: 107
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Tyr Gln Gln Lys Pro Gly Lys Ala Pro Lys Leu Leu Ile
        35                  40                  45

Tyr Gly Ala Thr Asn Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Asn Val Leu Asn Thr Pro Leu
                85                  90                  95

Thr Phe Gly Gln Gly Thr Lys Val Glu Ile Lys
            100                 105

<210> SEQ ID NO 9
<211> LENGTH: 326
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 9

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
        130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Gly Leu Pro
            195                 200                 205
```

-continued

```
Ser Ser Ile Glu Lys Thr Ile Ser Lys Ala Lys Gly Gln Pro Arg Glu
    210             215             220

Pro Gln Val Tyr Thr Leu Pro Pro Ser Gln Glu Glu Met Thr Lys Asn
225             230             235             240

Gln Val Ser Leu Thr Cys Leu Val Lys Gly Phe Tyr Pro Ser Asp Ile
            245             250             255

Ala Val Glu Trp Glu Ser Asn Gly Gln Pro Glu Asn Asn Tyr Lys Thr
            260             265             270

Thr Pro Pro Val Leu Asp Ser Asp Gly Ser Phe Phe Leu Tyr Ser Arg
        275             280             285

Leu Thr Val Asp Lys Ser Arg Trp Gln Glu Gly Asn Val Phe Ser Cys
    290             295             300

Ser Val Met His Glu Ala Leu His Asn His Tyr Thr Gln Lys Ser Leu
305             310             315             320

Ser Leu Ser Leu Gly Lys
            325
```

<210> SEQ ID NO 10
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10

```
Gln Val Gln Leu Val Gln Ser Gly Ala Glu Val Lys Lys Pro Gly Ala
1               5               10              15

Ser Val Lys Val Ser Cys Lys Ala Ser Gly Tyr Ile Phe Ser Asn Tyr
            20              25              30

Trp Ile Gln Trp Val Arg Gln Ala Pro Gly Gln Gly Leu Glu Trp Met
        35              40              45

Gly Glu Ile Leu Pro Gly Ser Gly Ser Thr Glu Tyr Thr Glu Asn Phe
    50              55              60

Lys Asp Arg Val Thr Met Thr Arg Asp Thr Ser Thr Ser Thr Val Tyr
65              70              75              80

Met Glu Leu Ser Ser Leu Arg Ser Glu Asp Thr Ala Val Tyr Tyr Cys
            85              90              95

Ala Arg Tyr Phe Phe Gly Ser Ser Pro Asn Trp Tyr Phe Asp Val Trp
            100             105             110

Gly Gln Gly Thr Leu Val Thr Val Ser Ser Ala Ser Thr Lys Gly Pro
        115             120             125

Ser Val Phe Pro Leu Ala Pro Cys Ser Arg Ser Thr Ser Glu Ser Thr
    130             135             140

Ala Ala Leu Gly Cys Leu Val Lys Asp Tyr Phe Pro Glu Pro Val Thr
145             150             155             160

Val Ser Trp Asn Ser Gly Ala Leu Thr Ser Gly Val His Thr Phe Pro
            165             170             175

Ala Val Leu Gln Ser Ser Gly Leu Tyr Ser Leu Ser Ser Val Val Thr
        180             185             190

Val Pro Ser Ser Asn Phe Gly Thr Gln Thr Tyr Thr Cys Asn Val Asp
        195             200             205

His Lys Pro Ser Asn Thr Lys Val Asp Lys Thr Val Glu Arg Lys Cys
    210             215             220
```

-continued

```
Cys Val Glu Cys Pro Pro Cys Pro Ala Pro Pro Val Ala Gly Pro Ser
225                 230             235             240

Val Phe Leu Phe Pro Pro Lys Pro Lys Asp Thr Leu Met Ile Ser Arg
                245             250             255

Thr Pro Glu Val Thr Cys Val Val Val Asp Val Ser Gln Glu Asp Pro
            260             265             270

Glu Val Gln Phe Asn Trp Tyr Val Asp Gly Val Glu Val His Asn Ala
        275             280             285

Lys Thr Lys Pro Arg Glu Glu Gln Phe Asn Ser Thr Tyr Arg Val Val
    290             295             300

Ser Val Leu Thr Val Leu His Gln Asp Trp Leu Asn Gly Lys Glu Tyr
305             310             315             320

Lys Cys Lys Val Ser Asn Lys Gly Leu Pro Ser Ser Ile Glu Lys Thr
            325             330             335

Ile Ser Lys Ala Lys Gly Gln Pro Arg Glu Pro Gln Val Tyr Thr Leu
            340             345             350

Pro Pro Ser Gln Glu Glu Met Thr Lys Asn Gln Val Ser Leu Thr Cys
        355             360             365

Leu Val Lys Gly Phe Tyr Pro Ser Asp Ile Ala Val Glu Trp Glu Ser
    370             375             380

Asn Gly Gln Pro Glu Asn Asn Tyr Lys Thr Thr Pro Pro Val Leu Asp
385             390             395             400

Ser Asp Gly Ser Phe Phe Leu Tyr Ser Arg Leu Thr Val Asp Lys Ser
            405             410             415

Arg Trp Gln Glu Gly Asn Val Phe Ser Cys Ser Val Met His Glu Ala
            420             425             430

Leu His Asn His Tyr Thr Gln Lys Ser Leu Ser Leu Ser Leu Gly Lys
        435             440             445
```

```
<210> SEQ ID NO 11
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 11
```

```
Asp Ile Gln Met Thr Gln Ser Pro Ser Ser Leu Ser Ala Ser Val Gly
1               5               10              15

Asp Arg Val Thr Ile Thr Cys Gly Ala Ser Glu Asn Ile Tyr Gly Ala
            20              25              30

Leu Asn Trp Tyr Gln Gln Lys Pro Gly Lys Ala Pro Lys Leu Leu Ile
        35              40              45

Tyr Gly Ala Thr Asn Leu Ala Asp Gly Val Pro Ser Arg Phe Ser Gly
    50              55              60

Ser Gly Ser Gly Thr Asp Phe Thr Leu Thr Ile Ser Ser Leu Gln Pro
65              70              75              80

Glu Asp Phe Ala Thr Tyr Tyr Cys Gln Asn Val Leu Asn Thr Pro Leu
            85              90              95

Thr Phe Gly Gln Gly Thr Lys Val Glu Ile Lys Arg Thr Val Ala Ala
            100             105             110

Pro Ser Val Phe Ile Phe Pro Pro Ser Asp Glu Gln Leu Lys Ser Gly
        115             120             125

Thr Ala Ser Val Val Cys Leu Leu Asn Asn Phe Tyr Pro Arg Glu Ala
```

-continued

```
         130              135              140
Lys Val Gln Trp Lys Val Asp Asn Ala Leu Gln Ser Gly Asn Ser Gln
145             150              155              160

Glu Ser Val Thr Glu Gln Asp Ser Lys Asp Ser Thr Tyr Ser Leu Ser
                165              170              175

Ser Thr Leu Thr Leu Ser Lys Ala Asp Tyr Glu Lys His Lys Val Tyr
                180              185              190

Ala Cys Glu Val Thr His Gln Gly Leu Ser Ser Pro Val Thr Lys Ser
                195              200              205

Phe Asn Arg Gly Glu Cys
    210

<210> SEQ ID NO 12
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 12

Gln Val Gln Leu Val Gln Ser Gly Ala Glu Val Lys Lys Pro Gly Ala
1               5               10              15

Ser Val Lys Val Ser Cys Lys Ala Ser Gly His Ile Phe Ser Asn Tyr
                20              25              30

Trp Ile Gln Trp Val Arg Gln Ala Pro Gly Gln Gly Leu Glu Trp Met
            35              40              45

Gly Glu Ile Leu Pro Gly Ser Gly His Thr Glu Tyr Thr Glu Asn Phe
    50              55              60

Lys Asp Arg Val Thr Met Thr Arg Asp Thr Ser Thr Ser Thr Val Tyr
65              70              75              80

Met Glu Leu Ser Ser Leu Arg Ser Glu Asp Thr Ala Val Tyr Tyr Cys
                85              90              95

Ala Arg Tyr Phe Phe Gly Ser Ser Pro Asn Trp Tyr Phe Asp Val Trp
            100             105             110

Gly Gln Gly Thr Leu Val Thr Val Ser Ser
        115             120

<210> SEQ ID NO 13
<211> LENGTH: 326
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 13

Ala Ser Thr Lys Gly Pro Ser Val Phe Pro Leu Ala Pro Cys Ser Arg
1               5               10              15

Ser Thr Ser Glu Ser Thr Ala Ala Leu Gly Cys Leu Val Lys Asp Tyr
                20              25              30

Phe Pro Glu Pro Val Thr Val Ser Trp Asn Ser Gly Ala Leu Thr Ser
            35              40              45

Gly Val His Thr Phe Pro Ala Val Leu Gln Ser Ser Gly Leu Tyr Ser
    50              55              60

Leu Ser Ser Val Val Thr Val Pro Ser Ser Asn Phe Gly Thr Gln Thr
65              70              75              80
```

-continued

```
Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
               100                 105                 110

Pro Val Ala Gly Pro Ser Val Phe Leu Phe Pro Pro Lys Pro Lys Asp
               115                 120                 125

Thr Leu Met Ile Ser Arg Thr Pro Glu Val Thr Cys Val Val Val Asp
       130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
               165                 170                 175

Ser Thr Tyr Arg Val Val Ser Val Leu Thr Val Leu His Gln Asp Trp
               180                 185                 190

Leu Asn Gly Lys Glu Tyr Lys Cys Lys Val Ser Asn Lys Gly Leu Pro
               195                 200                 205

Ser Ser Ile Glu Lys Thr Ile Ser Lys Ala Lys Gly Gln Pro Arg Glu
       210                 215                 220

Pro Gln Val Tyr Thr Leu Pro Pro Ser Gln Glu Glu Met Thr Lys Asn
225                 230                 235                 240

Gln Val Ser Leu Thr Cys Leu Val Lys Gly Phe Tyr Pro Ser Asp Ile
               245                 250                 255

Ala Val Glu Trp Glu Ser Asn Gly Gln Pro Glu Asn Asn Tyr Lys Thr
               260                 265                 270

Thr Pro Pro Val Leu Asp Ser Asp Gly Ser Phe Phe Leu Tyr Ser Arg
               275                 280                 285

Leu Thr Val Asp Lys Ser Arg Trp Gln Glu Gly Asn Val Phe Ser Cys
       290                 295                 300

Ser Val Leu His Glu Ala Leu His Ser His Tyr Thr Gln Lys Ser Leu
305                 310                 315                 320

Ser Leu Ser Leu Gly Lys
               325
```

```
<210> SEQ ID NO 14
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 14

Gln Val Gln Leu Val Gln Ser Gly Ala Glu Val Lys Lys Pro Gly Ala
1               5                   10                  15

Ser Val Lys Val Ser Cys Lys Ala Ser Gly His Ile Phe Ser Asn Tyr
                20                  25                  30

Trp Ile Gln Trp Val Arg Gln Ala Pro Gly Gln Gly Leu Glu Trp Met
               35                  40                  45

Gly Glu Ile Leu Pro Gly Ser Gly His Thr Glu Tyr Thr Glu Asn Phe
       50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
               85                  90                  95
```

-continued

```
Ala Arg Tyr Phe Phe Gly Ser Ser Pro Asn Trp Tyr Phe Asp Val Trp
            100                 105                 110

Gly Gln Gly Thr Leu Val Thr Val Ser Ser Ala Ser Thr Lys Gly Pro
            115                 120                 125

Ser Val Phe Pro Leu Ala Pro Cys Ser Arg Ser Thr Ser Glu Ser Thr
        130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Asn Phe Gly Thr Gln Thr Tyr Thr Cys Asn Val Asp
            195                 200                 205

His Lys Pro Ser Asn Thr Lys Val Asp Lys Thr Val Glu Arg Lys Cys
        210                 215                 220

Cys Val Glu Cys Pro Pro Cys Pro Ala Pro Pro Val Ala Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
            275                 280                 285

Lys Thr Lys Pro Arg Glu Glu Gln Phe Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Leu His Glu Ala
            420                 425                 430

Leu His Ser His Tyr Thr Gln Lys Ser Leu Ser Leu Ser Leu Gly Lys
        435                 440                 445
```

<210> SEQ ID NO 15
<211> LENGTH: 326
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15

```
Ala Ser Thr Lys Gly Pro Ser Val Phe Pro Leu Ala Pro Cys Ser Arg
```

-continued

```
1               5                    10                   15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Thr Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
            115                 120                 125

Thr Leu Tyr Ile Thr Arg Glu Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Met Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
            195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
            245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325
```

<210> SEQ ID NO 16
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 16

```
Gln Val Gln Leu Val Gln Ser Gly Ala Glu Val Lys Lys Pro Gly Ala
1               5                    10                   15

Ser Val Lys Val Ser Cys Lys Ala Ser Gly Tyr Ile Phe Ser Asn Tyr
            20                  25                  30
```

```
Trp Ile Gln Trp Val Arg Gln Ala Pro Gly Gln Gly Leu Glu Trp Met
        35                  40                  45

Gly Glu Ile Leu Pro Gly Ser Gly Ser Thr Glu Tyr Thr Glu Asn Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Tyr Phe Phe Gly Ser Ser Pro Asn Trp Tyr Phe Asp Val Trp
            100                 105                 110

Gly Gln Gly Thr Leu Val Thr Val Ser Ser Ala Ser Thr Lys Gly Pro
            115                 120                 125

Ser Val Phe Pro Leu Ala Pro Cys Ser Arg Ser Thr Ser Glu Ser Thr
        130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
            165                 170                 175

Ala Val Leu Gln Ser Ser Gly Leu Tyr Ser Leu Ser Ser Val Val Thr
            180                 185                 190

Val Thr Ser Ser Asn Phe Gly Thr Gln Thr Tyr Thr Cys Asn Val Asp
            195                 200                 205

His Lys Pro Ser Asn Thr Lys Val Asp Lys Thr Val Glu Arg Lys Cys
        210                 215                 220

Cys Val Glu Cys Pro Pro Cys Pro Ala Pro Pro Val Ala Gly Pro Ser
225                 230                 235                 240

Val Phe Leu Phe Pro Pro Lys Pro Lys Asp Thr Leu Tyr Ile Thr Arg
            245                 250                 255

Glu Pro Glu Val Thr Cys Val Val Val Asp Val Ser His Glu Asp Pro
            260                 265                 270

Glu Val Gln Phe Asn Trp Tyr Val Asp Gly Met Glu Val His Asn Ala
        275                 280                 285

Lys Thr Lys Pro Arg Glu Glu Gln Phe Asn Ser Thr Phe Arg Val Val
        290                 295                 300

Ser Val Leu Thr Val Val His Gln Asp Trp Leu Asn Gly Lys Glu Tyr
305                 310                 315                 320

Lys Cys Lys Val Ser Asn Lys Gly Leu Pro Ala Pro Ile Glu Lys Thr
            325                 330                 335

Ile Ser Lys Thr Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Met Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445
```

```
<210> SEQ ID NO 17
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 17

Gly Ala Ser Glu Asn Ile Tyr His Ala Leu Asn
1               5                   10

<210> SEQ ID NO 18
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 18

Glu Ile Leu Pro Gly Ser Gly His Thr Glu Tyr Thr Glu Asn Phe Lys
1               5                   10                  15

Asp

<210> SEQ ID NO 19
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 19

Gly His Ile Phe Ser Asn Tyr Trp Ile Gln
1               5                   10

<210> SEQ ID NO 20
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 20

Gln Val Gln Leu Val Gln Ser Gly Ala Glu Val Lys Lys Pro Gly Ala
1               5                   10                  15

Ser Val Lys Val Ser Cys Lys Ala Ser Gly His Ile Phe Ser Asn Tyr
            20                  25                  30

Trp Ile Gln Trp Val Arg Gln Ala Pro Gly Gln Gly Leu Glu Trp Met
        35                  40                  45

Gly Glu Ile Leu Pro Gly Ser Gly His Thr Glu Tyr Thr Glu Asn Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Tyr Phe Phe Gly Ser Ser Pro Asn Trp Tyr Phe Asp Val Trp
            100                 105                 110
```

-continued

```
Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
                180                 185                 190

Val Pro Ser Ser Asn Phe Gly Thr Gln Thr Tyr Thr Cys Asn Val Asp
            195                 200                 205

His Lys Pro Ser Asn Thr Lys Val Asp Lys Thr Val Glu Arg Lys Cys
    210                 215                 220

Cys Val Glu Cys Pro Pro Cys Pro Ala Pro Pro Val Ala Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
                260                 265                 270

Glu Val Gln Phe Asn Trp Tyr Val Asp Gly Val Glu Val His Asn Ala
            275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445
```

```
<210> SEQ ID NO 21
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 21

Ser Tyr Ala Ile Ser
1               5
```

```
<210> SEQ ID NO 22
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22

Gly Ile Gly Pro Phe Phe Gly Thr Ala Asn Tyr Ala Gln Lys Phe Gln
1               5                   10                  15

Gly

<210> SEQ ID NO 23
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 23

Asp Thr Pro Tyr Phe Asp Tyr
1               5

<210> SEQ ID NO 24
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24

Ser Gly Asp Ser Ile Pro Asn Tyr Tyr Val Tyr
1               5                   10

<210> SEQ ID NO 25
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 25

Asp Asp Ser Asn Arg Pro Ser
1               5

<210> SEQ ID NO 26
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 26

Gln Ser Phe Asp Ser Ser Leu Asn Ala Glu Val
1               5                   10

<210> SEQ ID NO 27
```

```
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 27

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Val Trp Arg Gln Ala Pro Gly Gln Gly Leu Glu Trp Met
        35                  40                  45

Gly Gly Ile Gly Pro Phe Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Thr Pro Tyr Phe Asp Tyr Trp Gly Gln Gly Thr Leu Val
            100                 105                 110

Thr Val Ser Ser
        115

<210> SEQ ID NO 28
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 28

Asp Ile Glu Leu Thr Gln Pro Pro Ser Val Ser Val Ala Pro Gly Gln
1               5                   10                  15

Thr Ala Arg Ile Ser Cys Ser Gly Asp Ser Ile Pro Asn Tyr Tyr Val
            20                  25                  30

Tyr Trp Tyr Gln Gln Lys Pro Gly Gln Ala Pro Val Leu Val Ile Tyr
        35                  40                  45

Asp Asp Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Phe Asp Ser Ser Leu Asn Ala
                85                  90                  95

Glu Val Phe Gly Gly Gly Thr Lys Leu Thr Val Leu
            100                 105

<210> SEQ ID NO 29
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 29
```

-continued

```
Asn Tyr Ile Ser
1

<210> SEQ ID NO 30
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 30

Ile Ile Asp Pro Asp Asp Ser Tyr Thr Glu Tyr Ser Pro Ser Phe Gln
1               5                   10                  15

Gly

<210> SEQ ID NO 31
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 31

Tyr Glu Tyr Gly Gly Phe Asp Ile
1               5

<210> SEQ ID NO 32
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 32

Ser Gly Asp Asn Ile Gly Asn Ser Tyr Val His
1               5                   10

<210> SEQ ID NO 33
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 33

Lys Asp Asn Asp Arg Pro Ser
1               5

<210> SEQ ID NO 34
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 34

Gly Thr Tyr Asp Ile Glu Ser Tyr Val
1               5
```

```
<210> SEQ ID NO 35
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 35

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Ile Ser Trp Val Arg Gln Met Pro Gly Lys Gly Leu Glu Trp Met Gly
        35                  40                  45

Ile Ile Asp Pro Asp Asp Ser Tyr Thr Glu Tyr Ser Pro Ser Phe Gln
    50                  55                  60

Gly Gln Val Thr Ile Ser Ala Asp Lys Ser Ile Ser Thr Ala Tyr Leu
65                  70                  75                  80

Gln Trp Ser Ser Leu Lys Ala Ser Asp Thr Ala Met Tyr Tyr Cys Ala
                85                  90                  95

Arg Tyr Glu Tyr Gly Gly Phe Asp Ile Trp Gly Gln Gly Thr Leu Val
            100                 105                 110

Thr Val Ser Ser
        115

<210> SEQ ID NO 36
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 36

Ser Tyr Glu Leu Thr Gln Pro Pro Ser Val Ser Val Ala Pro Gly Gln
1               5                   10                  15

Thr Ala Arg Ile Ser Cys Ser Gly Asp Asn Ile Gly Asn Ser Tyr Val
            20                  25                  30

His Trp Tyr Gln Gln Lys Pro Gly Gln Ala Pro Val Leu Val Ile Tyr
        35                  40                  45

Lys Asp Asn Asp Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gly Thr Tyr Asp Ile Glu Ser Tyr Val
                85                  90                  95

Phe Gly Gly Gly Thr Lys Leu Thr Val Leu
            100                 105

<210> SEQ ID NO 37
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 37

Ser Ser Tyr Tyr Val Ala
1               5

<210> SEQ ID NO 38
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 38

Ala Ile Tyr Thr Gly Ser Gly Ala Thr Tyr Lys Ala Ser Trp Ala Lys
1               5                   10                  15

Gly

<210> SEQ ID NO 39
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 39

Asp Gly Gly Tyr Asp Tyr Pro Thr His Ala Met His Tyr
1               5                   10

<210> SEQ ID NO 40
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 40

Gln Ala Ser Gln Asn Ile Gly Ser Ser Leu Ala
1               5                   10

<210> SEQ ID NO 41
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 41

Gly Ala Ser Lys Thr His Ser
1               5

<210> SEQ ID NO 42
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 42
```

```
Gln Ser Thr Lys Val Gly Ser Ser Tyr Gly Asn His
1               5                   10

<210> SEQ ID NO 43
<211> LENGTH: 123
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 43

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ser His Ser Ser
            20                  25                  30

Tyr Tyr Val Ala Trp Val Arg Gln Ala Pro Gly Lys Gly Leu Glu Trp
        35                  40                  45

Val Gly Ala Ile Tyr Thr Gly Ser Gly Ala Thr Tyr Lys Ala Ser Trp
    50                  55                  60

Ala Lys Gly Arg Phe Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Ser Asp Gly Gly Tyr Asp Tyr Pro Thr His Ala Met His Tyr
                100                 105                 110

Trp Gly Gln Gly Thr Leu Val Thr Val Ser Ser
        115                 120

<210> SEQ ID NO 44
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 44

Asp Val Val Met Thr Gln Ser Pro Ser Ser Leu Ser Ala Ser Val Gly
1               5                   10                  15

Asp Arg Val Thr Ile Thr Cys Gln Ala Ser Gln Asn Ile Gly Ser Ser
            20                  25                  30

Leu Ala Trp Tyr Gln Gln Lys Pro Gly Gln Ala Pro Arg Leu Leu Ile
        35                  40                  45

Tyr Gly Ala Ser Lys Thr His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Ser Thr Lys Val Gly Ser Ser
                85                  90                  95

Tyr Gly Asn His Phe Gly Gly Gly Thr Lys Val Glu Ile Lys
            100                 105                 110

<210> SEQ ID NO 45
<211> LENGTH: 451
<212> TYPE: PRT
<213> ORGANISM: Artificial Sequence
<220> FEATURE:
```

<221> NAME/KEY: source
<223> OTHER INFORMATION: /note="Description of Artificial Sequence:
      Synthetic polypeptide"

<400> SEQUENCE: 45

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Val His Ser Ser
            20                  25                  30

Tyr Tyr Met Ala Trp Val Arg Gln Ala Pro Gly Lys Gly Leu Glu Trp
        35                  40                  45

Val Gly Ala Ile Phe Thr Gly Ser Gly Ala Glu Tyr Lys Ala Glu Trp
    50                  55                  60

Ala Lys Gly Arg Val Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
            85                  90                  95

Cys Ala Ser Asp Ala Gly Tyr Asp Tyr Pro Thr His Ala Met His Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
            165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
        210                 215                 220

Ser Cys Asp Lys Thr His Thr Cys Pro Pro Cys Pro Ala Pro Glu Leu
225                 230                 235                 240

Arg Arg Gly Pro Lys Val Phe Leu Phe Pro Pro Lys Pro Lys Asp Thr
            245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Gly Leu Pro Ser
            325                 330                 335

Ser Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr

-continued

```
385                 390                 395                 400

Pro Pro Val Leu Asp Ser Asp Gly Ser Phe Phe Leu Tyr Ser Lys Leu
            405                 410                 415

Thr Val Asp Lys Ser Arg Trp Gln Gln Gly Asn Val Phe Ser Cys Ser
            420                 425                 430

Val Leu His Glu Ala Leu His Ala His Tyr Thr Arg Lys Glu Leu Ser
            435                 440                 445

Leu Ser Pro
    450
```

```
<210> SEQ ID NO 46
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 46

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ser
            20                  25                  30

Leu Ala Trp Tyr Gln Gln Lys Pro Gly Lys Ala Pro Lys Leu Leu Ile
            35                  40                  45

Tyr Gly Ala Ser Glu Thr Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Asn Thr Lys Val Gly Ser Ser
                85                  90                  95

Tyr Gly Asn Thr Phe Gly Gly Gly Thr Lys Val Glu Ile Lys Arg Thr
            100                 105                 110

Val Ala Ala Pro Ser Val Phe Ile Phe Pro Pro Ser Asp Glu Gln Leu
            115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
            195                 200                 205

Thr Lys Ser Phe Asn Arg Gly Glu Cys
    210                 215
```

```
<210> SEQ ID NO 47
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 47
```

-continued

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Asp Ser Val Ser Ser Ser
                20                  25                  30

Tyr Trp Thr Trp Ile Arg Gln Pro Pro Gly Lys Gly Leu Glu Trp Ile
        35                  40                  45

Gly Tyr Ile Tyr Tyr Ser Gly Ser Ser Asn Tyr Asn Pro Ser Leu Lys
    50                  55                  60

Ser Arg Ala Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Gly Asn Val Asp Thr Thr Met Ile Phe Asp Tyr Trp Gly Gln
            100                 105                 110

Gly Thr Leu Val Thr Val Ser Ser
        115                 120
```

```
<210> SEQ ID NO 48
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 48
```

```
Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
                20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ala Gly
    50                  55                  60

Arg Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Phe Asn Tyr Pro Trp
                85                  90                  95

Thr Phe Gly Gln Gly Thr Lys Val Glu Ile Lys
            100                 105
```

```
<210> SEQ ID NO 49
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 49
```

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Asp Ser Val Ser Ser Ser
                20                  25                  30

Tyr Trp Thr Trp Ile Arg Gln Pro Pro Gly Lys Gly Leu Glu Trp Ile
        35                  40                  45
```

-continued

```
Gly Tyr Ile Tyr Tyr Ser Gly Ser Ser Asn Tyr Asn Pro Ser Leu Lys
    50              55              60

Ser Arg Ala Thr Ile Ser Val Asp Thr Ser Lys Asn Gln Phe Ser Leu
65              70              75              80

Lys Leu Ser Ser Val Thr Ala Ala Asp Thr Ala Val Tyr Tyr Cys Ala
            85              90              95

Arg Glu Gly Asn Val Asp Thr Thr Met Ile Phe Asp Tyr Trp Gly Gln
            100             105             110

Gly Thr Leu Val Thr Val Ser Ser Ala Ser Thr Lys Gly Pro Ser Val
            115             120             125

Phe Pro Leu Ala Pro Cys Ser Arg Ser Thr Ser Glu Ser Thr Ala Ala
    130             135             140

Leu Gly Cys Leu Val Lys Asp Tyr Phe Pro Glu Pro Val Thr Val Ser
145             150             155             160

Trp Asn Ser Gly Ala Leu Thr Ser Gly Val His Thr Phe Pro Ala Val
                165             170             175

Leu Gln Ser Ser Gly Leu Tyr Ser Leu Ser Ser Val Val Thr Val Pro
            180             185             190

Ser Ser Ser Leu Gly Thr Lys Thr Tyr Thr Cys Asn Val Asp His Lys
            195             200             205

Pro Ser Asn Thr Lys Val Asp Lys Arg Val Glu Ser Lys Tyr Gly Pro
    210             215             220

Pro Cys Pro Pro Cys Pro Ala Pro Glu Phe Leu Gly Gly Pro Ser Val
225             230             235             240

Phe Leu Phe Pro Pro Lys Pro Lys Asp Thr Leu Met Ile Ser Arg Thr
                245             250             255

Pro Glu Val Thr Cys Val Val Val Asp Val Ser Gln Glu Asp Pro Glu
            260             265             270

Val Gln Phe Asn Trp Tyr Val Asp Gly Val Glu Val His Asn Ala Lys
            275             280             285

Thr Lys Pro Arg Glu Glu Gln Phe Asn Ser Thr Tyr Arg Val Val Ser
    290             295             300

Val Leu Thr Val Leu His Gln Asp Trp Leu Asn Gly Lys Glu Tyr Lys
305             310             315             320

Cys Lys Val Ser Asn Lys Gly Leu Pro Ser Ser Ile Glu Lys Thr Ile
                325             330             335

Ser Lys Ala Lys Gly Gln Pro Arg Glu Pro Gln Val Tyr Thr Leu Pro
            340             345             350

Pro Ser Gln Glu Glu Met Thr Lys Asn Gln Val Ser Leu Thr Cys Leu
            355             360             365

Val Lys Gly Phe Tyr Pro Ser Asp Ile Ala Val Glu Trp Glu Ser Asn
    370             375             380

Gly Gln Pro Glu Asn Asn Tyr Lys Thr Thr Pro Pro Val Leu Asp Ser
385             390             395             400

Asp Gly Ser Phe Phe Leu Tyr Ser Arg Leu Thr Val Asp Lys Ser Arg
                405             410             415

Trp Gln Glu Gly Asn Val Phe Ser Cys Ser Val Met His Glu Ala Leu
            420             425             430

His Asn His Tyr Thr Gln Lys Ser Leu Ser Leu Ser Leu Gly Lys
            435             440             445
```

<210> SEQ ID NO 50
<211> LENGTH: 214
<212> TYPE: PRT

```
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 50

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ala Gly
    50                  55                  60

Arg Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Phe Asn Tyr Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```